(12) United States Patent
Smith

(10) Patent No.: US 8,551,950 B2
(45) Date of Patent: Oct. 8, 2013

(54) METHOD OF TREATMENT OR PROPHYLAXIS OF INFLAMMATORY PAIN

(75) Inventor: Maree Therese Smith, Bardon (AU)

(73) Assignee: Spinifex Pharmaceuticals Pty Ltd, South Yarra, Victoria (AU)

( * ) Notice: Subject to any disclaimer, the term of this patent is extended or adjusted under 35 U.S.C. 154(b) by 797 days.

(21) Appl. No.: 12/294,035

(22) PCT Filed: Mar. 20, 2007

(86) PCT No.: PCT/AU2007/000339
§ 371 (c)(1),
(2), (4) Date: Jun. 2, 2010

(87) PCT Pub. No.: WO2007/106938
PCT Pub. Date: Sep. 27, 2007

(65) Prior Publication Data
US 2010/0292159 A1    Nov. 18, 2010

(30) Foreign Application Priority Data

Mar. 20, 2006  (AU) ................................ 2006901413

(51) Int. Cl.
| | | |
|---|---|---|
| *A61K 38/02* | (2006.01) | |
| *A61K 31/7088* | (2006.01) | |
| *A61K 31/517* | (2006.01) | |
| *A61K 31/5377* | (2006.01) | |
| *A61K 31/496* | (2006.01) | |

(52) U.S. Cl.
USPC ... 514/18.7; 514/1.1; 514/234.8; 514/252.17; 514/266.3

(58) Field of Classification Search
None
See application file for complete search history.

(56) References Cited

U.S. PATENT DOCUMENTS

| | | | |
|---|---|---|---|
| 3,531,485 | A | 9/1970 | Freed |
| 3,975,795 | A | 8/1976 | Kupcikevicius et al. |
| 4,812,462 | A | 3/1989 | Blankley et al. |
| 5,091,390 | A | 2/1992 | Ardecky et al. |
| 5,204,354 | A | 4/1993 | Chakravarty et al. |
| 5,236,934 | A | 8/1993 | Van Atten et al. |
| 5,246,943 | A | 9/1993 | Blankley et al. |
| 5,292,726 | A | 3/1994 | Ashton et al. |
| 5,338,740 | A | 8/1994 | Carpino et al. |
| 5,348,955 | A | 9/1994 | Greenlee et al. |
| 5,385,894 | A | 1/1995 | Delaszlo et al. |
| 5,441,959 | A | 8/1995 | Chakravarty et al. |
| 5,545,651 | A | 8/1996 | Duncia et al. |
| 5,683,997 | A | 11/1997 | Buhlmayer et al. |
| 5,798,416 | A | 8/1998 | Kamata et al. |
| 6,448,280 | B1 | 9/2002 | Carey et al. |
| 2003/0158211 | A1 | 8/2003 | Bencherif et al. |
| 2003/0199424 | A1 | 10/2003 | Smith et al. |
| 2003/0220375 | A1 | 11/2003 | Wood et al. |
| 2004/0097565 | A1 | 5/2004 | Terashita et al. |
| 2004/0133011 | A1 | 7/2004 | Waddell |
| 2004/0180941 | A1 | 9/2004 | Hepworth |
| 2004/0192729 | A1 | 9/2004 | Rudolf et al. |
| 2005/0187269 | A1 | 8/2005 | Kuroita et al. |

FOREIGN PATENT DOCUMENTS

| | | |
|---|---|---|
| EP | 0245637 | 11/1987 |
| EP | 1356815 | 10/2003 |
| EP | 1239867 | 1/2005 |
| GB | 2323783 | 7/1998 |
| WO | 9205784 | 4/1992 |
| WO | 9220661 | 11/1992 |
| WO | 9320816 | 10/1993 |
| WO | 9323378 | 11/1993 |
| WO | 9413646 | 6/1994 |
| WO | 9428896 | 12/1994 |
| WO | 9500498 | 1/1995 |
| WO | 9522525 | 8/1995 |
| WO | 9907413 | 2/1999 |
| WO | 0020398 | 4/2000 |
| WO | 0144239 | 6/2001 |
| WO | WO 01/44239 | 6/2001 |
| WO | 0182916 | 11/2001 |
| WO | 0205799 | 1/2002 |
| WO | 0240008 | 5/2002 |
| WO | 02057264 | 7/2002 |
| WO | 02600923 | 8/2002 |
| WO | 03064414 | 8/2003 |
| WO | 03066577 | 8/2003 |
| WO | 03077912 | 9/2003 |
| WO | 03097024 | 11/2003 |
| WO | 03099279 | 12/2003 |
| WO | 2004006959 | 1/2004 |
| WO | 2004024061 | 3/2004 |
| WO | 2004099248 | 11/2004 |
| WO | 2005/080384 | 9/2005 |
| WO | 2006066361 | 6/2006 |
| WO | 2007134136 | 11/2007 |
| WO | 03101381 | 11/2011 |

OTHER PUBLICATIONS

Introduction to Cancer from Merck manual, p. 1. Accessed Mar. 5, 2008.*

Clinical Aspects of Cancer from Merck manual, pp. 1-4. Accessed Mar. 5, 2008.*

Rheumatoid Arthritis (RA) from Merck manual, pp. 1-12. Accessed Sep. 16, 2009.*

(Continued)

*Primary Examiner* — Julie Ha

(74) *Attorney, Agent, or Firm* — Wolff IP, a Prof. Corp.; Jessica R. Wolff

(57) ABSTRACT

A method of treatment, reversal and/or symptomatic relief of inflammatory pain, including hyperalgesia, thermal or mechanical allodynia, in vertebrate animals, particularly in human subjects, comprising administering angiotensin II receptor 2 ($AT_2$ receptor) antagonists is disclosed. The $AT_2$ receptor antagonist may be provided alone or in combination with other compounds such as those that are useful in the control of inflammatory pain.

18 Claims, 8 Drawing Sheets

(56) References Cited

OTHER PUBLICATIONS

Yamada T, Kuno A, Masuda K, Ogawa K, Sogawa M, Nakamura S, Ando T, Sano H, Nakazawa T, Ohara H, Nomura T, Joh T, Itoh M, "Candesartan, an Angiotensin II Receptor Antagonist, Suppresses Pancreatic Inflammation and Fiborsis in Rats," The Journal of Pharmacology and Experimental Therapeutics, Oct. 2003, 307: 17-23.*
Carey FA and Sunbergrj, "Advaned Organic Chemistry, 3rd Ed., Part A: Structure and Mechanisms," Plenum Press, New York, 1990, p. 146.
Carey, R.M.; (2005); "Update on the role of the AT2 receptor"; Curr. Nephrol. Hypertens; 14: 67-71.
Carrasquillo, et al.: "Rodent models clarify the role of cells expressing the substance P receptor in pain", (2004); Drug Discovery Today: disease models; 1(2): 107-113.
Chui, et al.: Non-peptide angiotensin II receptor antagonists. !!a. Pharmacology of S-8308; European Journal of Pharm., 157 (1998) 13-21.
Glinka, et al. 1994, Bioorg. Med Chem. Lett. 4: 2337.
Glinka, et al. 1994, Bioorg. Med Chem. Lett. 4:1479.
Klutchko, et al. (1994): Tetrahydroisoquinoline derivatives wit AT2-specific angiotensis II receptor binding inhibitory activity; Bioorganic & Medical Chemistry Letters; vol. 4, No. 1, pp. 57-62.
Malik, et al: Effect of angiotensin-converting-enzyme (ACE) inhibitor tandolapril on human diabetic neuropathy: randomised doublebind controlled trial; Early Report, Lancet 1998; 352: 1978-81.
PCT/AU2007/000339 International Preliminary Report on Patentability mailed May 1, 2007.
PCT/AU2007/000339 International Search Report mailed May 1, 2007.
PCT/AU2007/000339 Written Opinion mailed May 1, 2007.
PCT/GB2011/001096 International Search Report and Written Opinion mailed Aug. 29, 2011.
Pechlivanova, et al.: (2002): "Interaction of angiotensin II and adenosine A1 and A2A receptor ligands on the test in mice"; Pharmacol. Biochem. and Behaviour: 72: 23-28.
Podar, et al.: "The Role of Angiotensin Converting Enzyme Inhibitors and Angiotensin II Receptor Antagonists in the Management of Diabetic Complications," Drugs 2002:62 (14) p. 2007-2012.
Priest, et al., (1999): Biochemistry: 43: 9866-9876.
Rahbar, et al.; (1999)"Novel inhibitors of advanced glycation endproducts"; biochem. Biophys. Res. Commun.: 262: 651-656.
Stedman's Medical Dictionary 27th ed., Lippincott Williams & Wilkins, Philadelphia, 2000 "Neuropathy".
Stoll, et al., Arterioscler Thromb Vasc. Biol. (2002), 22:2, p. 231-237.
Takai, et al., "Antinociceptive Effects of Angiotensin-Converting Enzymes Inhibitors" Life Science (1996) v. 59, p. PL331-336.
Timmermans, et al., 1993 Pharmacol Reviews 45(2): 205-251.
U.S. Appl. No. 11/315,354 Final Rejection mailed Jan. 21, 2010.
U.S. Appl. No. 11/315,354 Non-Final Rejection mailed Jan. 2, 2009.
U.S. Appl. No. 11/315,354 Non-Final Rejection mailed May 22, 2009.
U.S. Appl. No. 11/315,354 Non-Final Rejection mailed Jul. 30, 2008.
Wexler, et al., (1996), J. Med. Chem., 39(3), p. 625-656.
Wolf, Gunter (2002), "The road not taken: role of angiotensin II type 2 receptor in pathophysiology" Nephrol Dial Transplant 17, p. 195-198.
Zhao, et al., J. Neurochem., (2003) 85(3), pp. 759-767.
Van Atten, et al., "A Novel Series of Selective, Non-Peptide Inhibitors of Angiotensin II Binding to the AT20 Site," J. Med. Chem. (1993), 36(25) pp. 3985-3992.
S. Takai, et al., Antinociceptive Effects of Angiotensin-Converting Enzymes Inhibitors . . . ; Life Science; (1996); vol. 59. Issue 21; pp. PL331-PL336.

* cited by examiner

METHOD OF TREATMENT OR PROPHYLAXIS OF INFLAMMATORY PAIN

PRIORITY DATA AND INCORPORATION BY REFERENCE

This is a National Stage application under 35 U.S.C. 371 of International Application No. PCT/AU2007/000339, filed Mar. 20, 2007, which claims the benefit of priority to AU Application No. 2006901413 filed Mar. 20, 2006, the entireties of which are hereby incorporated by reference.

FIELD OF THE INVENTION

This invention relates generally to compounds that are useful in the prevention and amelioration of signs and symptoms associated with inflammatory pain. More particularly, the present invention relates to the use of angiotensin II receptor 2 ($AT_2$ receptor) antagonists for the treatment, prophylaxis, reversal and/or symptomatic relief of inflammatory pain, including hyperalgesia, thermal or mechanical allodynia, in vertebrate animals and particularly in human subjects. The $AT_2$ receptor antagonists may be provided alone or in combination with other compounds such as those that are useful in the control of inflammatory conditions.

BACKGROUND OF THE INVENTION

Generally, pain is experienced when bodily tissues are subjected to mechanical, thermal or chemical stimuli of sufficient intensity to be capable of producing tissue damage. Pain resolves when the stimulus is removed or the injured tissue heals. However, under conditions of inflammatory sensitization or damage to actual nerve tissue, spontaneous pain may become chronic or permanent despite apparent tissue healing. Pain may be felt in the absence of an external stimulus and the pain experienced due to stimuli may become disproportionately intense and persistent.

Pain can take a variety of forms depending on its origin. Pain may be described as being peripheral neuropathic if the initiating injury occurs as a result of a complete or partial transection of a nerve or trauma to a nerve plexus. Alternatively, pain may be described as being central neuropathic following a lesion to the central nervous system, such as a spinal cord injury or a cerebrovascular accident. Inflammatory pain is a form of pain that is caused by tissue injury or inflammation. Following a peripheral nerve injury, symptoms are typically experienced in a chronic fashion, distal to the site of injury and are characterized by hyperesthesia (enhanced sensitivity to a natural stimulus), hyperalgesia (abnormal sensitivity to a noxious stimulus), allodynia (widespread tenderness, associated with hypersensitivity to normally innocuous tactile stimuli), and/or spontaneous burning or shooting lancinating pain.

Inflammatory pain has a distinct etiology, as compared to other forms of pain. After initiation of inflammation in peripheral tissues, functionally specialized primary afferent nerve fiber endings called nociceptors become sensitized resulting in the development of inflammatory pain. Examples include the pain that develops in association with inflammatory conditions such as arthritis, tendonitis and bursitis. Inflammatory pain may also arise from the viscera and an example is inflammatory bowel disease. Inflammatory pain is also often a component of cancer pain, post-operative pain, trauma pain and burns pain.

Inflammation-induced nociceptor sensitization leads to increased sensitivity and amplified responses so that pain may be produced by low-intensity or normally innocuous stimuli. Further, inflammatory pain involves neuroplastic changes at multiple levels of the nervous system including the nociceptors themselves, the dorsal root ganglia (DRGs), the dorsal horn of the spinal cord and the brain (Woolf and Costigan, 1999, *Proc Natl Acad Sci USA* 96: 7723-7730).

After initiation of inflammation, intracellular contents leak into the extracellular fluid, inflammatory cells are recruited and there is increased production and release of a broad range of pro-nociceptive (i.e. pro-pain) molecules e.g. protons, serotonin (5HT), histamine, adenosine, adenosine triphosphate (ATP), bradykinin, prostaglandin$E_2$ ($PGE_2$), nitric oxide (NO), interleukin-1 (IL-1), tumor necrosis factor alpha (TNFα), interleukin-6 (IL-6), leukemia inhibitory factor (LIF), nerve growth factor (NGF), by inflammatory and other cells. Exposure of nociceptors to this pro-inflammatory "soup" has the potential to cause sensitization so that innocuous stimuli are detected as painful (allodynia) or there is a heightened response to noxious stimuli (hyperalgesia) (Millan M J, 1999, *Prog in Neurobiol* 57: 1-164). This in turn initiates early post-translational changes in the nociceptors thereby altering transduction sensitivity (peripheral sensitization) which may in turn increase C-fiber activity producing subsequent sensitization of dorsal horn neurons (central sensitization). Both peripheral and central sensitization alter basal sensitivity to noxious and non-noxious stimuli (Woolf and Costigan, 1999, supra; Porreca et al., 1999, *Proc Natl Acad Sci USA* 96: 7640-7644). Additionally, there are other longer-lasting transcription-dependent changes in both the DRGs and the dorsal horn of the spinal cord involving the retrograde transport of specific signaling molecules e.g. nerve growth factor (NGF), which is produced as a result of inflammation. The net result is that inflammation results in a potentiated nociceptive signaling system as well as a system whereby phenotypic changes in low-threshold Aβ-fiber inputs have the potential to contribute to the development of stimulus-evoked rather than basal hypersensitivity (Woolf and Costigan, 1999, supra; Neumann et al., 1996, *Nature* (London) 384: 360-364).

Although nociceptors are defined by their normally high threshold for activation, lower intensity stimuli will activate sensitized nociceptors. Peripheral sensitization, which can be detected within a very short period, is thought to involve changes either in the transducing molecules/receptors themselves or in the $Na^+$ channels in the nerve terminals (Woolf and Costigan, 1999, supra). A change in the transducer is best exemplified by the TRPV1 receptor, where repeated heat stimuli or exposure to protons progressively augments the inward current through the TRPV1 receptor ion channel (Caterina et al., 1997, *Nature* (London) 389: 816-24; Tominaga et al., 1998, *J Neurosci* 18: 10345-55). Additionally, phosphorylation of membrane-bound receptor/ion channels may occur as many inflammatory mediators activate protein kinases thereby increasing receptor phosphorylation. Phosphorylation of the peripherally located tetrodotoxin[1]-resistant (TTXr) sodium channels, results in a greater sodium current in the terminal (Gold et al., 1998, *J Neurosci* 18: 10345-10355; England et al., 1996, *J Physiol* (London) 495: 429-40; Gold et al., 1996, *Proc Natl Acad Sci USA* 93: 1108-12). These sensitizing changes occur locally in the peripheral nerve terminal, independent of any transcriptional changes that may occur in the neuronal cell bodies located in the DRGs.

Tetrodotoxin is a neurotoxin from the puffer fish

Inflammation increases peripheral levels of NGF (Woolf et al., 1994, *Neuroscience* 62: 327-31), a neurotrophin thought to play a key role in inducing transcriptional changes such as upregulation of TRPV1-receptors and sensory-neuron-specific $Na^+$-channels (Tate et al., 1998, *Nat Neurosci* 1: 653-55; Okuse et al., 1997, *Mol Cell Biol* 10: 196-207) in inflammatory states. Although peripheral sensitization does not itself require transcription, upregulated synthesis of components of the pain signaling system has the potential to amplify peripheral sensitization. After initiation of inflammation, there is a delay of many hours for up-regulated expression and transport of proteins to occur (Woolf and Costigan, 1999, supra).

Central sensitization of the spinal cord results in an NMDA receptor-sensitive increase in responsiveness to low- and high-intensity stimuli, both when applied to the site of inflammation (1° hyperalgesia) and in the contiguous non-inflamed area (2° hyperalgesia). Tactile allodynia and pin prick hyperalgesia in the zone of 2° hyperalgesia (Koltzenburg et al., 1992, *Pain* 51: 207-20) are characteristic NMDA receptor-mediated features of central sensitization (Stubhaug et al., 1997, *Acta Anaesthesiol Scand* 41: 1124-32). A consequence of inflammation-induced transcriptional changes in DRG neurons is that some low-threshold Aβ fibers may acquire the neurochemical phenotype typical of C-fibers such as synthesis and storage of substance P (Neumann et al., 1996, *Nature* 384: 360-364). This change in neurochemical expression together with the inflammation-induced increase in neurokinin-1 (NK-1) receptors in the dorsal horn of the spinal cord (Krause et al., 1995, *Can J Physiol Pharmacol* 73: 854-859) produce not only a potentiated system but one in which the specific type of stimulus that can evoke central sensitization has changed. Stimulus-induced hypersensitivity can thus be mediated by low-intensity Aβ inputs as well as high-intensity C-fiber inputs which manifests as progressive tactile allodynia where light touch produces a progressive increase in excitability of spinal cord neurons, something that would not happen in the non-inflamed state (Neumann et al., 1996, supra; Ma and Woolf, 1996, *Pain* 67: 97-106; Ma and Woolf, 1997, *NeuroReport* 8, 807-810; Ma and Woolf, 1997, *Eur J Pharmacol* 322: 165-171; Ma et al., 1998, *Pain* 77: 49-57).

Current methods for treating inflammatory pain have many drawbacks and deficiencies. For example, corticosteroids, which are commonly used to suppress destructive autoimmune processes, can result in undesirable side effects including, but not limited to, vulnerability to infection, weakening of tissues and loss of bone density leading to fractures, and ocular cataract formation. Non-steroidal anti-inflammatory drugs may cause gastrointestinal disturbances including ulceration and gastrointestinal bleeding, skin rashes and urticaria and interstitial nephritis. More recently, the cardiovascular safety of the selective cyclooxygenase-2 (COX-2) inhibitors has been raised as a potentially serious concern when these agents are administered chronically for periods longer than one year.

Thus, better therapeutic strategies are required for the treatment and management of inflammatory pain.

SUMMARY OF THE INVENTION

The present invention arises from the unexpected discovery that $AT_2$ receptor antagonists are effective in the prevention or attenuation of the painful symptoms of inflammatory pain. Accordingly, in one aspect, the invention provides methods for the treatment or prophylaxis of inflammatory pain, including acute and chronic inflammatory pain, in a subject by administering to the subject an effective amount of an $AT_2$ receptor antagonist. Non limiting examples of suitable $AT_2$ receptor antagonists include small molecules, nucleic acids, peptides, polypeptides, peptidomimetics, carbohydrates, lipids or other organic (carbon containing) or inorganic molecules, as further described herein.

The $AT_2$ receptor antagonist is suitably administered in the form of a composition comprising a pharmaceutically acceptable carrier or diluent. The composition may be administered by injection, by topical application or by the oral route including sustained-release modes of administration, over a period of time and in amounts, which are effective to treat or prevent the symptoms of inflammatory pain. In some embodiments, the inflammatory pain results from an infection, a burn, an autoimmune disease, an inflammatory condition of the skin, muscle, or joints, a cancer, a traumatic injury or surgery.

In accordance with the present invention, $AT_2$ receptor antagonists have been shown to prevent or attenuate the painful symptoms associated with inflammatory pain. Thus, in another aspect, the invention provides methods for preventing or attenuating the symptoms of inflammatory pain in a subject by administering to the subject an effective amount of an $AT_2$ receptor antagonist, which is suitably in the form of a composition comprising a pharmaceutically acceptable carrier and/or diluent.

In a related aspect, the invention provides methods for producing analgesia in a subject, especially in a subject who has, or is at risk of developing, inflammatory pain. These methods generally comprise administering to the subject an effective amount of an $AT_2$ receptor antagonist, which is suitably in the form of a composition comprising a pharmaceutically acceptable carrier and/or diluent.

In a further aspect, the present invention contemplates the use of an $AT_2$ receptor antagonist in the manufacture of a medicament for producing analgesia in a subject, especially in a subject who has, or is at risk of developing, inflammatory pain.

Any $AT_2$ receptor antagonist can be used in the compositions and methods of the invention. In some embodiments, the $AT_2$ receptor antagonist is selected from compounds, and their pharmaceutically compatible salts, represented by the formula (I):

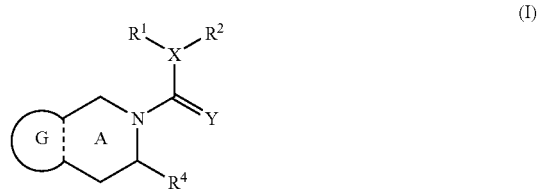

wherein:
$R^1$ and $R^2$ are independently selected from H, benzyl, substituted benzyl, phenyl, substituted phenyl, $C_{1-6}$alkyl, substituted $C_{1-6}$alkyl, $C_{3-6}$cycloalkyl, substituted $C_{3-6}$cycloalkyl, and heteroaryl, providing that both $R^1$ and $R^2$ are not hydrogen,
$R^4$ is selected from a carboxylate, carboxylic acid, sulfate, phosphate, sulfonamide, phosphonamide or amide,
X is selected from CH, nitrogen, sulfur or oxygen with the proviso that when X is sulfur or oxygen one of $R^1$ or $R^2$ is absent,
Y is selected from sulfur, oxygen or N—$R^N$, where $R^N$ is selected from H, $C_{1-6}$alkyl, substituted $C_{1-6}$alkyl, aryl, substituted aryl, benzyl, substituted benzyl, $C_{1-4}$alkylaryl, substituted $C_{1-4}$alkylaryl, OH, or $NH_2$,
G is a five or six membered, homoaromatic or unsaturated, substituted or unsubstituted, heterocyclic ring including but not limited to the following rings systems:

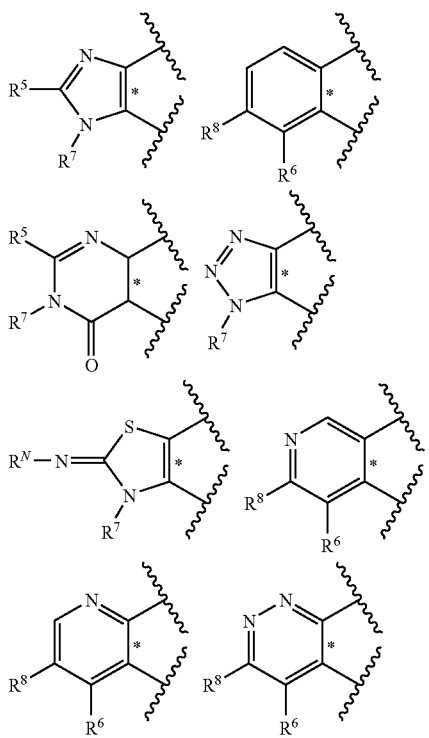

where the symbol '*' indicates the bond shared between the fused rings 'A' and 'G', $R^5$ is selected from H, $C_{1-6}$alkyl, phenyl, substituted phenyl, substituted $C_{1-6}$alkyl, $C_{1-6}$alkoxy, or substituted $C_{1-6}$alkoxy, $R^6$ and $R^8$ are independently selected from H, $C_{1-6}$alkyl, substituted $C_{1-6}$alkyl, $C_{1-6}$alkoxy, substituted $C_{1-6}$alkoxy, phenyl, phenyloxy, benzyl, benzyloxy, benzylamino, biphenyl, substituted biphenyl, biphenyloxy, substituted biphenyloxy, napthyl, substituted napthyl, provided that one of $R^6$ or $R^8$ is not hydrogen, and $R^7$ is selected from phenyl, substituted phenyl, benzyl, substituted benzyl, biphenyl, substituted biphenyl, biphenylmethylene, substituted biphenylmethylene, napthyl, substituted napthyl, naphthylmethylene, and substituted naphthylmethylene.

In other embodiments, the $AT_2$ receptor antagonist is selected from compounds, and their pharmaceutically compatible salts, represented by the formula (II):

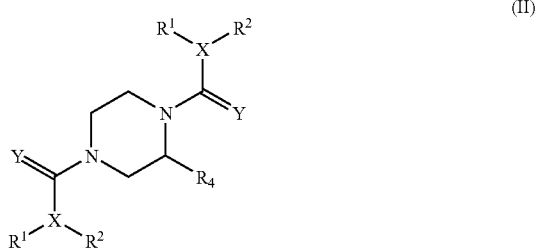

wherein:
$R^1$ and $R^2$ are independently selected from H, phenyl, substituted phenyl, benzyl, substituted benzyl, $C_{1-6}$alkyl, substituted $C_{1-6}$alkyl, $C_{3-6}$cylcoalkyl, substituted $C_{3-6}$cycloalkyl, heteroaryl, and substituted heteroaryl, substituted biphenylmethylene and saturated and unsaturated substituted biphenylmethylene, provided that one of $R^1$ or $R^2$ is not hydrogen, $R^4$ is selected from a carboxylate, carboxylic acid, sulfate, phosphate, sulfonamide, phosphonamide or amide, X is selected from CH, nitrogen, sulfur or oxygen with the proviso that when X is sulfur or oxygen one of $R^1$ or $R^2$ is absent, and Y is selected from sulfur, oxygen or N—$R^N$, where $R^N$ is selected from H, $C_{1-6}$alkyl, substituted $C_{1-6}$alkyl, aryl, substituted aryl, benzyl, substituted benzyl, $C_{1-4}$alkylaryl, substituted $C_{1-4}$alkylaryl, OH, or $NH_2$, In still other embodiments, the $AT_2$ receptor antagonist is selected from compounds, and their pharmaceutically compatible salts, represented by the formula (III):

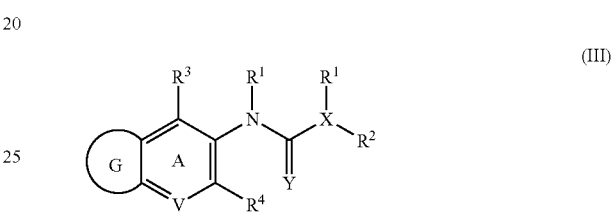

wherein:
$R^1$, $R^2$ and $R^3$ are independently selected from H, phenyl, substituted phenyl, benzyl substituted benzyl, $C_{1-6}$alkyl, substituted $C_{1-6}$alkyl, with the proviso that at least one of $R^1$ or $R^2$ are not hydrogen, X is selected from CH, nitrogen, sulfur or oxygen with the proviso that when X is sulfur or oxygen, one of $R^1$ or $R^2$ is absent, or is aryl or heteroaryl with the proviso that both $R^1$ and $R^2$ are absent, V is selected from CH or nitrogen atom, Y is selected from sulfur, oxygen or N—$R^N$, where $R^N$ is selected from H, $C_{1-6}$alkyl, substituted $C_{1-6}$alkyl, aryl, substituted aryl, benzyl, substituted benzyl, $C_{1-4}$alkylaryl, substituted $C_{1-4}$alkylaryl, OH, or $NH_2$, $R^4$ is selected from a carboxylate, carboxylic acid, sulfate, phosphate, sulfonamide, phosphonamide, or amide, G is a five or six membered, homoaromatic or unsaturated, substituted or unsubstituted, heterocyclic ring including but not limited to the following rings systems:

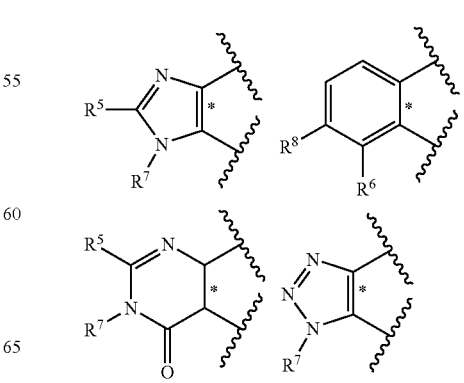

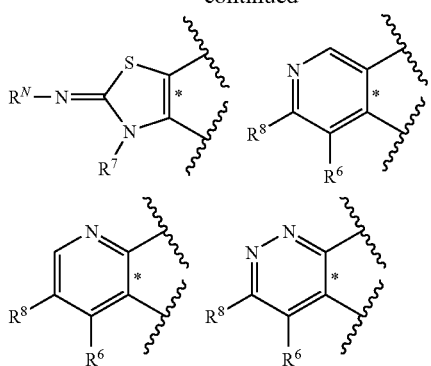

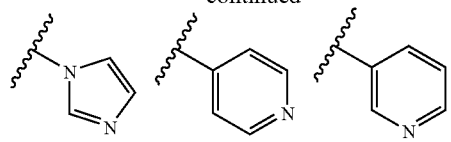

where the symbol '*' indicates the bond shared between the fused rings 'A' and 'G', $R^3$ is selected from H, $C_{1-6}$alkyl, phenyl, substituted phenyl, substituted $C_{1-6}$alkyl, or $C_{1-6}$alkoxy, $R^6$ and $R^8$ are independently selected from H, $C_{1-6}$alkyl, substituted $C_{1-6}$alkyl $C_{1-6}$alkoxy, substituted, $C_{1-6}$alkoxy, phenyl, phenyloxy, benzyl, benzyloxy, benzylamino, biphenyl, substituted biphenyl, biphenyloxy, substituted biphenyloxy, napthyl, substituted napthyl, provided that one of $R^6$ or $R^8$ is not hydrogen, and $R^7$ is selected from phenyl, substituted phenyl, benzyl, substituted benzyl, biphenyl, substituted biphenyl, biphenylmethylene, substituted biphenylmethylene, napthyl, substituted napthyl, naphthylmethylene, and substituted naphthylmethylene.

In still other embodiments, the $AT_2$ receptor antagonist is selected from compounds, and their pharmaceutically compatible salts, represented by the formula (IV):

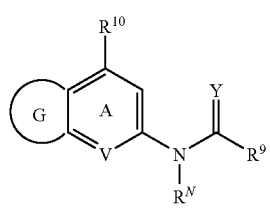
(IV)

wherein:

$R^{10}$ is selected from H, halogen, $C_{1-6}$alkyl, phenyl, substituted phenyl, substituted $C_{1-6}$alkyl, or $C_{1-6}$alkoxy, $R^9$ is selected from —$NR^{13}R^{14}$, wherein $R^{13}$ and $R^{14}$ are independently selected from $C_{1-6}$alkyl, substituted $C_{1-6}$alkyl, aryl, substituted aryl, benzyl, substituted benzyl, $C_{1-4}$ alkyl aryl, substituted $C_{1-4}$alkylaryl, OH, or $NH_2$; a five or six membered, saturated or unsaturated, substituted or unsubstituted, carbocyclic or heterocyclic ring including but not limited to:

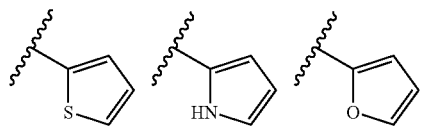

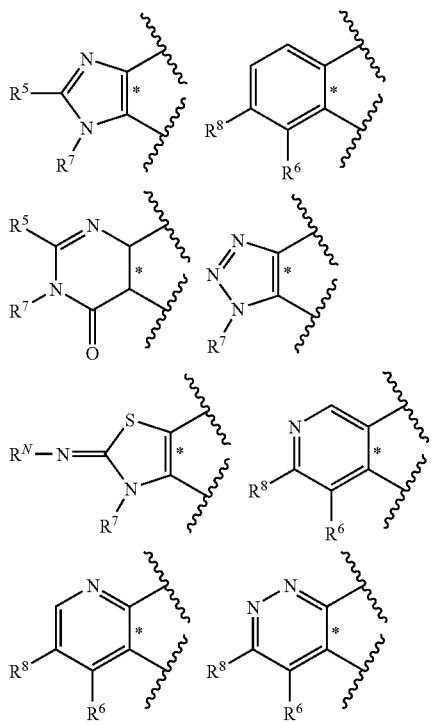

V is selected from CH or a nitrogen atom,

Y is selected from sulfur, oxygen or N—$R^N$, where $R^N$ is selected from H, $C_{1-6}$alkyl, substituted $C_{1-6}$alkyl, aryl, substituted aryl, benzyl, substituted benzyl, $C_{1-4}$alkylaryl, substituted $C_{1-4}$alkylaryl, OH, or $NH_2$, G is a five or six membered homoaromatic or heterocyclic, unsaturated, substituted ring including but not limited to the following rings systems:

where the symbol '*' indicates the bond shared between the fused rings 'A' and 'G', $R^5$ is selected from $C_{1-6}$alkyl, phenyl, substituted phenyl, substituted $C_{1-6}$alkyl, or $C_{1-6}$alkoxy, W is selected from sulfur, oxygen or N—$R^N$, where $R^N$ is selected from H, $C_{1-6}$alkyl, substituted $C_{1-6}$alkyl, aryl, substituted aryl, benzyl, substituted benzyl, $C_{1-4}$alkylaryl, substituted $C_{1-4}$alkylaryl, OH, or $NH_2$.

$R^6$ and $R^8$ are independently selected from H, $C_{1-6}$alkyl, substituted $C_{1-6}$alkyl $C_{1-6}$alkoxy, substituted, $C_{1-6}$alkoxy, phenyl, phenyloxy, benzyl, benzyloxy, benzylamino, biphenyl, substituted biphenyl, biphenyloxy, substituted biphenyloxy, napthyl, substituted napthyl, provided that one of $R^6$ or $R^8$ is not hydrogen, and $R^7$ is selected from phenyl, substituted phenyl, benzyl, substituted benzyl, biphenyl, substituted biphenyl, biphenylmethylene, substituted biphenylmethylene, napthyl, substituted napthyl, naphthylmethylene, and substituted naphthylmethylene.

In still other embodiments, the $AT_2$ receptor antagonist is selected from compounds, and their pharmaceutically compatible salts, represented by the formula (V):

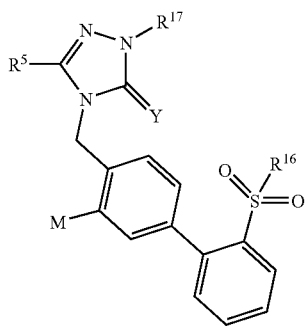

(V)

wherein:
M is H or a halogen (fluoro, bromo, iodo, chloro),
$R^5$ is selected from $C_{1-6}$alkyl, phenyl, substituted phenyl, substituted $C_{1-6}$alkyl, or $C_{1-6}$alkoxy,
$R^{16}$ is selected from $C_{1-6}$alkylamino, $C_{1-6}$dialkylamino, substituted $C_{1-6}$alkylamino, substituted dialkylamino, arylamino, diarylamino, substituted arylamino, substituted diarylamino, alkylarylamino, dialkylarylamino, substituted alkylarylamino, substituted dialkylarylamino, heteroarylamino, substituted heteroarylamino, cycloalkylamino, dicycloalkylamino, diheteroarylamino, alkylcarbonylamino, arylcarbonylamino, alkylarylcarbonylamino, cycloalkylcarbonylamino, and
$R^{17}$ is selected from $C_{1-6}$alkyl, substituted $C_{1-6}$alkyl, phenyl, substituted phenyl, benzyl, substituted benzyl, biphenyl, substituted biphenyl, biphenylmethylene, substituted biphenylmethylene, naphthyl, substituted naphthyl, heteroaryl, or substituted heteroaryl.

In further embodiments, the $AT_2$ receptor antagonist is selected from $AT_2$ receptor antagonist peptides, illustrative examples of which include hexa-, hepta- and octapeptides, and their pharmaceutically compatible salts, represented by the formula:

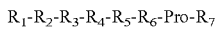

$$R_1\text{-}R_2\text{-}R_3\text{-}R_4\text{-}R_5\text{-}R_6\text{-}Pro\text{-}R_7 \quad \text{(VIII)}$$

wherein:
$R_1$ is absent or is selected from hydrogen, succinyl, L-aspartyl, sarcosyl, L-seryl, succinamyl, L-propyl, glycyl, L-tyrosyl, $N_\alpha$-nicotinoyl-tyrosyl, or D- or L-asparagyl;
$R_2$ is selected from arginyl or N-benzoylcarbonyl arginyl;
$R_3$ is absent or valyl;
$R_4$ is absent or is selected from L-phenylalanyl or L-tyrosyl;
$R_5$ is selected from valyl, L-isoleucyl, L-alanyl or L-lysyl;
$R_6$ is selected from L-histidyl, L-isoleucyl, L-tyrosyl or p-aminophenylalanyl; and
$R_7$ is selected from L-alanine, L-tyrosine, L- or D-leucine, glycine, L-isoleucine or β-alanine residue.

In other embodiments, the $AT_2$ receptor antagonist is selected from antigen-binding molecules that are immuno-interactive with an $AT_2$ receptor polypeptide.

In still other embodiments, the $AT_2$ receptor antagonist is selected from nucleic acid molecules that inhibit or otherwise reduce the level or functional activity of an expression product of an $AT_2$ receptor gene, illustrative examples of which include antisense molecules, ribozymes and RNAi molecules.

In yet another aspect, the invention provides methods for identifying agents that antagonize an $AT_2$ receptor. These methods typically comprise contacting a preparation with a test agent, wherein the preparation comprises (i) a polypeptide comprising an amino acid sequence corresponding to at least a biologically active fragment of an $AT_2$ receptor polypeptide, or to a variant or derivative thereof; or (ii) a polynucleotide that comprises at least a portion of a genetic sequence that regulates the expression of a gene that encodes an $AT_2$ receptor polypeptide, wherein the polynucleotide is operably linked to a reporter gene. A detected decrease in the level or functional activity of the $AT_2$ receptor polypeptide, or an expression product of the reporter gene, relative to a normal or reference level or functional activity in the absence of the test agent, indicates that the agent is an $AT_2$ receptor antagonist.

In some embodiments, the methods comprise contacting a first sample of cells expressing an $AT_2$ receptor with an $AT_2$ receptor ligand and measuring a marker; contacting a second sample of cells expressing the $AT_2$ receptor with an agent and the ligand, and measuring the marker; and comparing the marker of the first sample of cells with the marker of the second sample of cells. In illustrative examples, these methods measure the levels of various markers (e.g., Zfhep expression; nitric oxide levels or nitric oxide synthase levels) or combinations of markers associated with the activation of the AT2 receptor or with the proliferation or differentiation of the cells. In these examples, an agent tests positive if it inhibits Zfhep expression or reduces the level of nitric oxide or the level or functional activity of nitric oxide synthase or the differentiation of the cells.

Still another aspect of the present invention provides methods of producing an agent for producing analgesia in a subject, especially in a subject who has, or is at risk of developing, inflammatory pain. These methods generally comprise: testing an agent suspected of antagonizing an $AT_2$ receptor, as broadly described above; and synthesizing the agent on the basis that it tests positive for the antagonism. Suitably, the method further comprises derivatising the agent, and optionally formulating the derivatized agent with a pharmaceutically acceptable carrier or diluent, to improve the efficacy of the agent for treating or preventing inflammatory pain.

DETAILED DESCRIPTION OF THE INVENTION

1. Definitions

Figure 1:
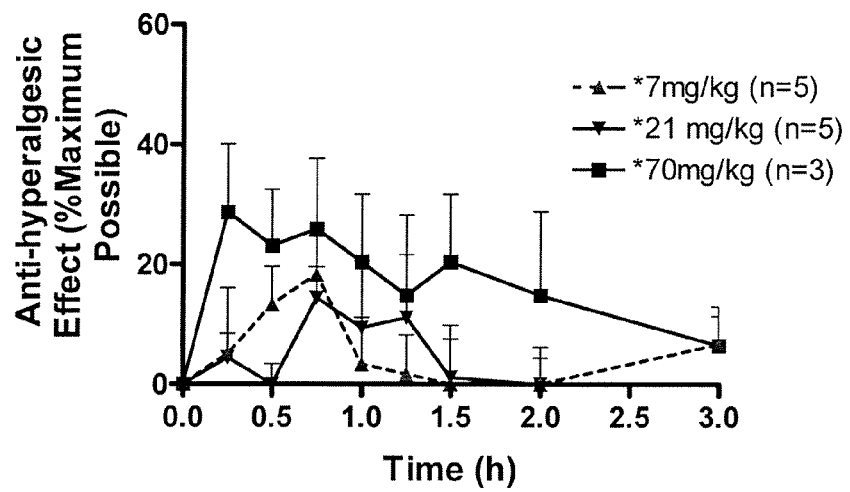
FIG. 1 is a graphical representation showing that PD-123, 319 produces dose-dependent relief of mechanical hyperalgesia in the ipsilateral (inflamed) hindpaw of the FCA-rat model of inflammatory pain when assessed using the Paw Pressure Test involving the application of noxious pressure to the inflamed hindpaw. Asterisk denotes estimated doses due to previously noted impurity of test compound.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 30%, 25%, 20%, 15% or 10% to a reference quantity, level, value, dimension, size, or amount.

Unless otherwise indicated, the term "acyl" denotes a group containing the moiety C=O (and not being a carboxylic acid, ester or amide) Preferred acyl includes C(O)—R, wherein R is hydrogen or an alkyl, alkenyl, alkynyl, aryl, heteroaryl or heterocyclyl residue, preferably a $C_{1-20}$ residue. Examples of acyl include formyl; straight chain or branched alkanoyl such as, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; cycloalkylcarbonyl such as cyclopropylcarbonyl cyclobutylcarbonyl, cyclopentylcarbonyl and cyclohexylcarbonyl; aroyl such as benzoyl, toluoyl and naphthoyl; aralkanoyl such as phenylalkanoyl (e.g. phenylacetyl, phenylpropanoyl, phenylbutanoyl, phenylisobutanoyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aryloxyalkanoyl such as phenoxyacetyl and phenoxypropionyl; arylthiocarbamoyl such as phenylthiocarbamoyl; arylglyoxyloyl such as phenylglyoxyloyl and naphthylglyoxyloyl; arylsulfonyl such as phenylsulfonyl and naphthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolyglyoxyloyl and thienylglyoxyloyl.

If a number of carbon atoms is not specified, the term "alkenyl," unless otherwise indicated, refers to a non-aromatic hydrocarbon radical, straight, branched or cyclic, containing from 2 to 10 carbon atoms and at least one carbon to carbon double bond. Preferably one carbon to carbon double bond is present, and up to four non-aromatic carbon-carbon double bonds may be present. Thus, "$C_2$-$C_6$alkenyl" means an alkenyl radical having from 2 to 6 carbon atoms. Alkenyl groups include, but are not limited to, ethenyl, propenyl, butenyl, 2-methylbutenyl and cyclohexenyl. The straight, branched or cyclic portion of the alkenyl group may contain double bonds and may be substituted if a substituted alkenyl group is indicated.

As used herein, "alkenylene" refers to a straight, branched or cyclic, preferably straight or branched, bivalent aliphatic hydrocarbon group, preferably having from 2 to about 20 carbon atoms and at least one double bond, more preferably 2 to 12 carbons, even more preferably lower alkenylene. The alkenylene group is optionally substituted with one or more "alkyl group substituents." There may be optionally inserted along the alkenylene group one or more oxygen, sulfur or substituted or unsubstituted nitrogen atoms, where the nitrogen substituent is alkyl as previously described. Exemplary alkenylene groups include —CH=CH—CH=CH— and —CH=CH—CH$_2$—. The term "lower alkenylene" refers to alkenylene groups having 2 to 6 carbons. Preferred alkenylene groups are lower alkenylene, with alkenylene of 3 to 4 carbon atoms being particularly preferred.

The terms "alkoxy," "alkenoxy," "alkynoxy," "aryloxy," "heteroaryloxy," "heterocyclyloxy" and "acyloxy" respectively denote alkyl, alkenyl, alkynyl aryl, heteroaryl, heterocyclyl and acyl groups as herein defined when linked by oxygen.

"Alkoxy," unless otherwise indicated, represents either a cyclic or non-cyclic alkyl group attached through an oxygen bridge. "Alkoxy" therefore encompasses the definitions of alkyl and cycloalkyl below. For example, alkoxy groups include but are not limited to methoxy, oxy ethoxy, n-propyloxy, i-propyloxy, cyclopentyloxy and cyclohexyloxy.

As used herein, "alkyl" is intended to include both branched and straight-chain saturated aliphatic hydrocarbon group and may have a specified number of carbon atoms. For example, $C_1$-$C_{10}$, as in "$C_1$-$C_{10}$alkyl" is defined to include groups having 1, 2, 3, 4, 5, 6, 7, 8, 9 or 10 carbons in linear or branched arrangement. For example, "$C_1$-$C_{10}$alkyl" specifically includes, but is not limited to, methyl, ethyl, n-propyl, i-propyl, n-butyl, t-butyl, i-butyl, pentyl, hexyl, heptyl, octyl, nonyl, decyl.

As used herein, "alkylene" refers to a straight, branched or cyclic, preferably straight or branched, bivalent aliphatic hydrocarbon group, preferably having from 1 to about 20 carbon atoms, more preferably 1 to 12 carbons, even more preferably lower alkylene. The alkylene group is optionally substituted with one or more "alkyl group substituents." There may be optionally inserted along the alkylene group one or more oxygen, sulfur or substituted or unsubstituted nitrogen atoms, where the nitrogen substituent is alkyl as previously described. Exemplary alkylene groups include methylene (—CH$_2$—), ethylene (—CH$_2$CH$_2$—), propylene (—(CH$_2$)$_3$—), cyclohexylene (—C$_6$H$_{10}$—), methylenedioxy (—O—CH$_2$—O—) and ethylenedioxy (—O—(CH$_2$)$_2$—O—). The term "lower alkylene" refers to alkylene groups having 1 to 6 carbons. Preferred alkylene groups are lower alkylene, with alkylene of 1 to 3 carbon atoms being particularly preferred.

As used herein, "alkylidene" refers to a bivalent group, such as =CR9R0, which is attached to one atom of another group, forming a double bond. Exemplary alkylidene groups are methylidene (=CH$_2$) and ethylidene (=CHCH$_3$). As used herein, "arylalkylidene" refers to an alkylidene group in which either R9 or R0 is and aryl group. As used herein, "diarylalkylidene" refers to an alkylidene group in which R9 and R0 are both aryl groups. "Diheteroarylalkylidene" refers to an alkylidene group in which R9 and R0 are both heteroaryl groups.

The term "alkynyl" refers to a hydrocarbon radical straight, branched or cyclic, containing from 2 to 10 carbon atoms and at least one carbon to carbon triple bond. Up to three carbon-carbon triple bonds may be present. Thus, "C$_2$-C$_6$alkynyl" means an alkynyl radical having from 2 to 6 carbon atoms. Alkynyl groups include, but are not limited to, ethynyl, propynyl, butynyl, 3-methylbutynyl and so on. The straight, branched or cyclic portion of the alkynyl group may contain triple bonds and may be substituted if a substituted alkynyl group is indicated.

In certain instances, substituents may be defined with a range of carbons that includes zero, such as (C$_0$-C$_6$)alkylene-aryl. If aryl is taken to be phenyl, this definition would include phenyl itself as well as, for example, —CH$_2$Ph, —CH$_2$CH$_2$Ph, CH(CH$_3$)CH$_2$CH(CH$_3$)Ph.

As used herein, "alkynylene" refers to a straight, branched or cyclic, preferably straight or branched, bivalent aliphatic hydrocarbon group, preferably having from 2 to about 20 carbon atoms and at least one triple bond, more preferably 2 to 12 carbons, even more preferably lower alkynylene. The alkynylene group is optionally substituted with one or more "alkyl group substituents." There may be optionally inserted along the alkynylene group one or more oxygen, sulfur or substituted or unsubstituted nitrogen atoms, where the nitrogen substituent is alkyl as previously described. Exemplary alkynylene groups include —C≡C—C≡C—, —C≡C— and —C≡C—CH$_2$—. The term "lower alkynylene" refers to alkynylene groups having 2 to 6 carbons. Preferred alkynylene groups are lower alkynylene, with alkynylene of 3 to 4 carbon atoms being particularly preferred.

The term "analgesia" is used herein to describe states of reduced pain perception, including absence from pain sensations as well as states of reduced or absent sensitivity to noxious stimuli. Such states of reduced or absent pain perception are induced by the administration of a pain-controlling agent or agents and occur without loss of consciousness, as is commonly understood in the art. The term analgesia encompasses the term "antinociception," which is used in the art as a quantitative measure of analgesia or reduced pain sensitivity in animal models.

As used herein, the term "antagonist" means an agent that decreases or inhibits the biological activity of an AT$_2$ gene (Agtr2 gene) or an expression product thereof including an AT$_2$ receptor polypeptide.

As used herein, the term "AT$_2$ receptor" means an angiotensin II type 2 receptor (AT$_2$) receptor polypeptide that can bind angiotensin II and/or one or more other ligands. The term "AT$_2$ receptor" encompasses vertebrate homologs of AT$_2$ receptor family members, including, but not limited to, mammalian, reptilian and avian homologs. Representative mammalian homologs of AT$_2$ receptor family members include, but are not limited to, murine and human homologs.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

"Antigenic or immunogenic activity" refers to the ability of a polypeptide, fragment, variant or derivative according to the invention to produce an antigenic or immunogenic response in an animal, suitably a mammal, to which it is administered, wherein the response includes the production of elements which specifically bind the polypeptide or fragment thereof.

As used herein, "aromatic" or "aryl" is intended to mean, unless otherwise indicated, any stable monocyclic or bicyclic carbon ring of up to 7 atoms in each ring, wherein at least one ring is aromatic. Examples of such aryl elements include, but are not limited to, phenyl, naphthyl, tetrahydronaphthyl, indanyl, biphenyl, phenanthryl, anthryl or acenaphthyl.

"Aralkyl" means alkyl as defined above which is substituted with an aryl group as defined above, e.g., —CH$_2$phenyl, —(CH$_2$)$_2$phenyl, —(CH$_2$)$_3$phenyl, —H$_2$CH(CH$_3$)CH$_2$phenyl, and the like and derivatives thereof.

As used herein, "arylene" refers to a monocyclic or polycyclic, preferably monocyclic, bivalent aromatic group, preferably having from 3 to about 20 carbon atoms and at least one aromatic ring, more preferably 3 to 12 carbons, even more preferably lower arylene. The arylene group is optionally substituted with one or more "alkyl group substituents." There may be optionally inserted around the arylene group one or more oxygen, sulfur or substituted or unsubstituted nitrogen atoms, where the nitrogen substituent is alkyl as previously described. Exemplary arylene groups include 1,2-, 1,3- and 1,4-phenylene. The term "lower arylene" refers to arylene groups having 5 or 6 carbons. Preferred arylene groups are lower arylene.

As used herein, "arylidene" refers to an unsaturated cyclic bivalent group where both points of attachment are on the same atom of the ring. Exemplary arylidene groups include, but are not limited to, quinone methide moieties that have the formula:

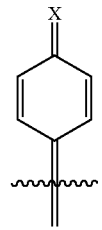

where X is O, S or NR9. "Heteroarylidene" groups are arylidene groups where one or two, preferably two, of the atoms in the ring are heteroatoms, such as, but not limited to, O, S and N.

As used herein, the term "biological activity" means any observable effect flowing from the interaction between an AT$_2$ receptor polypeptide and a ligand. Representative, but non-limiting, examples of biological activity in the context of the present invention include association of an AT$_2$ receptor with a ligand, including an endogenous ligand such as angiotensin II or an AT$_2$ receptor antagonist. The term "biological activity" also encompasses both the inhibition and the induction of the expression of an AT$_2$ receptor polypeptide. Further, the term "biological activity" encompasses any and all effects flowing from the binding of a ligand by an AT$_2$ receptor polypeptide.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

The term "cycloalkenyl" means a monocyclic unsaturated hydrocarbon group and may have a specified number of carbon atoms. For example, "cycloalkenyl" includes but is not limited to, cyclobutenyl, cyclopentenyl, methylcyclopentenyl, cyclohexenyl and cyclohexadienyl.

Unless otherwise indicated, the term "cycloalkyl" or "aliphatic ring" means a monocyclic saturated aliphatic hydrocarbon group and may have a specified number of carbon atoms. For example, "cycloalkyl" includes, but is not limited to, cyclopropyl, methyl-cyclopropyl, 2,2-dimethyl-cyclobutyl, 2-ethyl-cyclopentyl, cyclohexyl.

By "derivative," as applied to peptides and polypeptides, refers to a peptide or polypeptide that has been derived from the basic sequence by modification, for example by conjugation or complexing with other chemical moieties or by post-translational modification techniques as would be understood in the art. The term "derivative" also includes within its scope alterations that have been made to a parent sequence including additions or deletions that provide for functional equivalent molecules.

By "effective amount", in the context of treating or preventing a condition is meant the administration of that amount of active to an individual in need of such treatment or prophylaxis, either in a single dose or as part of a series, that is effective for the prevention of incurring a symptom, holding in check such symptoms, and/or treating existing symptoms, of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

The term "gene" as used herein refers to any and all discrete coding regions of the cell's genome, as well as associated non-coding and regulatory regions. The gene is also intended to mean the open reading frame encoding specific polypeptides, introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. The DNA sequences may be cDNA or genomic DNA or a fragment thereof. The gene may be introduced into an appropriate vector for extrachromosomal maintenance or for integration into the host.

As appreciated by those of skill in the art, "halo" or "halogen" as used herein is intended to include chloro, fluoro, bromo and iodo.

"Heteroaralkyl" group means alkyl as defined above which is substituted with a heteroaryl group, e.g., —CH$_2$pyridinyl, —(CH$_2$)$_2$pyrimidinyl, —(CH$_2$)$_3$imidazolyl, and the like, and derivatives thereof.

The term "heteroaryl" or "heteroaromatic," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl.

Further examples of "heteroaryl" and "heterocyclyl" include, but are not limited to, the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazoyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

As used herein, "heteroarylene," unless otherwise indicated, refers to a bivalent monocyclic or multicyclic ring system, preferably of about 3 to about 15 members where one or more, more preferably 1 to 3 of the atoms in the ring system is a heteroatom, that is, an element other than carbon, for example, nitrogen, oxygen and sulfur atoms. The heteroarylene group may be optionally substituted with one or more, preferably 1 to 3, aryl group substituents. Exemplary heteroarylene groups include, for example, 1,4-imidazolylene.

The term "heterocycle", "heteroaliphatic" or "heterocyclyl" as used herein is intended to mean a 5- to 10-membered nonaromatic heterocycle containing from 1 to 4 heteroatoms selected from the group consisting of O, N and S, and includes bicyclic groups.

"Heterocyclylalkyl" group means alkyl as defined above which is substituted with a heterocycle group, e.g., —CH$_2$pyrrolidin-1-yl, —(CH$_2$)$_2$piperidin-1-yl, and the like, and derivatives thereof.

"Hybridization" is used herein to denote the pairing of complementary nucleotide sequences to produce a DNA-DNA hybrid or a DNA-RNA hybrid. Complementary base sequences are those sequences that are related by the base-pairing rules. In DNA, A pairs with T and C pairs with G. In RNA U pairs with A and C pairs with G. In this regard, the terms "match" and "mismatch" as used herein refer to the hybridization potential of paired nucleotides in complementary nucleic acid strands. Matched nucleotides hybridize efficiently, such as the classical A-T and G-C base pair mentioned above. Mismatches are other combinations of nucleotides that do not hybridize efficiently.

The term "hydrocarbyl" as used herein includes any radical containing carbon and hydrogen including saturated, unsaturated, aromatic, straight or branched chain or cyclic including polycyclic groups. Hydrocarbyl includes but is not limited to $C_1$-$C_8$alkyl, $C_2$-$C_8$alkenyl, $C_2$-$C_8$alkynyl, $C_3$-$C_{10}$cycloalkyl, aryl such as phenyl and naphthyl, Ar ($C_1$-$C_8$)alkyl such as benzyl, any of which may be optionally substituted.

By "hyperalgesia" is meant an increased response to a stimulus that is normally painful.

Reference herein to "immuno-interactive" includes reference to any interaction, reaction, or other form of association between molecules and in particular where one of the molecules is, or mimics, a component of the immune system.

As used herein "inflammatory pain" refers to pain induced by inflammation. Such types of pain may be acute or chronic and can be due to any number of conditions characterized by inflammation including, without limitation, burns including chemical, frictional or thermal burns, autoimmune diseases such as rheumatoid arthritis, osteoarthritis and colitis, as well as other inflammatory diseases including carditis, dermatitis, myositis, neuritis and collagen vascular diseases.

The term "oligonucleotide" as used herein refers to a polymer composed of a multiplicity of nucleotide residues (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotide residues and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule can vary depending on the particular application. An oligonucleotide is typically rather short in length, generally from about 10 to 30 nucleotide residues, but the term can refer to molecules of any length, although the term "polynucleotide" or "nucleic acid" is typically used for large oligonucleotides.

By "operably linked" is meant that transcriptional and translational regulatory polynucleotides are positioned relative to a polypeptide-encoding polynucleotide in such a manner that the polynucleotide is transcribed and the polypeptide is translated.

The term "pain" as used herein is given its broadest sense and includes an unpleasant sensory and emotional experience associated with actual or potential tissue damage, or described in terms of such damage and includes the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (Dorland's Illustrated Medical Dictionary, 28$^{th}$ Edition, W.B. Saunders Company, Philadelphia, Pa.). The present invention is particularly concerned with the alleviation of inflammatory pain. The goal of treatment of pain is to reduce the degree of severity of pain perceived by a treatment subject.

By "pharmaceutically acceptable carrier" is meant a solid or liquid filler, diluent or encapsulating substance that may be safely used in topical, local or systemic administration.

The terms "pharmaceutically compatible salt" and "pharmaceutically acceptable salt" are used interchangeably herein to refer to a salt which is toxicologically safe for human and animal administration. This salt may be selected from a group including hydrochlorides, hydrobromides, hydroiodides, sulfates, bisulfates, nitrates, citrates, tartrates, bitartrates, phosphates, malates, maleates, napsylates, fumarates, succinates, acetates, terephthalates, pamoates and pectinates. Pharmaceutically acceptable salts include both the metallic (inorganic) salts and organic salts; a non-exhaustive list of which is given in Remington's Pharmaceutical Sciences 17th Edition, pg. 1418 (1985). It is well known to one skilled in the art that an appropriate salt form is chosen based on physical and chemical stability, flowability, hydroscopicity and solubility.

"Phenylalkyl" means alkyl as defined above which is substituted with phenyl, e.g., —$CH_2$phenyl, —$(CH_2)_2$phenyl, —$(CH_2)_3$phenyl, $CH_3CH(CH_3)CH_2$phenyl, and the like and derivatives thereof. Phenylalkyl is a subset of the aralkyl group.

The terms "polynucleotide variant" and "variant" refer to polynucleotides displaying substantial sequence identity with a reference polynucleotide sequence or polynucleotides that hybridize with a reference sequence under stringent conditions as known in the art (see for example Sambrook et al., Molecular Cloning. A Laboratory Manual", Cold Spring Harbor Press, 1989). These terms also encompass polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains a biological function or activity of the reference polynucleotide. The terms "polynucleotide variant" and "variant" also include naturally-occurring allelic variants.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally occurring amino acid polymers.

The term "polypeptide variant" refers to polypeptides in which one or more amino acids have been replaced by different amino acids. It is well understood in the art that some amino acids may be changed to others with broadly similar properties without changing the nature of the activity of the polypeptide (conservative substitutions) as described hereinafter. These terms also encompass polypeptides in which one or more amino acids have been added or deleted, or replaced with different amino acids.

The term "prodrug" is used in its broadest sense and encompasses those compounds that are converted in vivo to an $AT_2$ receptor antagonist according to the invention. Such compounds would readily occur to those of skill in the art, and include, for example, compounds where a free hydroxy group is converted into an ester derivative.

As used herein, "pseudohalides" are groups that behave substantially similar to halides. Such groups can be used in the same manner and treated in the same manner as halides (X, in which X is a halogen, such as Cl or Br). Pseudohalides include, but are not limited to cyanide, cyanate, thiocyanate, selenocyanate, trifluoromethyl and azide.

The terms "subject" or "individual" or "patient", used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, primates, avians, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes). A preferred subject is a human in need of treatment or prophylaxis of inflammatory pain. However, it will be understood that the aforementioned terms do not imply that symptoms are present.

"Stereoisomers" refer to any two or more isomers that have the same molecular constitution and differ only in the three dimensional arrangement of their atomic groupings in space. Stereoisomers may be diastereoisomers or enantiomers. It will be recognized that the compounds described herein may possess asymmetric centers and are therefore capable of existing in more than one stereoisomeric form. The invention thus also relates to compounds in substantially pure isomeric form at one or more asymmetric centers e.g., greater than about 90% ee, such as about 95% or 97% ee or greater than 99% ee, as well as mixtures, including racemic mixtures, thereof. Such isomers may be naturally occurring or may be prepared by asymmetric synthesis, for example using chiral intermediates, or by chiral resolution.

The term "substituted" and variants such as "optionally substituted" as used herein, unless otherwise indicated, mean that a substituent may be further substituted by one or more additional substituents, which may be optional or otherwise. Examples of additional substituents include $C_1$-$C_{10}$alkyl, $C_3$-$C_{10}$alkenyl, $C_3$-$C_{10}$alkynyl, aryl, —($C_1$-$C_4$alkyl)aryl, heterocyclyl, heteroaryl, $C_3$-$C_7$-cycloalkyl, $C_1$-$C_4$-perfluoroalkyl, —OH, —SH, —HN$_2$, nitrile, $C_1$-$C_{10}$-alkoxy, halo$C_{1-4}$alkyl, hydroxy$C_{1-4}$alkyl, $C_1$-$C_{10}$-alkylthio, —CF$_3$, halo (F, Cl, Br, I), —NO$_2$, —CO$_2$R$^{23}$, —NH$_2$, $C_1$-$C_4$alkylamino, $C_1$-$C_4$dialkylamino, arylamino, diarylamino, aryl$C_{1-4}$alkylamino, aryl$C_{1-4}$dialkylamino, aryloxy, aryl$C_{1-4}$alkyloxy, formyl, $C_{1-10}$alkylcarbonyl and $C_{1-10}$alkoxycarbonyl, —PO$_3$H$_2$, —CO$_2$H, —CONHSO$_2$R$^{21}$, —CONHSO$_2$NHR$^{20}$, —NHCONHSO$_2$ R$^{21}$, —NHSO$_2$R$^{21}$, —NHSO$_2$NHCOR$^{21}$, —SO$_2$NHR$^{20}$, —SO$_2$NHCOR$^{21}$, —SO$_2$NHCONHR$^{20}$, —SO$_2$NHCO$_2$R$^{21}$, tetrazolyl, —CHO, —CONH$_2$, —NHCHO, —CO—($C_1$-$C_6$ perfluoroalkyl), —S(O)$_r$—($C_1$-$C_6$ perfluoroalkyl), wherein R$^{20}$ is H, $C_1$-$C_5$-alkyl, aryl, —($C_1$-$C_4$-alkyl)-aryl, heteroaryl; R$^{21}$ is aryl, $C_3$-$C_7$-cycloalkyl, $C_1$-$C_4$-perfluoroalkyl, $C_1$-$C_4$alkyl, optionally substituted with a substituent selected from the group consisting of aryl, heteroaryl, —OH, —SH, $C_1$-$C_4$-alkyl, $C_1$-$C_4$alkoxy, $C_1$-$C_4$alkylthio, —CF$_3$, halo, —NO$_2$, —CO$_2$R$^{23}$, —NH$_2$, $C_1$-$C_4$-alkylamino, $C_1$-$C_4$-dialkylamino, —PO$_3$H$_2$, or heteroaryl; and R$^{22}$ is selected from $C_1$-$C_6$-alkyl, $C_3$-$C_6$-cycloalkyl, aryl, —($C_1$-$C_5$-alkyl)-aryl, or heteroaryl.

By "vector" is meant a polynucleotide molecule, preferably a DNA molecule derived, for example, from a plasmid, bacteriophage, yeast or virus, into which a polynucleotide can be inserted or cloned. A vector preferably contains one or more unique restriction sites and can be capable of autonomous replication in a defined host cell including a target cell or tissue or a progenitor cell or tissue thereof, or be integrable with the genome of the defined host such that the cloned sequence is reproducible. Accordingly, the vector can be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably a viral or viral-derived vector, which is operably functional in animal and preferably mammalian cells. Such vector may be derived from a poxvirus, an adenovirus or yeast. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 (Geneticin®) and the hph gene which confers resistance to the antibiotic hygromycin B.

2. Abbreviations

The following abbreviations are used throughout the application:
d=day
h=hour
s=seconds
i.v.=intravenous
i.p.=intraperitoneal
s.c.=subcutaneous 3. Compositions and Methods for the Treatment or Prophylaxis of Inflammatory Pain The present invention arises from the unexpected discovery that AT$_2$ receptor antagonists are effective in the prevention or attenuation of the symptoms of inflammatory pain. These discoveries are based on pre-clinical data which show that administration of AT$_2$ receptor antagonists to rats with unilateral inflammation of the hindpaw causes alleviation of inflammatory pain. Accordingly, the present invention provides methods for treating or preventing inflammatory pain, wherein the methods generally comprise administering to an individual having, or at risk of developing, inflammatory pain, an effective amount of an AT$_2$ receptor antagonist, which is suitably in the form of a pharmaceutical composition. In accordance with the present invention, the AT$_2$ receptor antagonist can act to prevent or attenuate one or more symptoms associated with inflammatory pain including, but not limited to, swelling, redness, hyperalgesia (e.g., mechanical and thermal hyperalgesia), and allodynia. The inflammatory pain may be acute and/or chronic.

There are many possible causes of inflammatory pain and it will be understood that the present invention contemplates the treatment or prevention of any inflammatory pain regardless of the cause. For example, in some embodiments, the inflammatory pain results from an infection including but not limited to viral, bacterial or fungal infections. In other embodiments, the inflammatory pain results from a tissue burn, including a burn of the cutaneous tissue (e.g., caused by a thermal, chemical, or radiation stimulus) or a sunburn. In still other embodiments, the inflammatory pain results from an autoimmune disease including but not restricted to rheumatoid arthritis, inflammatory arthritis, psoriasis, ankylosing spondylitis, osteoarthritis, colitis and irritable bowel disease. In still other embodiments, the inflammatory pain results from an inflammatory condition of the skin, muscle, or joints (e.g., myocardial infarction, angina, ischemic or thrombotic cardiovascular disease, peripheral vascular occlusive disease, or peripheral arterial occlusive disease, carditis, dermatitis, myositis, neuritis and collagen vascular diseases). In still other embodiments, the inflammatory pain results from a cancer. In further embodiments, the inflammatory pain results from a traumatic injury or surgery.

The $AT_2$ receptor antagonist includes and encompasses any active compound that binds to the $AT_2$ receptor subtype and that suitably inhibits the effect of angiotensin II signaling through this receptor, including pharmaceutical compatible salts of the active compound. This category includes compounds having differing structural features. For example, in some embodiments, the $AT_2$ receptor antagonist is selected from the compounds listed in U.S. Pat. No. 5,789,415 and especially in the compound claims of this patent. In illustrative examples of this type, the $AT_2$ receptor antagonist is selected from compounds having the formula (Ia):

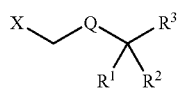

(Ia)

or their pharmaceutically compatible salts, wherein:

Q is naphthyl, a 5 to 7 member heterocycle having from 1 to 3 atoms independently selected from nitrogen, oxygen and sulfur, or an 8 to 11 member heterobicycle having from 1 to 4 atoms selected from nitrogen, oxygen and sulfur, said heterocycle or heterobicycle being saturated, partially saturated or unsaturated and said naphthyl, heterocycle or heterobicycle optionally substituted with 1 to 4 $W^1$ substituents;

each $W^1$ substituent is independently selected from halo, hydroxy, nitro, cyano, $C_1$ to $C_8$ alkyl, $C_3$ to $C_7$ cycloalkyl, $C_1$ to $C_7$ alkoxy, amino, $C_1$ to $C_7$ alkylamino, di($C_1$ to $C_7$ alkyl)amino, $C_1$ to $C_7$ alkylthio, $C_1$ to $C_7$ alkylsulfinyl, $C_1$ to $C_7$ alkylsulfonyl, —CONRR, —COOR and phenyl, said alkyl, cycloalkyl, alkoxy, alkylamino, dialkylamino, alkylthio, alkylsulfinyl and alkylsulfonyl optionally substituted with 1 or more $W^2$ substituents, and said phenyl optionally substituted with 1 or more $W^3$ substituents;

each R is independently hydrogen or $C_1$ to $C_8$ alkyl, said alkyl optionally substituted with 1 or more $W^2$ substituents;

each $W^2$ substituent is independently selected from halo, hydroxy, oxo, $C_3$ to $C_7$ cycloalkyl, $C_1$ to $C_7$ alkoxy, acyloxy, phenyl and 5 to 7 member heterocycle having 1 to 3 atoms selected from nitrogen, oxygen and sulfur, said phenyl and heterocycle optionally substituted with 1 or more $W^3$ substituents;

each $W^3$ substituent is independently selected from halo, hydroxy, nitro, $C_3$ to $C_7$ cycloalkyl, $C_1$ to $C_7$ alkoxy, amino, $C_1$ to $C_7$ alkylamino, di($C_1$ to $C_7$ alkyl)amino, $C_1$ to $C_7$ alkylthio, $C_1$ to $C_7$ alkylsulfinyl and $C_1$ to $C_7$ alkylsulfonyl;

$R^1$ and $R^2$, when taken separately, are each independently selected from hydrogen, hydroxy, $C_1$ to $C_{10}$ alkyl, $C_1$ to $C_7$ alkylthio, $C_1$ to $C_7$ alkylsulfinyl, $C_1$ to $C_7$ alkylsulfonyl, phenyl and 5 to 7 member heterocycle or 8 to 11 member heterobicycle, having 1 to 3 atoms selected from nitrogen, oxygen and sulfur, said alkyl, alkylthio, alkylsulfinyl and alkylsulfonyl optionally substituted with 1 or more $W^4$ substituents, said phenyl and said heterocycle and heterobicycle optionally substituted with 1 to 5 $W^3$ substituents, wherein the $W^3$ substituents are as defined above, and said heterocycle being saturated, partially saturated or unsaturated, provided that $R^1$ and $R^2$ are not both hydroxy;

$R^1$ and $R^2$, when taken together with the carbon atom to which they are attached, form a $C_3$ to $C_7$ carbocyclic, $C_7$ to $C_{11}$ carbobicyclic, 3 to 7 member heterocyclic group having from 1 to 3 atoms independently selected from nitrogen, oxygen and sulfur, or a 7 to 11 member heterobicyclic group having from 1 to 4 atoms independently selected from nitrogen, oxygen and sulfur, said carbocyclic, carbobicyclic, heterocyclic or heterobicyclic group being saturated, partially saturated or unsaturated and optionally substituted with 1 or more $W^5$ substituents;

each $W^4$ substituent is independently selected from halo, $C_3$ to $C_8$ cycloalkyl, phenyl and 5 to 7 member heterocycle having 1 to 3 atoms selected from nitrogen, oxygen and sulfur, said phenyl and heterocycle optionally substituted with 1 or more substituents independently selected from halo, hydroxy, nitro, $C_1$ to $C_{10}$ alkyl, $C_3$ to $C_7$ cycloalkyl, $C_1$ to $C_7$ alkoxy, amino, $C_1$ to $C_7$ alkylamino and di($C_1$ to $C_7$ alkyl)amino;

each $W^5$ substituent is independently selected from halo, hydroxy, nitro, cyano, oxo, $C_1$ to $C_8$ alkyl, $C_3$ to $C_7$ cycloalkyl, $C_1$ to $C_7$ alkoxy, amino, $C_1$ to $C_7$ alkylamino, di($C_1$ to $C_7$ alkyl)amino, $C_1$ to $C_7$ alkylthio, $C_1$ to $C_7$ alkylsulfinyl, $C_1$ to $C_7$ alkylsulfonyl, —CONRR, —COOR and phenyl, said alkyl, cycloalkyl, alkoxy, alkylamino, dialkylamino, alkylthio, alkylsulfinyl and alkylsulfonyl groups optionally substituted with 1 or more $W^2$ substituents, and said phenyl optionally substituted with 1 or more $W^3$ substituents, wherein the $W^3$ substituents are as defined above;

$R^3$ is —$(CH_2)_nCOR^4$, tetrazolyl, $C_1$ to $C_5$ alkyltetrazolyl, triazolyl, $C_1$ to $C_5$ alkyltriazolyl, —$(CH_2)_nCH_2OH$, —$SO_2R^4$, —$SO_2NR^5R^6$ or —$NHSO_2R^7$;

$R^4$ is hydrogen, hydroxy, —$NHSO_2R^7$, $C_1$ to $C_{10}$ alkoxy, $C_1$ to $C_7$ alkylthio, —$NR^5R^6$, —$NHSO_2 R^7$ or —OY, said alkoxy and alkylthio groups optionally substituted with 1 or more $W^6$ substituents;

n is an integer from 0 to 5;

Y is a pharmaceutically acceptable cation or a group hydrolyzable under physiological conditions;

$R^5$ and $R^6$, when taken separately, are each independently hydrogen, hydroxy, cyano, $C_1$ to $C_{10}$ alkyl, $C_1$ to $C_8$ alkoxy, —COR, —CONRR, —COOR, phenoxy, —CO($C_6H_5$) or 5 to 6 member heterocycle having 1 to 4 atoms selected from nitrogen, oxygen and sulfur, wherein R is as defined above, said alkyl optionally substituted with 1 or more $W^3$ substituents, wherein the $W^3$ substituents are as defined above, said —CO($C_6H_5$) optionally substituted with 1 to 3 $W^6$ substituents and said heterocycle optionally substituted with 1 or more $W^5$ substituents, wherein the $W^5$ substituents are as defined above;

$R^5$ and $R^6$, when taken together with the nitrogen atom to which they are attached, form a 3 to 7 member ring having 1 to 3 nitrogen atoms and from 0 to 3 atoms selected from oxygen and sulfur, said ring being saturated, partially saturated or unsaturated and optionally substituted with 1 or more $W^1$ substituents, wherein the $W^1$ substituents are as defined above;

R⁷ is $C_1$ to $C_{10}$ alkyl or phenyl, said alkyl optionally substituted with 1 or more $W^6$ substituents, and said phenyl optionally substituted with 1 or more $W^3$ substituents, wherein the $W^3$ substituents are as defined above;

X is an azacyclic group of the formula:

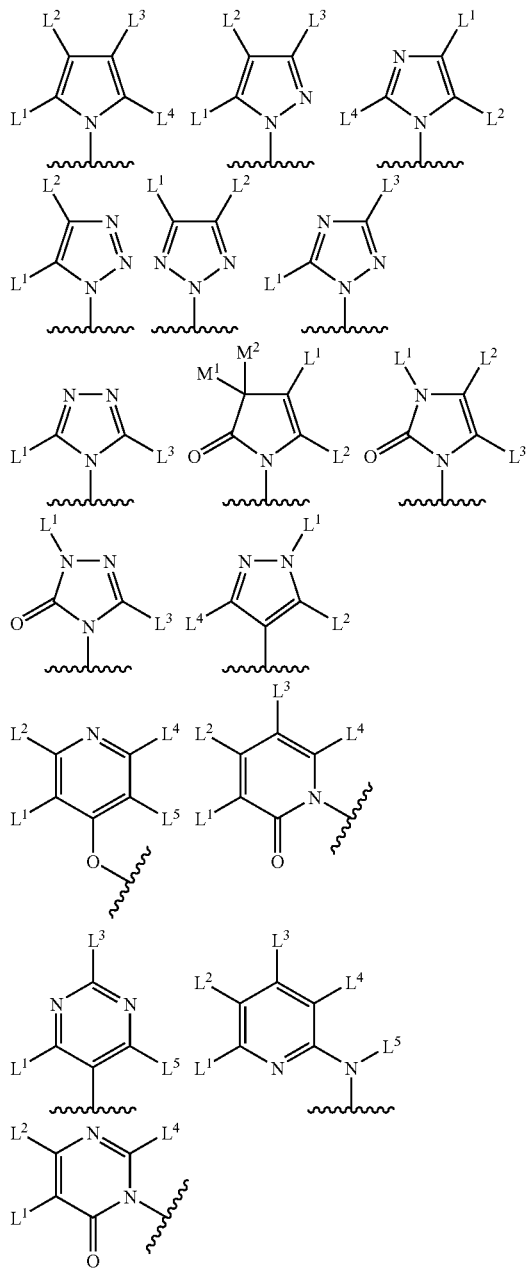

$L^1$, $L^2$, $L^3$, $L^4$ and $L^5$, when taken separately, are independently hydrogen, halo, nitro, $C_1$ to $C_6$ alkyl, $C_3$ to $C_7$ cycloalkyl, polyfluoro-$C_1$ to $C_4$ alkyl, aryl, heteroaryl, tetrazol-5-yl, —COR⁸, —CO₂R⁸, —CONHSO₂R⁹, —CONR¹⁰R¹⁰, —CONH(tetrazol-5-yl), —OR⁹, —OCONR⁹R¹¹, —NR⁸R⁹, —NHCOR⁹, —NHCO₂R⁹, —NHCONR⁸R⁹, —NHSO₂R⁹, —NHSO₂NR⁹R¹¹, —NHSO₂-polyfluorophenyl, —SR⁹, —SOR⁹, —SO₂R⁹, —SO²NHCN, —SO₂NR¹¹R¹², —SO₂NHCOR⁹, —SO₂NH-heteroaryl, —PO(OR⁸)₂ or —PO(OR⁸)R¹¹, said alkyl, cycloalkyl, aryl and heteroaryl groups optionally substituted with 1 or more substituents selected from hydroxy, halo, $C_1$ to $C_4$ perfluoroalkyl, $C_1$ to $C_4$ alkoxy, aryl, heteroaryl, guanidino, morpholino, tetrazol-5-yl, —COR⁸, —CO₂R⁸, —CONHSO₂R⁹, —CONR⁸R⁸, —O—COR⁸, —NR⁸R⁸, —NR¹²COOR⁹, —N($C_1$ to $C_6$ alkyl)piperazine, —SR⁹, —SOR⁹, —SO₂ R⁹, —SO₂ NR⁸CN, —SO₂NR⁸COR⁹, —SO₂NR⁸-heteroaryl, —PO(OR⁸)₂ and —PO(OR⁸)R¹³;

$L^1$ and $L^2$, $L^2$ and $L^3$, $L^3$ and $L^4$ or $L^4$ and $L^3$, when taken together with the azacyclic group to which they are attached, form a fused 8 to 11 member azabicyclic system having 1 to 5 nitrogen atoms and 0 to 3 atoms selected from oxygen and sulfur, said azabicyclic system optionally substituted with 1 to 3 $W^6$ substituents;

each $W^6$ substituent is independently halo, nitro, cyano, $C_1$ to $C_6$ alkyl, $C_3$ to $C_7$ cycloalkyl, polyfluoro-$C_1$ to $C_4$ alkyl, aryl, heteroaryl, tetrazol-5-yl, —COR⁸, —CO₂R⁸, —CONR⁸SO₂R⁹, —CONR⁹R¹⁰, —CONR⁸(tetrazol-5-yl), —OR⁹, —OCONR⁹R¹¹, —NR⁸R⁹, —NR⁸COR⁹, —NR⁸CO₂R⁹, —NR⁸CONR⁸R⁹, —NR⁸SO₂R⁹, —NR⁸SO₂NR₉R¹¹, —NR⁸SO₂-polyfluorophenyl, —SR⁹, —SOR⁹, —SO₂R⁹, —SO₂ NR₈CN, —SO₂NR⁹R¹², —SO NR⁸COR⁹, —SO₂NR⁸-heteroaryl, —PO(OR⁸)₂ or —PO(OR⁸)R¹¹, said alkyl, cycloalkyl, aryl and heteroaryl groups optionally substituted with 1 or more substituents selected from hydroxy, halo, $C_1$ to $C_4$ perfluoroalkyl, $C_1$ to $C_4$ alkoxy, aryl, heteroaryl, guanidino, morpholino, tetrazol-5-yl, —COR⁸, —CO₂R⁸, —CONR⁸SO₂R⁹, —CONR⁸R⁹, —O—COR⁸, —NR⁸R⁹, —NR¹²COOR⁹, —N($C_1$ to $C_6$ alkyl)piperazine, —SR⁹, —SOR⁹, —SO₂R⁹, —SO₂ NR⁸CN, —SO₂NR⁸COR⁹, —SO₂NR⁸-heteroaryl, —PO(OR⁸)₂ and —PO(OR⁸)R¹³;

each R⁸ is independently hydrogen, $C_1$ to $C_6$ alkyl, $C_3$ to $C_7$ cycloalkyl, aryl, heteroaryl or aryl($C_1$ to $C_6$)alkyl;

each R⁹ is independently hydrogen, $C_1$ to $C_{10}$ alkyl, $C_3$ to $C_7$ cycloalkyl, aryl, heteroaryl or polyfluoro($C_1$ to $C_4$)alkyl, said alkyl and cycloalkyl optionally substituted with 1 or more substituents selected from halo, hydroxy, nitro, $C_1$ to $C_4$ alkoxy, $C_1$ to $C_4$ alkylthio, —CO₂R¹², amino, $C_1$ to $C_4$ alkylamino, di($C_1$ to $C_4$)alkylamino, aryl, heteroaryl, —SH, —PO₃H₂, —P(O)(OH)(O—$C_1$ to $C_4$ alkyl), P(O)(OR⁸)(R¹¹) or P(O)(OR¹⁴)(R¹⁵);

each R¹⁰ is independently hydrogen, $C_1$ to $C_5$ alkyl, aryl or —CH₂-aryl;

each $R_{11}$ is independently hydrogen, $C_1$ to $C_5$ alkyl, $C_3$ to $C_7$ cycloalkyl, aryl or —CH₂-aryl;

each R¹² is hydrogen or $C_1$ to $C_4$ alkyl;

each R¹³ is independently hydrogen, $C_1$ to $C_5$ alkyl, $C_2$ to $C_4$ alkenyl, $C_1$ to $C_4$ alkoxy($C_1$ to $C_4$)alkyl or benzyl, said benzyl optionally substituted with 1 or more substituents independently selected from hydroxy, amino, nitro and methoxy;

$R^{14}$ and $R^{15}$ are taken together and form a 5 to 7 member ring having 1 to 3 atoms independently selected from nitrogen, oxygen and sulfur;

$M^1$ and $M^2$ are taken together and are —$(CH_2)_m$; and m is an integer from 3 to 7.

Preferred compounds are those of formula (I) wherein:

X is

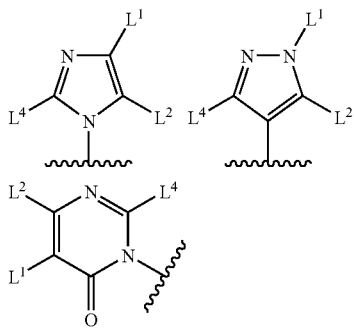

$L^1$, $L^2$ and $L^4$ are as defined above;

Q is thiophene, pyridine, pyrimidine, naphthyl, benzofuran or any of the foregoing substituted with 1 or 2 $W^1$ substituents; $R^1$ and $R^2$ are taken together as defined above;

$R^3$ is —$(CH_2)_n COR^4$; n is 0 or 1; $R^4$ is hydrogen, hydroxy or —OY;

Y is a pharmaceutically acceptable cation or a group hydrolyzable under physiological conditions; and each $W^1$ is independently halo, hydroxy, $C_1$ to $C_8$ alkyl, $C_3$ to $C_7$ cycloalkyl, $C_1$ to $C_7$ alkoxy, amino, $C_1$ to $C_7$ alkylamino, di($C_1$ to $C_7$ alkyl)amino, —CONRR or —COOR, wherein R is as defined above.

Particularly preferred are those compounds wherein X, Q, $R^3$, $R^4$, n and Y are as defined immediately above and wherein:

$R^1$ and $R^2$ are taken together and form a $C_5$ to $C_6$ carbocyclic, $C_8$ to $C_{10}$ carbobicyclic or 5 to 7 member heterocyclic group having 1 or 2 atoms independently selected from nitrogen, oxygen and sulfur, said carbocyclic, carbobicyclic or heterocyclic group being saturated, partially saturated or unsaturated;

$L^1$ and $L^2$, when taken separately, are each independently hydrogen, halo, $C_1$ to $C_6$ alkyl, $C_3$ to $C_7$ cycloalkyl, polyfluoro-$C_1$ to $C_4$ alkyl or —$CO_2R^8$;

$L^1$ and $L^2$, when taken together with the azacyclic group to which they are attached, form a fused 8 to 10 member azabicyclic system having 2 to 4 nitrogen atoms, said azabicyclic system optionally substituted with 1 to 3 $W^6$ substituents;

$L^4$ is $C_1$ to $C_4$ alkyl, $C_3$ to $C_5$ cycloalkyl or $C_1$ to $C_3$ alkoxy;

$R^8$ is hydrogen, $C_1$ to $C_6$ alkyl or $C_3$ to $C_7$ cycloalkyl; and each $W^6$ is independently halo, $C_1$ to $C_6$ alkyl, $C_3$ to $C_7$ cycloalkyl, polyfluoro-$C_1$ to $C_4$ alkyl, —$CO_2R^8$, amino, $C_1$ to $C_6$ alkylamino, di($C_1$ to $C_6$)alkylamino, acylamino or diacylamino.

Among the particularly preferred compounds defined above are those having the structure:

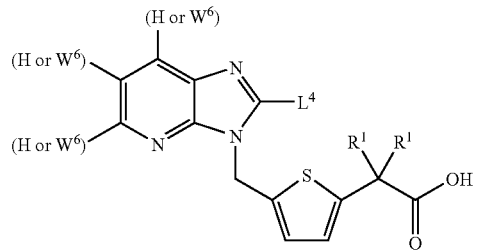

wherein:

$L^4$ is $C_1$ to $C_4$ alkyl or $C_3$ to $C_5$ cycloalkyl;

each $W^6$ is independently $C_1$ to $C_6$ alkyl, amino, $C_1$ to $C_6$ alkylamino, di($C_1$ to $C_6$)alkylamino, acylamino or diacylamino; and $R^1$ and $R^2$ are taken together and form cyclopentane, cyclohexane, cyclopentene, tetrahydropyran or indan, for example:

1-[5-(2-ethyl-5,7-dimethylimidazo[4,5-b]pyridin-3-ylmethyl)thiophen-2-yl]-cyclopent-3-ene carboxylic acid;

1-[5-(5,7-dimethyl-2-propylimidazo[4,5-b]pyridin-3-ylmethyl)thiophen-2-yl]cyclopent-3-ene carboxylic acid;

1-[5-(2-cyclopropyl-5,7-dimethylimidazo[4,5-b]pyridin-3-ylmethyl)thiophen-2-yl]cyclopent-3-ene carboxylic acid;

1-[5-(2-cyclopropyl-5,7-dimethylimidazo[4,5-b]pyridin-3-ylmethyl)thiophen-2-yl]cyclopentane carboxylic acid;

4-[5-(2-ethyl-5,7-dimethylimidazo[4,5-b]pyridin-3-ylmethyl)thiophen-2-yl]tetrahydropyran-4-carboxylic acid;

2-[5-(2-ethyl-5,7-dimethylimidazo[4,5-b]pyridin-3-ylmethyl)thiophen-2-yl]indan-2-carboxylic acid;

2-[5-(2-cyclopropyl-5,7-dimethylimidazo[4,5-b]pyridin-3-ylmethyl)thiophen-2-yl]indan-2-carboxylic acid;

1-[5-(2-ethyl-5,7-dimethylimidazo[4,5-b]pyridin-3-ylmethyl)thiophen-2-yl]cyclohexane carboxylic acid; and 1-[5-(2-cyclopropyl-5,7-dimethylimidazo[4,5-b]pyridin-3-ylmethyl)thiophen-2-yl]cyclohexane carboxylic acid.

Also among the particularly preferred compounds defined above are those having the structure

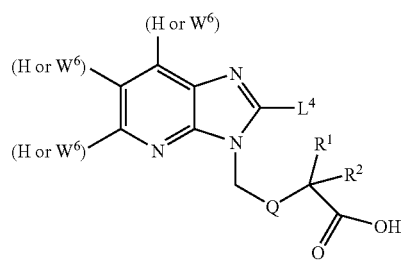

wherein:

Q is

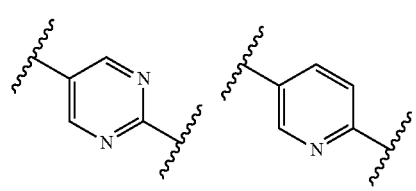

-continued

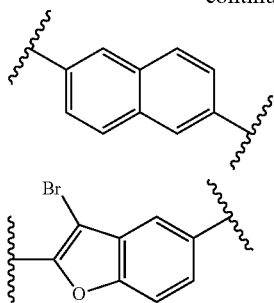

L⁴ is $C_1$ to $C_4$ alkyl or $C_3$ to $C_5$ cycloalkyl; and
R¹ and R² are taken together and are —CH₂CH₂CH₂CH₂— or —CH₂CH=CHCH₂—, for example:
1-[5-(2-ethyl-5,7-dimethylimidaz[4,5-b]pyridin-3-ylm-ethyl)pyridin-2-yl]cyclopentane carboxylic acid;
1-[5-(2-cyclopropyl-5,7-dimethylimidazo[4,5-b]pyridin-3-ylmethyl)pyridin-2-yl]cyclopentane carboxylic acid;
1-[2-(2-ethyl-5,7-dimethylimidazo[4,5-b]pyridin-3-ylm-ethyl)pyrimidin-5-yl]cyclopent-3-ene carboxylic acid;
1-[2-(2-cyclopropyl-5,7-dimethylimidazo[4,5-b]pyridin-3-ylmethyl)pyrimidin-5-yl]cyclopent-3-ene carboxylic acid;
1-[6-(2-ethyl-5,7-dimethylimidazo[4,5-b]pyridin-3-ylm-ethyl)naphthalen-2-yl]cyclopent-3-ene carboxylic acid; and
1-[3-bromo-5-(2-ethyl-5,7-dimethylimidazo[4,5-b]pyridin-3-ylmethyl)benzofuran-2-yl]cyclopentane carboxylic acid.

Also among the particularly preferred compounds defined above are those having the structure

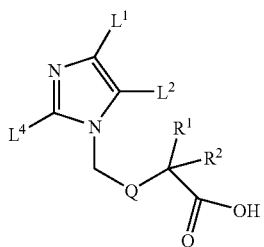

wherein:
Q is

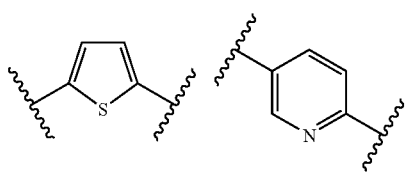 [SMILES: *c1ccc(*)s1 ; *c1ccc(*)nc1]

L¹ and L² are taken separately and are each independently halo, $C_1$ to $C_6$ alkyl or —CO₂H;
L⁴ is $C_1$ to $C_4$ alkyl; and
R¹ and R² are taken together and are —CH₂CH₂CH₂CH₂— or —CH₂CH=CHCH₂—, for example:
2-butyl-3-[5-(1-carboxycyclopent-3-enyl)thiophen-2-ylm-ethyl]-5-chloro-3H-imidazole-4-carboxylic acid;
3-[5-(1-carboxycyclopent-3-enyl)thiophen-2-ylmethyl]-5-ethyl-2-propyl-3H-imidazole-4-carboxylic acid; and
3-[5-(1-carboxycyclopent-3-enyl)thiophen-2-ylmethyl]-5-chloro-2-propyl-3H-imidazole-4-carboxylic acid.

Also among the particularly preferred compounds defined above are those having the structure

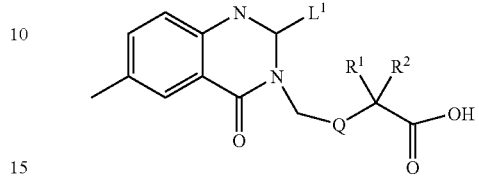

wherein:
Q is

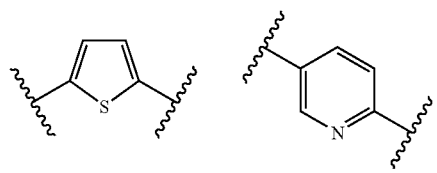 [SMILES: *c1ccc(*)s1 ; *c1ccc(*)nc1]

L⁴ is $C_1$ to $C_4$ alkyl; and
R¹ and R² are taken together and are —CH₂CH₂CH₂CH₂— or —CH₂CH=CHCH₂—, for example:
1-[5-(2-butyl-5-methyl-4-oxo-4H-quinazolin-3-ylmethyl)pyridin-2-yl]cyclopentane carboxylic acid; and
1-[5-(2-butyl-5-methyl-4-oxo-4H-quinazolin-3-ylmethyl)thiophen-2-yl]cyclopent-3-ene carboxylic acid.

Also among the particularly preferred compounds defined above are those having the structure

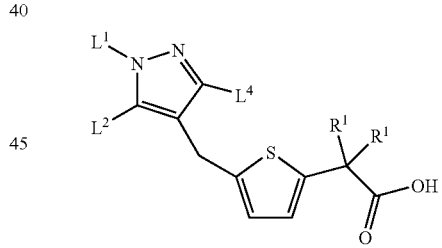

wherein:
L¹ and L² are taken separately and are each independently halo, $C_1$ to $C_6$ alkyl, polyfluoro-$C_1$ to $C_6$ alkyl or —CO₂H;
L⁴ is $C_1$ to $C_4$ alkyl; and
R¹ and R₂ are taken together and are —CH₂CH₂CH₂CH₂— or —CH₂CH=CHCH₂—, for example:
2,5-dibutyl-4-[5-(1-carboxycyclopent-3-enyl)thiophen-2-yl-methyl]-2H-pyrazole-3-carboxylic acid;
5-butyl-4-[5-(1-carboxycyclopent-3-enyl)thiophen-2-ylm-ethyl]-2-trifluoromethyl-2H-pyrazole-3-carboxylic acid; and
5-butyl-4-[5-(1-carboxycyclopent-3-enyl)thiophen-2-ylm-ethyl]-2-propyl-2H-pyrazole-3-carboxylic acid.

Other preferred compounds include compounds in the same general class as:

1-[5-(2-cyclopropyl-5,7-dimethylimidazo[4,5-b]pyridin-3-ylmethyl)thiophen-2-yl]cyclopenten-3-ene carboxylic acid benzenesulfonamide;
1-[5-(2-cyclopropyl-5,7-dimethylimidazo[4,5-b]pyridin-3-ylmethyl)thiophen-2-yl]cyclopenten-3-ene carboxylic acid p-toluenesulfonamide;
1-[5-(2-cyclopropyl-5,7-dimethylimidazo[4,5-b]pyridin-3-ylmethyl)thiophen-2-yl]cyclopenten-3-ene carboxylic acid methanesulfonamide; and
1-[5-(2-cyclopropyl-5,7-dimethylimidazo[4,5-b]pyridin-3-ylmethyl)thiophen-2-yl]cyclopenten-3-ene carboxylic acid trifluoromethanesulfonamide.

Various intermediates also fall within the scope of the present invention, including:
1-thiophen-2-yl-cyclopent-3-ene carboxylic acid ethyl ester;
1-(5-formylthiophen-2-yl)cyclopent-3-ene carboxylic acid ethyl ester;
1-(5-chloromethylthiophen-2-yl)cyclopent-3-ene carboxylic acid ethyl ester; and
1-[5-(2-ethyl-5,7-dimethylimidazo>-4,5-b!pyridin-3-ylmethyl)thiophen-2-yl!cyclopent-3-ene carboxylic acid ethyl ester.

In other embodiments, the $AT_2$ receptor antagonist is selected from 4,5,6,7-tetrahydro-1H-imidazo[4,5-c]pyridine-6-carboxylic acid analogs as described for example in U.S. Pat. No. 4,812,462 and especially in the compound claims of this patent. In illustrative examples of this type, the $AT_2$ receptor antagonist is selected from compounds having the formula (Ib):

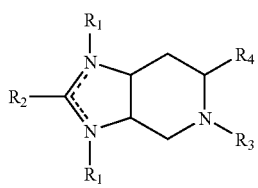

(Ib)

or their pharmaceutically compatible salts,
wherein:
(1) — is a single or a double bond;
(2) one of $R_1$ is present and is
(a) alkyl of from four to twenty carbons, inclusive,
(b)

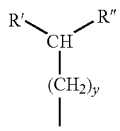

wherein y is zero, one, two, three, four or five, R' is cycloalkyl of from four to twenty carbons, inclusive in a one, two or three saturated ring system, said ring consisting of from four to eight carbons inclusive, each ring unsubstituted or substituted by a straight or branched lower alkyl group, naphthyl, heteroaryl consisting of 2-, 3-, or 4-pyridyl; 1-, 2-, or 4-imidazolyl; 1-, 2-, 3-, 4-, 5-, 6-, or 7-indolyl; 2-, or 3-thienyl; 2-, or 3-furyl; or 1-, 2-, or 3-pyrazolyl, phenyl unsubstituted or substituted with of from one through five substituents selected from the group consisting of lower alkyl, halo, trifluoromethyl, hydroxy, lower alkoxy, lower alkyl acyloxy, amino, N-lower monoalkylamino, N,N-lower dialkylamino, lower thioalkyl, lower alkylsulfonyl, nitro and

wherein $R_{10}$ is lower alkyl, phenyl unsubstituted or substituted by lower alkyl, or —$NHR_{11}$ wherein $R_{11}$ is hydrogen or lower alkyl, and R" is hydrogen, lower alkyl, cycloalkyl of from four to twenty carbons, inclusive in a one two or three saturated ring system, said ring consisting of from four to eight carbons inclusive, each ring unsubstituted or substituted by a straight or branched lower alkyl group, naphthyl, phenyl unsubstituted or substituted with of from one through five substituents selected from the group consisting of alkyl, halo, trifluoromethyl, amino, N-lower monoalkylamino, N,N-lower dialkylamino, lower thioalkyl, lower alkylsulfonyl, and nitro;
(3) $R_2$ is
(a) hydrogen,
(b) halo,
(c) lower alkyl,
(d) R'—$(CH_2)$—$_x$ wherein x is one, two, three, four, or five and R' is independently as defined above,
(e)

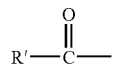

wherein R' is independently as defined above, or
(f) R'—CH(OH)— wherein R' is independently as defined above;
(4) $R_3$ is
(a) R'—$CH_2$), wherein x and R' are independently as defined above,
(b)

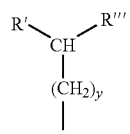

wherein R' and y are independently as defined above, and R'" is lower alkyl, cycloalkyl, of from four to twenty carbons, inclusive in a one, two or three saturated ring system, said ring consisting of from four to eight carbons inclusive, each ring unsubstituted or substituted by a straight or branched lower alkyl group, naphthyl, phenyl unsubstituted or substituted with of from one to five substituents selected from the group consisting of alkyl, halo, trifluoromethyl, amino, N-lower monoalkylamino, N,N-lower dialkylamino, lower thioalkyl, lower alkylsulfonyl, and nitro;

(c)

$$-\overset{\overset{O}{\|}}{C}-R_5$$

wherein $R_5$ is
  (i) alkyl of from one to fifteen carbons, inclusive,
  (ii)

$$\underset{\underset{|}{(CH_2)_y}}{\overset{R'\diagdown\phantom{C}\diagup R''}{CH}}$$

wherein R', R", and y are independently as defined above, $$-(-CH=CR_6-)-R_1 \qquad (iii)$$

wherein $R_6$ is hydrogen or lower alkyl and $R_1$ is as defined above, (iv)

$$\underset{\underset{|}{\underset{N}{\diagup}R_6}}{\overset{R'\diagdown\phantom{XX}}{(CH_2)_y}}$$

wherein y, R' and $R_6$ are independently as defined above, $$R'-(-CH_2-)_y-O- \qquad (v)$$

wherein y and R' are independently as defined above, (vi)

$$\underset{\underset{\underset{|}{O}}{(CH_2)_y}}{\overset{R'\diagdown\phantom{C}\diagup R''}{CH}}$$

wherein R', R", and y are independently as defined above, (d)

$$-\overset{\overset{O}{\|}}{\underset{\underset{O}{\|}}{S}}-R_5$$

wherein $R_5$ is independently as defined above;

(5) $R_4$ is
  (a) —$CH_2 OR_7$ wherein $R_7$ is hydrogen, lower acyl, a lower alkyl, (b)

$$\underset{\underset{|}{CH_2}}{\overset{R_7\diagdown\phantom{N}\diagup R_8}{N}}$$

wherein $R_7$ is independently as defined above and $R_8$ is hydrogen, lower alkyl, or benzyl, (c)

$$-\overset{\overset{O}{\|}}{CH},$$

(d) —C≡N, (e)

$$-\overset{\overset{O}{\|}}{C}OR_9,$$

wherein $R_9$ is hydrogen, lower alkyl, or benzyl; and
(6) n is one; with the overall proviso that $R_9$ cannot be hydrogen, methyl or ethyl when $R_3$ is R'—$(CH_2)$—$_x$ or $$-\overset{\overset{O}{\|}}{C}-R_5,$$

wherein $R_5$ is R'—$(CH_2)_y$O— or $$\underset{\underset{\underset{|}{O}}{(CH_2)_x}}{\overset{R'\diagdown\phantom{C}\diagup R''}{CH}}$$

wherein each of R', R", x, and y are as defined above.

In some embodiments, the compounds according to formula (Ib) have a structure wherein $R_2$ is H, n is one and $R_3$ is $$-\overset{\overset{O}{\|}}{C}R_5 \quad \text{or} \quad -\overset{\overset{O}{\|}}{\underset{\underset{O}{\|}}{S}}R_5$$

wherein $R_5$ is as defined above, $R_4$ is as defined above and $R_1$ is as defined above.

In some embodiments, the compounds according to formula (Ib) have a structure wherein $R_3$ is $$-\overset{\overset{O}{\|}}{C}R_5$$

wherein $R_5$ is as defined above.

In specific embodiments, the compounds according to formula (Ib) are selected from:

1-(4-Dimethylamino-3-methylphenyl)methyl-5-diphenylacetyl-4,5,6,7-tetrahydro-1H-imidazo[4,5-c]-pyridine-6-carboxylic acid (PD-123,319);

1-(3-methyl-4-methoxyphenyl)-methyl-5-diphenylacetyl-4,5,6,7-tetrahydro-1H-imidazo[4,5-c]pyridine-6-carboxylic acid (PD-121,981); and 1-((4-amino-3-methylphenyl)methyl)-5-(diphenylacetyl)-4,5,6,7-tetrahydro-1H-imidazo(4,5c)pyridine-6-carboxylic acid (PD-123,177), or their prodrugs or pharmaceutically acceptable salts.

In other embodiments, the $AT_2$ receptor antagonist is selected from substituted 1,2,3,4-tetahydroisoquinolines as described for example in U.S. Pat. No. 5,246,943 and especially in the compound claims of this patent. In illustrative examples of this type, the $AT_2$ receptor antagonist is selected from compounds having the formula (Ic):

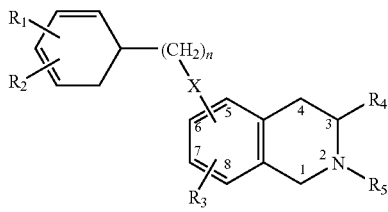

or their pharmaceutically compatible salts,
wherein:
$R_1$ and $R_2$ are each independently hydrogen, lower alkyl, halogen, hydroxy, alkoxy, amino, alkylamino, dialkylamino, acylamino, $CF_3$, carboxy, carboalkoxy, hydroxyalkyl, aminoalkyl, and nitro;
n is an integer from zero to 4;
X is absent, O, S, NH, N-alkyl, and is attached to the tetrahydroisoquinoline at the 5 or 6 position;
$R_3$ is hydrogen, alkoxy, aryloxy, alkylthio, or halogen attached either at the 6, 7, or 8 position;
$R_4$ is hydrogen, alkyl, hydroxyalkyl, $CO_2R_6$, $CON(R_6)_2$ wherein $R_6$ is hydrogen or lower alkyl; and
$R_5$ is alkyl, aryl, aralkyl which can be unsubstituted or substituted on the alkyl and/or on the aryl portion, diaralkyl (the aryl portion can be unsubstituted or substituted), $COR_7$, $SO_2R_7$ wherein $R_7$ is aralkyl, alkyl, diaralkyl, $OR_8$, $NR_8R_9$ wherein $R_8$ and $R_9$ are each independently hydrogen, alkyl, cycloalkyl, aryl, or aralkyl.

In some embodiments, the compounds according to formula (Ic) are those wherein:
$R_1$ and $R_2$ are each independently hydrogen, lower alkyl, alkoxy, amino, carboxy, and nitro;
n is an integer of from 0 to 3;
X is O, S, or NH substituted at the 5 position;
$R_3$ is hydrogen, alkoxy, or halogen substituted at the 6 position;
$R_4$ is hydrogen, alkyl, hydroxyalkyl, $CO_2R_6$, $CON(R_6)_2$; and
$R_5$ is alkyl, aryl, or $COR_7$.

In some embodiments, the compounds according to formula (Ic) are those wherein:
$R_1$ and $R_2$ are each independently hydrogen, lower alkyl, alkoxy, carboxy, and nitro;
n is an integer of from 0 to 2;
X is O substituted at the 5 position;
$R_3$ is alkoxy substituted at the 6 position;
$R_4$ is $CO_2R_6$, or $CON(R_6)_2$; and
$R_5$ is $COR_7$ wherein $R_7$ is diaralkyl or $NR_8R_9$ wherein $R_8$ and $R_9$ are each independently hydrogen, alkyl, or aryl and the aryl group may be substituted.

In specific embodiments, the compounds according to formula (Ic) are those wherein:
$R_1$ and $R_2$ are each independently hydrogen, methoxy, carboxy, methyl, nitro, or amino;
n is 0, 1, or 2;
X is O, NH;
$R_3$ is H, or $-OCH_3$;
$R_4$ is $-COOH$, $COOCH_3$, $COOC_2H_5$, $-CONH_2$, and

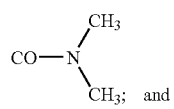 and $R_5$ is hydrogen,

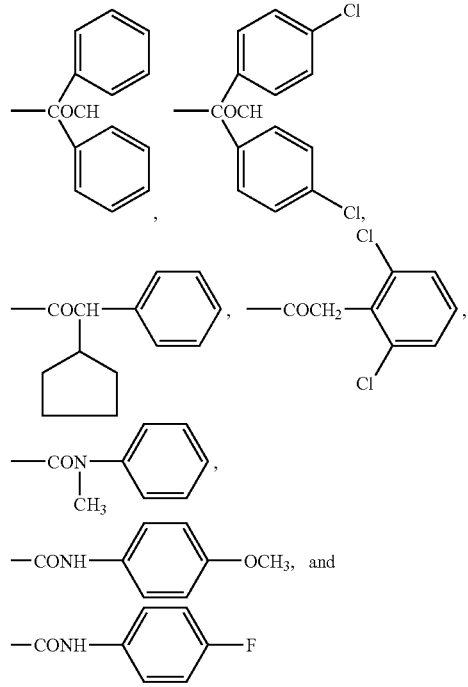

In certain embodiments, the compounds according to formula (Ic) possess one or more chiral centres and each centre may exist in the R or S configuration.

Representative examples of compounds according to formula (Ic) include, but are not limited to:

2-(Diphenylacetyl)-6-ethoxy-1,2,3,4-tetrahydro-5-(phenylmethoxy)-3-isoquinoline carboxylic acid;

2-(Diphenylacetyl)-1,2,3,4-tetrahydro-6 methoxy-5-(phenylmethoxy)-3-isoquinoline carboxylic acid;

2-(2,2-Diphenylethyl)-1,2,3,4 tetrahydro-6-methoxy-5-(phenylmethoxy)-3-isoquinolinecarboxylic acid;

2-Butyl-1,2,3,4-tetrahydro-6-methoxy 5-(phenylmethoxy)-3-isoquinoline carboxylic acid;

2-(Diphenylacetyl)-1,2,3,4-tetrahydro-6-methoxy-5-(phenylmethoxy)-3-isoquinoline carboxylic acid;

2-[(Diphenylmethyl)sulfonyl]-1,2,3,4 tetrahydro-6-methoxy-5(phenylmethoxy)-3 isoquinoline carboxylic acid;

1,2,3,4-Tetrahydro-6-methoxy-2-phenyl 5-(phenylmethoxy)-3-isoquinolinecarboxylic acid;
5-[(4 Aminophenyl)methoxy]-2-(diphenylacetyl) 1,2,3,4-tetrahydro-6 methoxy-3 isoquinoline carboxylic acid;
5-[(4 Amino-3-methylphenyl)methoxy]-2-(diphenyl acetyl)-1,2,3,4-tetrahydro-6-methoxy-3-isoquinoline carboxylic acid;
5-[[4-(Dimethylamino)-3 methylphenyl]methoxy]-2-(diphenylacetyl)-1,2,3,4-tetrahydro-6-methoxy-3-isoquinoline carboxylic acid;
(S)-2-(Diphenylacetyl)-1,2,3,4-tetrahydro-6-methoxy-5-(phenylmethoxy)-3-isoquinoline carboxylic acid;
(R)-2 (Diphenylacetyl)-1,2,3,4-tetrahydro-6-methoxy-5-(phenylmethoxy)-3-isoquinoline carboxylic acid;
2-(Diphenylacetyl)-1,2,3,4-tetrahydro-6-methoxy 5-[(phenylmethyl)thio]-3-isoquinolinecarboxylic acid;
2-(Diphenylacetyl)-1,2,3,4 tetrahydro-6-(methylthio)-5-(phenylmethoxy)-3-isoquinolinecarboxylic acid;
2-(Diphenylacetyl)-1,2,3,4-tetrahydro-6-methoxy-5-[(phenylmethyl)amino]-3-isoquinoline carboxylic acid;
2-(Diphenylacetyl)-1,2,3,4-tetrahydro-6-methoxy-5-[methyl(phenylmethyl)amino]-3-isoquinoline carboxylic acid;
2-(Diphenylacetyl)-1,2,3,4 tetrahydro 6-methoxy-5-(phenylthio)-3-isoquinolinecarboxylic acid;
2-(Diphenylacetyl)-1,2,3,4-tetrahydro-6-methoxy-5-(phenylthio)-3-isoquinoline carboxylic acid;
2-(Diphenylacetyl)-1,2,3,4-tetrahydro-6-methoxy-5-[methyl(phenylamino)]-3-isoquinoline carboxylic acid;
2-(Diphenylacetyl)-1,2,3,4 tetrahydro-6-methoxy-5-(phenylmethyl)-3-isoquinoline carboxylic acid;
2-(Diphenylacetyl)-1,2,3,4-tetrahydro-6-methoxy-5-(2-phenylethyl)-3-isoquinoline carboxylic acid;
2-(Diphenylacetyl)-1,2,3,4 tetrahydro-6-methoxy-5-phenyl-3-isoquinoline carboxylic acid;
2-(Diphenylacetyl)-1,2,3,4-tetrahydro-5-(phenylmethoxy)-3-isoquinolinecarboxylic acid;
2-(Diphenylacetyl)-1,2,3,4-tetrahydro-6-methoxy-5-(phenylmethoxy)-3-isoquinoline carboxamide;
2-(Diphenylacetyl)-1,2,3,4-tetrahydro N,N-dimethyl-6-methoxy-5-(phenylmethoxy)-3-isoquinoline carboxamide;
2-(Diphenylacetyl)-1,2,3,4-tetrahydro-6-methoxy-5-(phenylmethoxy)-3-isoquinoline carboxylic acid;
2-(Diphenylacetyl)-1,2,3,4-tetrahydro-7-methoxy-6-(phenylmethoxy)-3-isoquinoline carboxylic acid;
2-(Diphenylacetyl)-1,2,3,4-tetrahydro-6-methoxy-5-(2-phenylethoxy)-3-isoquinoline carboxylic acid;
2-[Bis(4-chlorophenyl)acetyl]-1,2,3,4-tetrahydro-6-methoxy-5-(phenylmethoxy)-3-isoquinoline carboxylic acid;
2-(Cyclopentylphenylacetyl)-1,2,3,4-tetrahydro-6-methoxy-5-(phenylmethoxy)-3-isoquinoline carboxylic acid;
2-[(2,6-Dichlorophenyl)acetyl]-1,2,3,4-tetrahydro-6-methoxy-5-(phenylmethoxy)-3-isoquinoline carboxyli acid;
1,2,3,4-Tetrahydro-6 methoxy-2-[(methylphenyl amino)carbonyl]-5-(phenylmethoxy)-3-isoquinoline carboxylic acid;
1,2,3,4-Tetrahydro-6-methoxy-2-[[(4-methoxy phenyl) amino]carbonyl]-5 (phenylmethoxy)-3-isoquinoline carboxylic acid;
2-[[(4-Fluorophenyl)amino]carbonyl]-1,2,3,4-tetrahydro-6-methoxy-5-(phenylmethoxy)-3-isoquinolinecarboxylic acid;
2-(Diphenylacetyl)-1,2,3,4-tetrahydro-6-methoxy-5-phenylmethoxy-3-isoquinoline carboxylic acid, ethyl ester;
5-[(4-Carbomethoxyphenyl)methoxy]-2-(diphenyl acetyl)-1,2,3,4-tetrahydro 6-methoxy-3-isoquinoline carboxylic acid, ethyl ester;
5-(4-Carboxyphenylmethoxy)-2-(diphenylacetyl) 1,2,3,4-tetrahydro-6-methoxy-3-isoquinolinecarboxylic acid;
2-(Diphenylacetyl)-1,2,3,4-tetrahydro-6-methoxy-5-[(4-methoxy,-3-methylphenyl)methoxy]-3-isoquinoline carboxylic acid, ethyl ester;
2-(Diphenylacetyl)-1,2,3,4-tetrahydro-6-methoxy-5-[(4-methoxy-3-methylphenyl)methoxy]-3-isoquinoline carboxylic acid;
2-(Diphenylacetyl)-1,2,3,4-tetrahydro-6-methoxy-5-(4-nitrophenoxy)-3-isoquinolinecarboxylic acid, methyl ester;
5-(4-Aminophenoxy)-2-(diphenylacetyl)-1,2,3,4-tetrahydro-6-methoxy 3-isoquinoline carboxylic acid, methyl ester;
5-(4-Aminophenoxy)-2-(diphenylacetyl)-1,2,3,4-tetrahydro-6-methoxy-3-isoquinoline carboxylic acid; and
(+)-2-(Diphenylacetyl)-1,2,3,4 tetrahydro-6-methoxy-5-(phenylmethoxy)-3-isoquinoline carboxylic acid (PD-126,055).

Certain compounds according to formula (Ic) can exist in unsolvated forms as well as in solvated forms, including hydrated forms. In general, the solvated forms, including hydrated forms, are equivalent to unsolvated forms and are intended to be encompassed within the scope of the present invention.

In other embodiments, the $AT_2$ receptor antagonist is selected from N,N-diacylpiperazine compounds as described for example in U.S. Pat. No. 5,292,726 and especially in the compound claims of this patent. Representative examples of such compounds are represented by the formula (IIa):

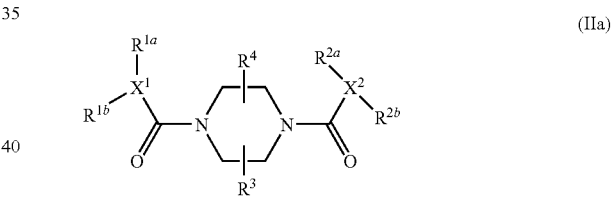

(IIa)

or their pharmaceutically compatible salts,
wherein:
wherein: $R^{1a}$ is
1) H,
2) $C_{1-8}$ alkyl.
3) phenyl, either unsubstituted or substituted with one or two substituents selected from:
  a) —$C_{1-4}$ alkyl,
  b) -halo,
  c) —OH,
  d) —CF3
  e) —$NH_2$,
  f) —NH($C_{1-4}$ alkyl).
  g) —N($C_{1-4}$ alkyl)$_2$,
  h) —$CO_2H$,
  i) —$CO_2$ ($C_{1-4}$ alkyl), and
  j) —$C_{1-4}$ alkoxy; or
4) $C_{1-4}$ alkyl-phenyl, wherein the phenyl is either unsubstituted or substituted with one or two substituents selected from:
  a) —$C_{1-4}$ alkyl,
  b) -halo,
  e) —OH,
  d) —$CF_3$ e) —NH$_2$,
f) —NH(C$_{1-4}$ alkyl),
g) —N(C$_{1-4}$ alkyl)$_2$,
h) —CO$_2$H,
i) —CO$_2$(C$_{1-4}$ alkyl), and
j) —C$_{1-4}$ alkoxy;
R$^{1b}$ is
1) R$^{1a}$,
2) —C$_{3-7}$ cycloalkyl, or
3) —CH$_2$—R$^{1a}$;
R$^{2a}$ and R$^{2b}$ are independently phenyl, either unsubstituted or substituted with one or two substituents selected from:
1) —C$_{1-4}$ alkoxy,
2) -halo,
3) —OH,
4) CF$_3$,
5) —NH$_2$,
6) —NH(C$_{1-4}$ alkyl),
7) —N(C$_{1-4}$ alkyl)$_2$,
8) CO$_2$H,
9) —CO$_2$(C$_{1-4}$ alkyl), and
10) —C$_{1-6}$ alkyl, either unsubstituted or substituted with:
 a) -halo,
 b) —OH,
 c) —CF$_3$,
 d) —NH$_2$,
 e) —NH(C$_{1-4}$ alkyl),
 f) —N(C$_{1-4}$ alkyl)$_2$,
 g) —CO$_2$H,
 h) —CO$_2$(C$_{1-4}$ alkyl),
 i) —C$_{1-4}$ alkoxy,
 j) —S(O)$_x$(C$_{1-4}$ alkyl) wherein x is 0, 1 or 2,
 k) —C$_{3-7}$ cycloalkyl;
and the phenyl groups of R$^{2a}$ and R$^{2b}$ may be joined together at the ortho carbon atoms through a carbon-carbon single bond or C$_{1-3}$ alkylene to form a tricyclic group with the X$^2$ to which they are attached;
X$^1$ is —N, —CH or O, and if X$^1$ is O, R$^{1a}$ is absent;
X$^2$ is —N or —CH;
R$^3$ is
1) —C$_{1-4}$ alkyl,
2) —CO$_2$R$^6$,
3) —CH$_2$OCOR$^6$,
4) —CH$_2$OH,
5) —CH$_2$OR$^5$,
6) —CH$_2$S(O)$_x$R$^3$,
7) —CH$_2$OCONR$^5$R$^6$,
8) —CH$_2$CONR$^5$R$^6$,
9) —CONR$^5$R$^6$,
10) —CO$_2$R$^8$,
11) —CH$_2$CO$_2$R$^6$,
12) —CH$_2$CO$_2$R$^8$,
13) —CONHSO$_2$R$^9$,
14) —CH$_2$N(R$^6$)CONR$^5$R$^6$,
15) —CH$_2$NH$_2$,
16) —CH$_2$NH(C$_{1-4}$ alkyl), or
17) —CH$_2$N(C$_{1-4}$ alkyl)$_2$; wherein
R$^5$ is C$_{1-6}$ alkyl either unsubstituted or substituted with:
1) -halo,
2) —OH,
3) —CF$_3$,
4) —NH$_2$,
5) —NH(C$_{1-4}$ alkyl),
6) —N(C$_{1-4}$ alkyl)$_2$,
7) —CO$_2$H,
8) —CO$_2$(C$_{1-4}$ alkyl),
9) —C$_{3-7}$ cycloalkyl, or
10) phenyl, either unsubstituted or substituted with
 a) —C$_{1-4}$ alkyl,
 b) -halo,
 c) —OH,
 d) —CF$_3$,
 e) —NH$_2$,
 f) —NH(C$_{1-4}$ alkyl),
 g) —N(C$_{1-4}$ alkyl)$_2$,
 h) —CO$_2$H, or
 i) —CO$_2$(C$_{1-4}$ alkyl);
R$^6$ is —H or C$_{1-4}$ alkyl; or
R$^5$ and R$^6$ can be joined together to form with the nitrogen to which they are attached —N(CH$_2$CH$_2$)$_2$L; wherein L is:
 i) a single bond,
 ii) —CH$_2$—,
 iii) —O—,
 iv) —S(O)$_p$—, or
 v) —NR$^7$;
R$^7$ is
1) —H,
2) —C$_{1-6}$ alkyl, unsubstituted or substituted with —OH, C$_{1-4}$ alkoxy or —N(C$_{1-4}$ alkyl)$_2$,
3) -aryl, or
4) —CH$_2$-aryl;
R$^8$ is
1) —H,
2)

$$\overset{R^7}{\underset{|}{-\text{CHOCOR}^{10}}}$$

wherein:
R$^{10}$ is
 a) —C$_{1-6}$ alkyl,
 b) -aryl, or
 c) —CH$_2$-aryl,
3) —CH$_2$-aryl;
R$^9$ is
1) -aryl,
2) -heteroaryl,
3) —C$_{3-7}$cycloalkyl,
4) -polyfluoro C$_{1-4}$ alkyl
5) —C$_{1-6}$alkyl, either unsubstituted or substituted with
 a) -aryl,
 b) -heteroaryl,
 c) —OH,
 d) —SH,
 e) —C$_{1-4}$alkyl,
 f) —C$_{3-7}$cycloalkyl,
 g) —C$_{1-4}$alkoxy,
 h) —C$_{1-4}$alkylthio,
 i) —CF$_3$,
 j) -halo,
 k) —NO$_2$,
 l) —CO$_2$R$^6$
 m) —N(R$^6$)$_2$, wherein the R$^6$ groups are the same or different,
 n) —NH-aryl,
 o) —N(aryl)$_2$,
 p) —PO$_3$H,
 q) —PO(OH)(OC$_{1-4}$alkyl) or
 r) —N(CH$_2$CH$_2$)$_2$L wherein L is as defined above, and
R$^4$ is H or R$^3$.

In some embodiments, the compounds according to formula (IIa) are those wherein $X^1$ and $X^2$ are both N. An illustrative class of compounds within these embodiments includes those compounds wherein:

$R^{1a}$ and $R^{1b}$ are independently H, $C_{1-8}$ alkyl or phenyl, either unsubstituted or substituted with —Cl, —Br, —I, —F, $C_{1-4}$ alkyl, or $C_{1-4}$ alkoxy: and $R^3$ is —$CO_2R^6$, or $C_{1-4}$alkyl; and $R^4$ is H or $R^3$.

Specific compounds within this class include:
1) 1-(N,N-diphenylcarbamoyl)-4-(N,N-di-n-pentylcarbamoyl)piperazine-2-carboxylic acid;
2) methyl 1-(N,N-diphenylcarbamoyl)-4-(N,N-di-n-pentylcarbamoyl)piperazine-2-carboxylate;
3) 1,4-bis(N,N-diphenylcarbamoyl)piperazine-2-carboxylic acid (L-159,686);
4) 1,4-bis(N,N-diphenylcarbamoyl)-2-methylpiperazine;
5) 1-(N,N-di-n-pentylcarbamoyl)-4-(N,N-diphenylcarbamoyl)piperazine-2-carboxylic acid;
6) 1-(N-n-pentyl-N-phenylcarbamoyl)-4-(N,N-diphenylcarbamoyl)piperazine-2-carboxylic acid;
7) 1-[N-(3-chlorophenyl)-N-phenylcarbamoyl]-4-(N,N-di-n-pentylcarbamoyl)piperazine-2-carboxylic acid;
8) 1-[N-(3-bromophenyl)-N-phenylcarbamoyl]-4-(N,N-di-n-pentylcarbamoyl)piperazine-2-carboxylic acid;
9) 1,4-bis(N,N-diphenylcarbamoyl)-trans-2,5-dimethyl-piperazine;
10) 1,4-bis[N-(3-chlorophenyl)-N-phenylcarbamoyl]-2,5-dimethyl-piperazine; and
11) 1,4-bis[-N-(3-chlorophenyl)-N-phenylcarbamoyl]-2,5-transdimethyl piperazine.

Another class of compounds within these embodiments includes those compounds wherein:

$R^{1a}$ and $R^{1b}$ are independently H, $C_{1-8}$ alkyl or phenyl, either unsubstituted or substituted with —Cl, —Br, —I, —F, $C_{1-4}$ alkyl, or $C_{1-4}$alkoxy;

$R^3$ is $CONR^5R^6$;

$R^4$ is H or $R^3$;

$R^5$ is $C_{1-6}$ alkyl either unsubstituted or substituted with:
1) -halo,
2) —OH,
3) —$CF_3$,
4) —$NH_2$,
5) —NH($C_{1-4}$alkyl),
6) —N($C_{1-4}$alkyl)$_2$,
7) —$CO_2H$,
8) —$CO_2$($C_{1-4}$alkyl),
9) —$C_{3-7}$ cycloalkyl, or
10) phenyl, either unsubstituted or substituted with
 a) —$C_{1-4}$alkyl,
 b) -halo,
 c) —OH,
 d) —$CF_3$,
 e) —$NH_2$,
 f) —NH($C_{1-4}$alkyl),
 g) —N($C_{1-4}$alkyl)$_2$,
 h) —$CO_2H$, or
 i) —$CO_2$($C_{1-4}$alkyl); and $R^6$ is H or $C_1$ alkyl.

Specific compounds within this class include:
1) 2-[(2-carboxyethyl)aminocarbonyl]-1-(N,N-diphenylcarbamoyl)-4-(N,N-di-n-pentylcarbamoyl)-piperazine;
2) 2-[(2-(t-butylcarboxyethyl)aminocarbonyl]-1-(N,N-diphenylcarbamoyl)-4-(N,N-di-n-pentylcarbamoyl)piperazine;
3) 2-[(3-(N,N-diethylamino)propyl)-N-methylaminocarbonyl]-1-(N,N-diphenyl-carbamoyl)-4-(N,N-di-n-pentylcarbamoyl)-piperazine;
4) 2-[(2-(N,N-dimethylamino)ethyl)-N-methylaminocarbonyl]-1-(N,N-diphenyl-carbamoyl)-4-(N,N-di-n-pentylcarbamoyl)-piperazine;
5) 2-[(2-(N,N-di(1-methylethyl)amino)ethyl)aminocarbonyl]-1-(N,N-diphenylcarbamoyl)-4-(N,N-di-n-pentyl-carbamoyl)piperazine;
6) 2-[(3-carboxypropyl)-N-methyl-aminocarbonyl]-1-(N,N-diphenylcarbamoyl)-4-(N,N-di-n-pentyl-carbamoyl)piperazine;
7) 2-[(3-(N,N-Diethylamino)propyl)aminocarbonyl]-4-(N,N-di-n-pentylcarbamoyl)-1-(N,N-diphenylcarbamoyl)piperazine;
8) 2-[(4-(N,N-Diethylamino)butyl)aminocarbonyl]-4-(N,N-di-n-pentylcarbamoyl)-1-(N,N-diphenylcarbamoyl)piperazine;
9) 2-[(2-Aminoethyl)aminocarbonyl]-4-(N,N-di-n-pentylcarbamoyl)-1-(N,N-diphenylcarbamoyl)piperazine;
10) 1-[N-(3-Chlorophenyl)-N-phenylcarbamoyl]-2-[(3-(N,N-diethylamino)propyl)aminocarbonyl]-4-(N,N-di-n-pentylcarbamoyl)piperazine;
11) 1,4-B is [N-(3-chlorophenyl)-N-phenylcarbamoyl]-2-[(3-(N,N-diethylamino)propyl)aminocarbonyl]piperazine;
12) 1-[N-(3-Chlorophenyl)-N-phenylcarbamoyl]-2-[(4-(N,N-diethylamino)butyl)aminocarbonyl]-4-(N,N-di-n-pentylcarbamoyl)piperazine;
13) 2-[(3-(N,N-Diethylamino)propyl)aminocarbonyl]-4-(N,N-di-n-pentylcarbamoyl)-1-[N-(3-methylphenyl)-N-phenylcarbamoyl]piperazine;
14) 1-[N-(3-Chlorophenyl)-N-phenylcarbamoyl]-2-[(2-(N,N-diethylamino)ethyl)aminocarbonyl]-4-(N,N-di-n-pentylcarbamoyl)piperazine;
15) 2-[(2-(N,N-Diethylamino)ethyl)aminocarbonyl]-4-(N,N-di-n-pentylcarbamoyl)-1-(N,N-diphenylcarbamoyl)-piperazine;
16) 2-[(4-(N,N-Diethylamino)butyl)aminocarbonyl]-1-[N-(3,5-dimethylphenyl)-N-phenylcarbamoyl]-4-(N,N-di-n-pentylcarbamoyl)piperazine;
17) 1-[N-(3-Chlorophenyl)-N-phenylcarbamoyl]-2-[(3-(N,N-diethylamino)propyl)aminocarbonyl]-4-(N,N-diphenylcarbamoyl)piperazine;
18) 2-[(3-(N,N-Dimethylamino)propyl)aminocarbonyl]-4-(N,N-di-n-pentylcarbamoyl)-1-(N,N-diphenylcarbamoyl)piperazine;
19) 2-[(3-(N,N-Diethylamino)propyl)aminocarbonyl]-1-[N-(3,5-dimethylphenyl)-N-phenylcarbamoyl]-4-(N,N-di-n-pentylcarbamoyl)piperazine;
20) 2-[(2-(N,N-Dimethylamino)ethyl)aminocarbonyl]-4-(N,N-di-n-Pentylcarbamoyl)-1-(N,N-diphenylcarbamoyl)piperazine;
21) 2-[(2-(N-Methylamino)ethyl-N-methyl-aminocarbonyl]-4-(N,N-di-n-pentylcarbamoyl)-1-(N,N-di-n-diphenylcarbamoyl)-piperazine;
22) 2-[(3-(N,N-diethylamino)propyl)-aminocarbonyl]-1-[N-(3-methoxyphenyl)-N-phenylcarbamoyl]-4-(N,N-di-n-pentylcarbamoyl)-piperazine;
23) 2-[(2-(N,N-diethylamino)ethyl)-N-(2-hydroxyethyl)aminocarbonyl]-4-(N,N-di-n-pentylcarbamoyl)-1-(N,N-diphenylcarbamoyl)piperazine;
24) 2-[(3-(N,N-diethylamino)propyl)-aminocarbonyl]-1-[N-(4-hydroxyphenyl)-N-phenylcarbamoyl]-4-(N,N-di-n-pentylcarbamoyl)-piperazine, and 25) 2-[(2-(N,N-diethylamino)ethyl)-(N-(2-hydroxy)ethyl) aminocarbonyl]-1-[N-(3-chlorophenyl)-N-phenylcarbamoyl]-4-(N,N-di-n-pentyl-carbamoyl)-piperazine.

Within these compounds it is preferred that the substituent at the Z position be of the (S) stereochemical designation.

In some embodiments, the compounds according to formula (IIa) are those wherein $X^1$ and $X^2$ are both CH. An illustrative class of compounds within these embodiments includes those compounds wherein:

$R^{1a}$ and $R^{1b}$ are independently H, $C_{1-8}$ alkyl or phenyl, either unsubstituted or substituted with —Cl, —Br, —I, —F, $C_{1-4}$alkyl, or $C_1$ alkoxy; and $R^3$ is —$CO_2R^6$, $C_{1-4}$alkyl; and $R^4$ is H or $R^3$, Specific compounds within this class include:

1) 1-diphenylacetyl-4-(3,4-dimethoxyphenylacetyl)-Z-hydroxymethyl piperazine; and
2) 1-diphenylacetyl-4-(3,4-dimethoxyphenylacetyl)piperazine-2-carboxylic acid.

In some embodiments, the compounds according to formula (IIa) are those wherein $X^1$ is N and $X^2$ is CH. An illustrative class of compounds within these embodiments includes those compounds wherein:

$R^{1a}$ and $R^{1b}$ are independently H, $C_{1-8}$alkyl or phenyl, either unsubstituted or substituted with —Cl, —Br, —I, —F, $C_{1-4}$alkyl, or $C_{1-4}$alkoxy; and $R^3$ is $CO^2R^6$, or $C_{1-4}$alkyl; and $R^4$ is H or $R^3$.

Specific compounds within this class include:

1) 1-diphenylacetyl-4-(N,N-di-n-pentylcarbamoyl)piperazine-2-carboxylic acid; and
2) methyl-1-diphenylacetyl-4-(N,N-di-n-pentylcarbamoyl) piperazine-2-carboxylate.

In some embodiments, the compounds according to formula (IIa) are those wherein $X^1$ is CH and $X^2$ is of structural formula:

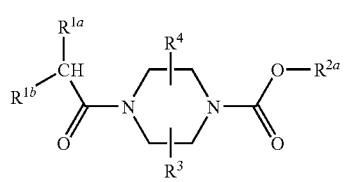

(IIa1)

or a pharmaceutically compatible salt thereof.

An illustrative class of compounds within these embodiments are includes those compounds wherein:

$R^{1a}$ and $R^{1b}$ are independently H, $C_{1-8}$alkyl or phenyl, either unsubstituted or substituted with —Cl, —Br, —I, —F, $C_{1-4}$alkyl, or $C_{1-4}$alkoxy; and $R^3$ is —$CO_2R^6$, or $C_{1-4}$alkyl; and $R^4$ is H or $R^3$.

Specific compounds within this class include:

1) 1-diphenylacetyl-4-(benzyloxycarbonyl)piperazine-2-carboxylic acid.

In other embodiments, the compounds according to formula (IIa) are those wherein $X^1$ is N and $X^2$ is of structural formula:

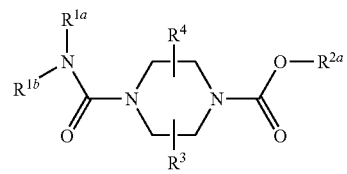

(IIa2)

An illustrative class of compounds within these embodiments includes those compounds wherein:

$R^{1a}$ and $R^{1b}$ are independently H, $C_{1-8}$ alkyl or phenyl, either unsubstituted or substituted with —Cl, —Br, —I, —F;

$R^{2a}$ is phenyl, either unsubstituted or substituted with —Cl, —Br, —I, —F, $C_{1-4}$alkyl or $C_{1-4}$alkoxy; and $R^3$ is, —$CO_2R^6$, or $C_{1-4}$alkyl; and $R^4$ is H or $R^3$.

Specific compounds within this class include:

1) 1-(N,N-diphenylcarbamoyl)-4-(benzyloxycarbonyl)piperazine-2-carboxylic acid; and
2) 1-[N-(3-chlorophenyl)-N-phenylcarbamoyl]-4-(benzyloxycarbonyppiperazine-2-carboxylic acid.

In other embodiments, the $AT_2$ receptor antagonist is selected from the N,N-diacylpiperazine compounds listed in U.S. Pat. No. 5,348,955 and especially in the compound claims of this patent. Representative examples of such compounds are represented by the formula (IIb):

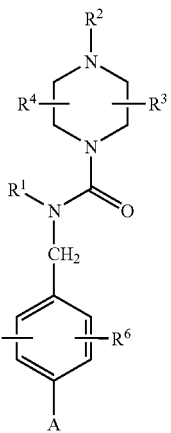

(IIb)

or their pharmaceutically compatible salts, wherein:

A is selected from:

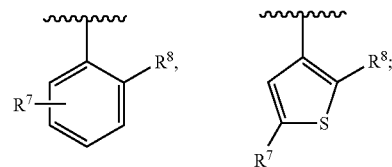

$R^1$ is selected from the group consisting of:
1) H,
2) $C_{1-8}$ alkyl,
3) $C_{3-7}$ cycloalkyl,
4) phenyl, either unsubstituted or substituted with one or two substituents selected from:

a) —$C_{1-4}$ alkyl,
b) -halo,
c) —OH,
d) —$CF_3$,
e) —$NH_2$,
f) —NH($C_{1-4}$alkyl),
g) —N($C_{1-4}$alkyl)$_2$,
h) —$CO_2H$,
i) —$CO_2$($C_{1-4}$alkyl), and
j) —$C_{1-4}$alkoxy; or 5) $C_{1-4}$alkyl-aryl, wherein the aryl is phenyl or naphthyl, either unsubstituted or substituted with one or two substituents selected from:
a) —$C_{1-4}$alkyl,
b) -halo,
c) —OH,
d) —$CF_3$,
e) —$NH_2$,
f) —NH($C_{1-4}$alkyl),
g) —N($C_{1-4}$alkyl)$_2$,
h) —$CO_2H$,
i) —$CO_2$($C_{1-4}$alkyl), and
j) —$C_{1-4}$lkoxy;

$R^2$ is selected from the group consisting of:
1) —$C_{1-6}$ alkyl,
2) —$CH_2$aryl,
3) —$CH_2$—$C_{3-7}$cycloalkyl,
4) —$CO_2R^{2a}$,
5) —CON($R^{2a}R^{2b}$),
6) —$SO_2$N($R^{2a}R^{2b}$),
7) aryl,
8) —CO-aryl, and
9) —CO—$C_{1-4}$alkyl;

$R^{2a}$ and $R^{2b}$ are independently selected from the group consisting of:
1) hydrogen,
2) —$C_{1-8}$alkyl,
3) —$C_{1-8}$alkyl-NH($C_{1-8}$alkyl),
4) —$C_{1-8}$alkyl-NH($C_{1-8}$alkyl)$_2$,
5) -aryl,
6) —$CH_2$-aryl,
or wherein —$NR^{2a}R^{2b}$ may form a heterocyclic ring of the form —N($CH_2CH_2$)$_2$L, wherein L is selected from the group consisting of O, S, N—$C_{1-4}$alkyl, N-aryl, and N—CO—$C_{1-4}$alkyl;

$R^3$ is selected from the group consisting of:
1) —$CO_2R^{2a}$,
2) —CON($R^{2a}R^{2b}$),
3) —$CH_2S$—$C_{1-4}$alkyl, and
4) —$CH_2O$—$C_{1-4}$alkyl;

$R^4$ is independently selected from:
1) H,
2) —$C_{1-6}$alkyl, and
3) —$R^3$;

$R^5$ is selected from the group consisting of:
1) hydrogen,
2) —$C_{1-6}$alkyl
3) —$C_{2-6}$alkenyl,
4) —$C_{2-4}$alkynyl,
5) halo,
6) —O—$C_{1-4}$alkyl,
7) —$CF_3$,
8) —CN, and
9) —$CH_2O$—$C_{1-4}$alkyl, $R^6$ is independently selected from
1) H, and
2) $R^5$;

$R^7$ is selected from the group consisting of:
1) —$C_{1-6}$alkyl
2) —$C_{2-6}$alkenyl,
3) —$C_{2-4}$alkynyl,
4) halo,
5) aryl,
6) —$CH_2$-aryl,
7) —O—$C_{1-4}$alkyl,
8) —$CF_3$,
9) —CN, and
10) —$CH_2O$—$C_{1-4}$alkyl;

$R^8$ is selected from the group consisting of:
1) —$CO_2R^9$, wherein $R^9$ is hydrogen or $C_{1-6}$alkyl,
2) 1H-tetrazol-5-yl,
3) —$CONHSO_2R^{10}$, wherein $R^{10}$ is selected from:
a) —$C_{1-6}$ alkyl,
b) —$C_{1-6}$alkoxy,
c) aryl,
d) —$CH_2$aryl, and
e) —CH(aryl)$_2$,
4) —$SO_2NHR^{10}$,
5) —$NHSO_2R^{10}$,
6) —$SO_2NHCOR^{10}$,
7) —$NHSO_2CF_3$, and
8) —$SO_2NHCO_2R^{10}$.

The term "aryl" means phenyl or naphthyl either unsubstituted or substituted with one, two or three substituents selected from the group consisting of halo, $C_{1-4}$-alkoxy, $NO_2$ $CF_3$, $C_{1-4}$alkylthio, OH, —N($R^{2a}R^{2b}$), —$CO_2R^{2a}$, $C_{1-4}$-perfluoroalkyl, $C_{3-6}$-perfluorocycloalkyl, and tetrazol-5-yl.

The term "heteroaryl" means an unsubstituted, monosubstituted or disubstituted five or six membered aromatic heterocycle comprising from 1 to 3 heteroatoms selected from the group consisting of O, N and S and wherein the substituents are members selected from the group consisting of —OH, —SH, —$C_{1-4}$-alkyl, —$C_{1-4}$-alkoxy, —$CF_3$, halo, —$NO_2$, —$CO_2R^{2a}$, —N($R^{2a}R^{2b}$) and a fused benzo group;

The term "halo" means —Cl, —Br, —I or —F.

The term "alkyl," "alkenyl," "alkynyl" and the like include both the straight chain and branched chain species of these generic terms wherein the number of carbon atoms in the species permit. Unless otherwise noted, the specific names for these generic terms shall mean the straight chain species. For example, the term "butyl" shall mean the normal butyl substituent, n-butyl.

In some embodiments, the compounds according to formula IIb are represented by the formula (IIbi):

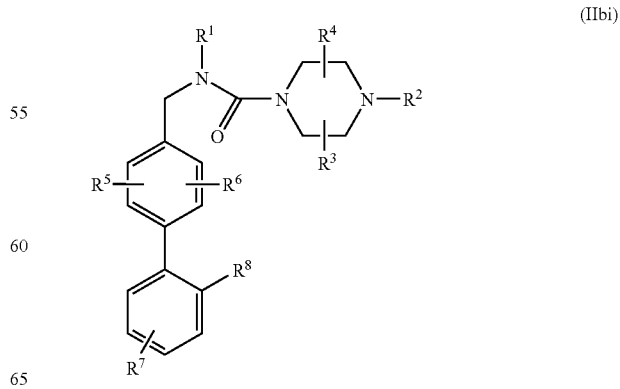

(IIbi)

or their pharmaceutically compatible salts.

Representative compounds according to formula (IIbi) include:

(S)-1-(Diphenylcarbamoyl)-4-N-pentyl-N-[2-(1H-tetrazol-5-yl]biphenyl-4-yl)-methyl]carbamoyl]-piperazine-2-carboxylic acid (L-162,132);

(S)-4-(Dipentylcarbamoyl)-1-[N-pentyl-N-[2-(1H-tetrazol-5-yl)biphenyl-4-yl)methyl]carbamoyl]-piperazine-2-carboxylic acid;

(S)-4-(Diphenylcarbamoyl)-1-{N-pentyl-N-[2-(1H-tetrazol-5-yl)biphenyl-4-yl)methyl]carbamoyl}-piperazine-2-carboxylic acid;

(S)-1-(Diphenylcarbamoyl)-4-{N-pentyl-N-[2-(1H-tetrazol-5-yl]-5-(propyl)-biphenyl-4-yl)-methyl]carbamoyl}-piperazine-2-carboxylic acid;

(S)-1-(Diphenylcarbamoyl)-4-{N-pentyl-N-[2-(1H-tetrazol-5-yl]-5-propyl-3-thienyl)phenyl]-methyl]carbamoyl}-piperazine-2-carboxylic acid; and (S)-4-(Dipentylcarbamoyl)-1-(diphenylcarbamoyl)-piperazine-2-(3-morpholino propyl)carboxamide.

In still other embodiments, the $AT_2$ receptor antagonist is selected from the substituted quinazolinone compounds listed in U.S. Pat. No. 5,441,959 and especially in the compound claims of this patent. Representative examples of such compounds are represented by the formula (IIIa):

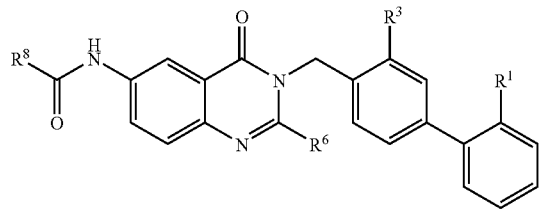

(IIIa)

or a pharmaceutically compatible salt thereof,
wherein:
$R^1$ is —$SO_2NHCO_2R^{23}$;
$R^3$ is
(a) halogen (Cl, Br, I, F),
(b) $C_1$-$C_4$ alkyl, or
(c) $CF_3$;
$R^6$ is straight chain $C_1$-$C_4$ alkyl;
$R^8$ is
(a) $R^{23'}$
(b) $NR^{24}R^{23'}$;
$R^{23}$ and $R^{23'}$ are independently
(a) aryl, wherein aryl is defined as phenyl or naphthyl unsubstituted or substituted with one or two substituents selected from the group consisting of: halogen (Cl, Br, I, F), $N(R^{24})_2$, $CO_2R^{24}$, $C_1$-$C_4$ alkyl, $C_1$-$C_4$ alkoxyl, $NO_2$, $CF_3$, $C_1$-$C_4$ alkylthio, OH, —$SO_2$ $N(R^{24})_2$, $C_3$-$C_7$ cycloalkyl, $C_3$-$C_{10}$ alkenyl and $S(O)_n(C_1$-$C_4$ alkyl); where n=1 or 2,
(b) heteroaryl, wherein heteroaryl is an unsubstituted or mono or disubstituted heteroaromatic 5- or 6-membered ring which can contain one or two heteroatoms selected from the group consisting of N, O and S and wherein the substituents are members selected from the group consisting of —OH, —SH, $C_1$-$C_4$ alkyl, $C_1$-$C_4$ alkoxy, $CF_3$, halogen (Cl, Br, I, F) and $NO_2$,
(c) $C_3$-$C_7$ cycloalkyl,
(d) $C_1$-$C_6$ alkyl optionally substituted with a substituent selected from the group consisting of aryl as defined above, heteroaryl as defined above, —OH, —SH, $C_1$-$C_4$ alkyl, —O($C_1$-$C_4$ alkyl), $C_3$-$C_7$ cycloalkyl, —$S(O)_n(C_1$-$C_4$ alkyl), —$CF_3$, halogen (Cl, Br, F, I), —$NO_2$, —$CO_2H$, $CO_2$—($C_1$-$C_4$ alkyl), —$NH_2$, —$NH(C_1$-$C_4$ alkyl), —$N(C_1$-$C_4$ alkyl)$_2$, or
(e) perfluoro-$C_1$-$C_4$ alkyl; and
$R^{24}$ is
(a) H,
(b) $C_1$-$C_6$ alkyl, unsubstituted or substituted with aryl as defined above or heteroaryl as defined above, or
(c) aryl; and $R^{23'}$ and $R^{24}$ when taken together may form a morpholine or piperazine ring, wherein the piperazine ring may be substituted on the nitrogen with $C_1$-$C_4$ alkyl or $C_1$-$C_4$ acyl.

One embodiment of the compounds of formula (IIIa) are those wherein:

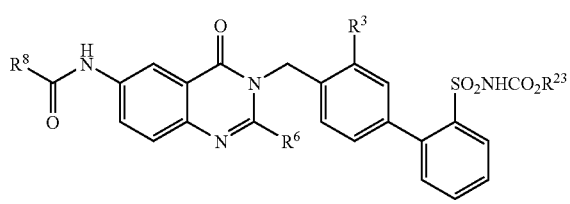

$R^3$ is
(a) F,
(b) Me, or
(c) $CF_3$;
$R^6$ is straight chain $C_1$-$C_4$ alkyl;
$R^8$ is $R^{23'}$;
$R^{23'}$ is
(a) aryl, wherein aryl is defined as phenyl or naphthyl unsubstituted or substituted with one or two substituents selected from the group consisting of: halogen (Cl, Br, I, F), $N(R^{24})_2$, $CO_2R^{24}$, $C_1$-$C_4$ alkyl, $C_1$-$C_4$ alkoxyl, $NO_2$, $CF_3$, $C_1$-$C_4$ alkylthio, OH, —$SO_2N(R^{24})_2$, $C_3$-$C_7$ cycloalkyl, $C_3$-$C_{10}$ alkenyl and $S(O)_n(C_1$-$C_4$ alkyl); where n=1 or 2,
(b) heteroaryl, wherein heteroaryl is an unsubstituted or mono- or disubstituted heteroaromatic 5- or 6-membered ring which can contain one or two heteroatoms selected from the group consisting of N, O and S and Wherein the substituents are members selected from the group consisting of —OH, —SH, $C_1$-$C_4$ alkyl, $C_1$-$C_4$ alkoxy, $CF_3$, halogen (Cl, Br, I, F) and $NO_2$,
(c) $C_1$-$C_6$ alkyl unsubstituted or substituted with a substituent selected from the group consisting of aryl as defined above, heteroaryl as defined above, —OH, —SH, $C_1$-$C_4$ alkyl, —O($C_1$-$C_4$ alkyl), $C_3$-$C_7$ cycloalkyl, —$CF_3$, halogen (Cl, Br, F, I), —$N(C_1$-$C_4$ alkyl)$_2$, or $C_3$-$C_7$ cycloalkyl; and
$R^{23}$ is
(a) $C_1$-$C_6$-alkyl, unsubstituted or substituted with a substituent selected from the group consisting of: aryl as defined above, heteroaryl as defined above, $C_1$-$C_4$ alkyl, $CF_3$, —O($C_1$-$C_4$ alkyl), $C_3$-$C_7$ cycloalkyl, or
(b) perfluoro-$C_1$-$C_4$-alkyl.

This embodiment is exemplified further by:

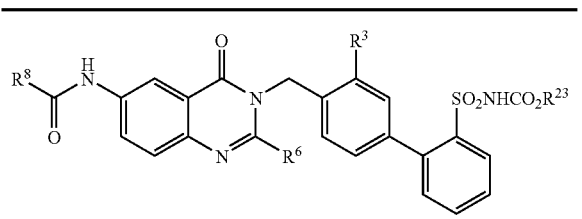

| R²³ | R³ | R⁶ | R⁸ |
|---|---|---|---|
| iPn | F | Pr | Ph |
| iPn | F | Pr | -2-furoyl |
| iPn | F | Bu | Et |
| iPn | F | Bu | Pr |
| iPn | F | Pr | CH₂OCH₂CH₃ |
| iPn | F | Et | -2-furoyl |
| iPn | F | Et | Ph |
| iPn | F | Et | -3-pyridyl |
| iPn | F | Et | -4-pyridyl |
| iPn | F | Et | -2-pyridyl |
| (CH₂)₂cPr | F | Et | Ph |
| (CH₂)₂cPr | F | Et | -2-furoyl | wherein:

Et is ethyl,

Pr is n-propyl, cPr is cyclopropyl,

Bu is n-butyl, iPn is 3-methylbutyl, and

Ph is phenyl.

A second embodiment of structures of formula (IIIa) are those wherein $R^{23}$, $R^3$, $R^6$ are as recited in the first embodiment and all other substituents are as recited below:

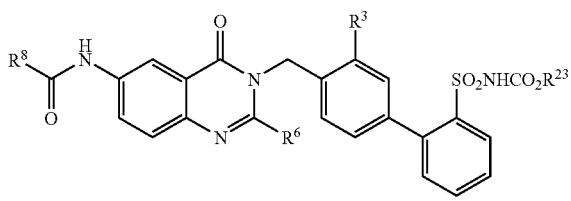

$R^8$ is —$NR^{24}R^{23'}$;

$R^{23'}$ is $C_1$-$C_6$ alkyl which is unsubstituted or substituted with a substituent selected from the group aryl, heteroaryl, $C_1$-$C_4$ alkyl, —O($C_1$-$C_4$ alkyl), $CF_3$, $NH(C_1$-$C_4$ alkyl), $N(C_1$-$C_4$ alkyl)₂, $C_3$-$C_7$ cycloalkyl;

$R^{24}$ is (a) $C_1$-$C_6$ alkyl which is unsubstituted or substituted with aryl or heteroaryl, or (b) H; and $R^{23'}$ and $R^{24}$ when taken together may form a morpholine or piperazine ring, wherein the piperazine ring may be substituted on the nitrogen with $C_1$-$C_4$ alkyl or $C_1$-$C_4$ acyl.

Compounds exemplifying this embodiment include:

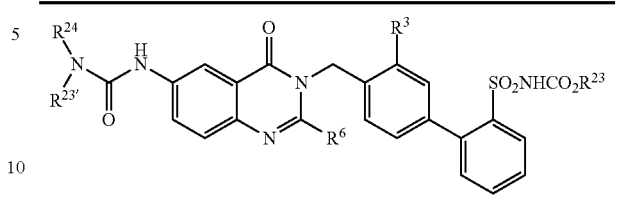

| R²³ | R³ | R⁶ | R²³' | R²⁴ |
|---|---|---|---|---|
| iPn | Me | Pr | iPr | H |
| Bu | Me | Pr | iPr | H |
| Bu | F | Pr | iPr | H |
| iPn | F | Pr | iPr | H |
| iPn | Me | Pr | iPr | H |
| Bu | F | Bu | iPr | Me |
| iPn | F | Pr | iPr | H |
| (CH₂)₂cPr | F | Bu | iPr | Me |
| (CH₂)₂cPr | F | Et | Et | H |
| Me | F | Et | Et | H |
| iPn | F | Pr | morpholino | |
| iPn | F | Bu | iPr | Me |
| iPn | F | Et | iPr | Me |
| iPn | F | Et | morpholino | |
| Bu | F | Et | morpholino | |
| iPn | F | Bu | piperazinyl-4-methyl | |
| Bu | F | Et | iPr | Me |
| (CH₂)₂tBu | F | Pr | iPr | H |
| tBu | F | Pr | iPr | H |
| iPr | F | Pr | Me | Me |
| iHex | F | Et | morpholino | |
| iPn | F | Et | Me | Me |
| (CH₂)₂cPr | F | Et | iPr | H |
| (CH₂)₂cPr | F | Et | iPr | Me |
| | L-163,579 | | | |
| iPn | F | Me | iPr | H |
| iPn | F | Me | iPr | Me |
| (CH₂)₂cPr | F | Me | Me | Me |
| iBu | F | Et | iPr | Me |
| iPn | F | Et | iPr | Me | wherein:

Me is methyl,

Et is ethyl,

Pr is n-propyl, cPr is cyclopropyl, iPr is isopropyl,

Bu is n-butyl, iBu is isobutyl, tBu is t-butyl, iPn is 3-methylbutyl, and iHex is 4-methylpentyl.

In the above embodiments described above for compounds according to formula (IIIa), the heteroaryl substituent represents any 5 or 6-membered aromatic ring containing from one to three heteroatoms selected from the group consisting of nitrogen, oxygen, and sulfur, for example, pyridyl, thienyl, furyl, pyrazolyl, pyrrolyl, imidazolyl, pyridazinyl, pyrimidinyl, pyrazinyl, isoxazolyl, isothiazolyl, oxazolyl, triazolyl and thiazolyl.

In other embodiments, the $AT_2$ receptor antagonist is selected from the disubstituted 6-aminoquinazolinone compounds listed in U.S. Pat. No. 5,385,894 and especially in the compound claims of this patent. Representative examples of such compounds are represented by the formula (IVa):

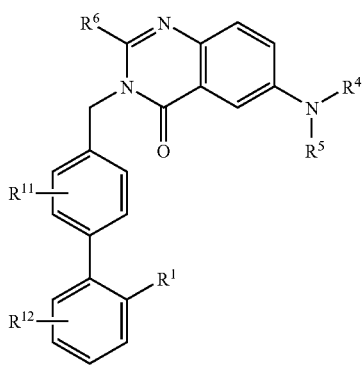

(IVa)

or a pharmaceutically compatible salt thereof,
wherein:
$R^1$ is
(a) $CO_2R^2$,
(b) tetrazol-5-yl,
(c) $NHSO_2CF_3$,
(d) $SO_2NHCOR^3$, or
(e) $SO_2NH$-heteroaryl;
$R^2$ is
(a) hydrogen, or
(b) $C_1$-$C_6$ alkyl;
$R^3$ is
(a) $C_1$-$C_6$ alkyl,
(b) $C_3$-$C_7$ cycloalkyl,
(c) phenyl,
(d) substituted phenyl in which the substituent is F, Cl, Br, $C_1$-$C_4$ alkoxy, perfluoro $C_1$-$C_4$ alkyl, di-($C_1$-$C_4$-alkyl)amino, or $CO_2R^2$,
(e) substituted $C_1$-$C_8$ alkyl in which the substituent is $C_3$-$C_7$ cycloalkyl, $C_1$-$C_4$ alkoxy, hydroxy, di-($C_1$-$C_4$ alkyl)amino, $CO_2R_2$, morpholinyl, $C_1$-$C_4$ alkylpiperazinyl, $CF_3$, thio, $C_1$-$C_4$ alkylsulfinyl, $C_1$-$C_4$ alkylsulfonyl, heteroaryl, $NH_2$, or aryl, or
(f) heteroaryl;
$R^4$ is
(a) $C_1$-$C_6$ alkyl,
(b) substituted $C_1$-$C_6$ alkyl in which the substituent is $C_3$-$C_7$ cycloalkyl, $C_1$-$C_4$ alkoxy, hydroxy, di-($C_1$-$C_4$ alkyl)amino, $CO_2R_2$, morpholinyl, $C_1$-$C_4$ alkylpiperazinyl, $CF_3$, $C_1$-$C_4$ alkylthio, $C_1$-$C_4$ alkylsulfinyl, $C_1$-$C_4$ alkylsulfonyl, —CHO, $O(C_2$-$C_3$ alkyl-O—$)_n C_1$-$C_3$ alkyl where n=1-5, or $NHCO_2(C_1$-$C_6$-alkyl).
(c) $C_2$-$C_6$ alkenyl,
(d) phenyl $C_1$-$C_6$ alkyl,
(e) substituted phenyl $C_1$-$C_6$ alkyl, in which the substituent on the phenyl group is hydroxy, $C_1$-$C_4$ alkoxy, F, Cl, I, Br, $NO_2$, cyano, $CO_2R^2$, di($C_1$-$C_4$ alkyl)amino, -Obenzyl, $CF_3$, alkoxy, $C_1$-$C_4$ alkylthio, $C_1$-$C_4$-alkylsulfinyl, —OPO(O-benzyl)$_2$, or $C_1$-$C_4$ alkylsulfonyl, amino, $P(O)(OH)_2$, $C_1$-$C_4$ alkyl, —OPO(O—$C_1$-$C_6$ alkyl)$_2$, $OPO(OH)_2$, $OCO(CH_2)_2COOH$, $OSO_3H$, or $O(C_2$-$C_3$ alkyl-O—$)_n C_1$-$C_3$ alkyl,
(f) heteroaryl $C_1$-$C_6$ alkyl, or
(g) substituted heteroaryl $C_1$-$C_6$ alkyl, in which the substituent on the heteroaryl group is F, Cl, $NO_2$, $CO_2R^2$, or di-($C_1$-$C_4$ alkyl)amino;
$R^5$ is
(a) $CO_2R^7$,
(b) $CONR^8R^9$,
(c) $COR^{10}$,
(d) $SO^2NR^8R^9$, or
(e) $SO_2R^{10}$;
$R^6$ is
(a) $C_1$-$C_6$ alkyl,
(b) substituted $C_1$-$C_6$ alkyl in which the substituent is $C_3$-$C_7$ cycloalkyl, benzyl or $C_1$-$C_4$-alkoxy,
(c) cyclopropyl;
$R^7$ is
(a) $C_1$-$C_6$ alkyl,
(b) substituted $C_1$-$C_6$ alkyl in which the substituent is $C_1$-$C_4$ alkoxy, hydroxy, di($C_1$-$C_4$ alkyl)amino, $CO_2R^2$, morpholinyl, $C_1$-$C_4$ alkylpiperazinyl, $C_1$-$C_4$ alkylsulfinyl, $C_1$-$C_4$ alkylsulfonyl, or $O(C_2$-$C_3$ alkyl-O—$)_n C_1$-$C_3$ alkyl,
(c) phenyl $C_1$-$C_6$ alkyl,
(d) substituted phenyl $C_1$-$C_6$ alkyl, in which the substituent on the phenyl group is hydroxy, $C_1$-$C_4$ alkoxy, F, Cl, $NO_2$, cyano, $CO_2R^2$, di($C_1$-C4 alkyl)amino, $CF_3$, phenyl $C_1$-$C_4$ alkoxy, $C_1$-$C_4$ alkylthio, alkylsulfinyl, $C_1$-$C_4$ alkylsulfonyl, or $O(C_2$-$C_3$ alkyl-O—$)_n C_1$-$C_3$ alkyl,
(e) heteroaryl $C_1$-$C_6$ alkyl, or
(f) substituted heteroaryl $C_1$-$C_6$ alkyl, in which the substituent on the heteroaryl group is F, Cl, $NO_2$, $CO_2R^2$, or di-($C_1$-$C_4$ alkyl)amino;
$R^8$ is
(a) hydrogen, or
(b) $C_1$-$C_6$ alkyl;
$R^9$ is
(a) $C_1$-$C_6$ alkyl, or
(b) substituted $C_1$-$C_6$ alkyl in which the substituent is $C_1$-$C_4$ alkoxy, hydroxy, di-($C_1$-$C_4$ alkyl)amino, $CO_2R^2$, morpholinyl, $C_1$-$C_4$ alkylpiperazinyl, $C_1$-$C_4$ alkylsulfinyl or $C_1$-$C_4$ alkylsulfonyl,
(c) perfluoro $C_1$-$C_6$ alkyl,
(d) phenyl,
(e) heteroaryl, or
$R^8$ and $R^9$ taken together are morpholino,

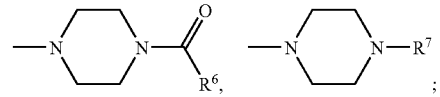

$R^{10}$ is
(a) phenyl,
(b) substituted phenyl in which the substituent is F, Cl, Br, I, $C_1$-$C_4$-alkoxy, $C_1$-$C_4$ alkyl, $NO_2$, cyano, $OC_6H_5$, $CO_2R_2$, di($C_1$-$C_4$ alkylamino), $CF_3$, $C_1$-$C_4$ alkylthio, $C_1$-$C_4$ alkylsulfinyl, alkylsulfonyl, —OPO($OC_1$-$C_6$-alkyl)$_2$, $OPO(OH)_2$, $OPO(O$-benzyl)$_2$, $OCO(CH_2)_2COOH$, $OSO_2OH$, —PO($OC_1$-$C_6$-alkyl)$_2$, —PO(OH)$_2$, OBn, or O—($C_2$-$C_3$ alkyl-O)$_n$ $C_1$-$C_3$ alkyl,
(c) phenyl $C_1$-$C_6$ alkyl,
(d) heteroaryl,
(e) $C_1$-$C_6$ alkyl,
(f) substituted $C_1$-$C_6$ alkyl in which the substituent is $C_3$-$C_7$ cycloalkyl, $C_1$-$C_4$ alkoxy, hydroxy, di-($C_1$-$C_4$ alkyl)amino, $CO_2R^2$, morpholinyl, $C_1$-$C_4$ alkylpiperazinyl, $CF_3$, thio, $C_1$-$C_4$ alkylsulfinyl, $C_1$-$C_4$ alkylsulfonyl, imidazolyl, —N(COC$_1$-$C_6$ alkyl)piperazinyl, or N-arylpiperazinyl
(g) substituted phenyl $C_1$-$C_6$ alkyl, in which the substituent on the phenyl group is hydroxy, $C_1$-$C_4$ alkoxy, F, Cl, $NO_2$, cyano, $CO_2R^2$, di(C1-C4 alkyl)amino, $CF_3$, phenyl $C_1$-$C_4$ alkoxy, thio, $C_1$-$C_4$ alkylsulfinyl, or $C_1$-$C_4$-alkylsulfonyl, or
(h) $C_3$-$C_7$ cycloalkyl.

$R^{11}$ is
(a) hydrogen,
(b) F, Cl, Br or I
(c) $C_1$-$C_1$ alkyl,
(d) $C_1$-$C_4$ alkoxy,
$R^{12}$ is
(a) hydrogen,
(b) $C_1$-$C_5$ alkyl,
(c) phenyl,
(d) substituted phenyl in which the substituent is $C_1$-$C_4$ alkoxy, F, Cl, $CO_2R^2$, di($C_1$-$C_4$ alkyl)amino, thio, $C_1$-$C_4$ alkylsulfinyl, $C_1$-$C_4$ alkylsulfonyl.

In some of the above embodiments, the term heteroaryl means an unsubstituted, monosubstituted or disubstituted five or six membered aromatic ring which contains 1 to 3 heteroatoms selected from O, S, or N and the substituents are selected from the group consisting of $C_1$-$C_4$ alkyl, F, Cl, $CO_2R^2$, or di-($C_1$-$C_4$ alkyl)amino.

The abbreviations defined in the table below are used in the specific embodiments which are illustrated in tabular form:

| Table of Abbreviations | | | |
|---|---|---|---|
| Me | methyl | iPn | isopentyl |
| Et | ethyl | Hex | n-hexyl |
| Pr | n-propyl | cHex | cyclohexyl |
| iPr | isopropyl | Boc | butyloxycarbonyl |
| cPr | cyclopropyl | Ph | phenyl |
| Bu | n-butyl | Bn | benzyl |
| iBu | isobutyl | Bz | benzoyl |
| tBu | tertbutyl | TET | tetrazol-5-yl |
| Pn | n-pentyl | PIP | Piperazinyl |

In a first specific embodiment of the compounds according to formula (IVa), $R^5$ is $CO_2R^7$. One class of this embodiment is represented by the compounds of the formula (IVa) wherein:
$R^1$ is tetrazol-5-yl or $SO_2NHCOR^3$ or $NHSO_2CF_3$
$R^3$ is
a) phenyl,
b) substituted phenyl in which the substituent is F, Cl, Br, I or $C_1$-$C_4$ alkoxy,
c) $C_1$-$C_8$ alkyl substituted with di-($C_1$-$C_4$-alkyl)amino or $NH_2$, or
d) $C_3$-$C_7$-cycloalkyl;
$R^4$ is
a) $C_2$-$C_6$ alkyl,
b) substituted $C_2$-$C_6$ alkyl in which the substituent is: CHO, $CO_2C_1$-$C_4$ alkyl, $CO_2H$, $OC_1$-$C_4$ alkyl, cyclohexyl, phenyl, $NHCO_2tBu$,
c) benzyl,
d) substituted benzyl in which the substituent on the phenyl group is: F, Cl, Br, I, OH, $OPO(OC_1$-$C_4$ alkyl$)_2$, OPO(Obenzyl$)_2$, OPO(OH$)_2$, —PO(OC_1$-$C_4$ alkyl$)_2$, —PO(Obenzyl$)_2$, OPO(OH$)_2$, $NO_2$, $NH_2$, N($C_1$-$C_4$ alkyl$)_2$, Obenzyl,
e) $CH_2$-heteroaryl or
f) $C_3$-$C_6$ alkenyl;
$R^6$ is
a) $C_1$-$C_6$ alkyl,
b) substituted $C_1$-$C_6$ alkyl in which the substituent is: -benzyl, —$C_1$-$C_3$ alkyl, or —$OC_1$-$C_4$ alkyl, or
c) cyclopropyl;
$R^7$ is
a) $C_1$-$C_6$ alkyl,
b) benzyl,
c) $C_2$-$C_4$ alkyl-O—$C_1$-$C_4$ alkyl or
d) phenyl;
$R^{11}$ and $R^{12}$ are hydrogen, Illustrating the first class of this embodiment are the following compounds (with their Compound Number designation) of the formula (IVa):

| $R^6$ | $R^1$ | $R^7$ | $R^4$ |
|---|---|---|---|
| Pr | TET | iBu | Et |
| Bu | TET | iBu | Bn |
| Bu | TET | tBu | Me |
| Pr | TET | iBu | Bu |
| Pr | TET | Et | Me |
| Pr | TET | iPr | Me |
| Pr | TET | Me | Me |
| Pr | TET | Bu | Me |
| Pr | TET | iBu | Pr |
| Pr | TET | iBu | Allyl |
| Pr | TET | iBu | Pn |
| Pr | TET | iBu | Pn |
| Pr | TET | iBu | $(CH_2)_3Ph$ |
| Pr | TET | Me | Bn |
| Pr | TET | iBu | Bn |
| Pr | TET | Pr | Bn |
| Pr | TET | Bu | Bn |
| Pr | TET | Bn | Bz |
| Pr | TET | Hex | Bn |
| Pr | TET | tBu | Bn |
| Pr | TET | $(CH_2)_2OMe$ | Bn |
| Pr | TET | Pr | $CH_2cHex$ |
| Pr | TET | Bu | Bu |
| Pr | TET | $(CH_2)_2OEt$ | $(CH_2)_2OMe$ |
| Et | TET | iBu | Me |
| Et | TET | iBu | Bn |
| iBu | TET | iBu | Me |
| iBu | TET | iBu | Bn |
| Me | TET | iBu | Bn |
| Me | TET | iBu | Me |
| Pr | $SO_2NHCOPh$ | iBu | Me |
| Pr | TET | Et | Bn |
| Pr | TET | Ph | $CH_2$-2-Pyr |
| Et | TET | tBu | Bn |
| Et | TET | Bn | Bn |
| Bu | $SO_2NHBz$ | iBu | Bn |
| Pr | $SO_2NHBz$ | Bu | Bn |
| Pr | $SO_2NHCOcPr$ | iBu | Bn |
| Pr | $SO_2NHCOcPr$ | iBu | Me |
| Pr | TET | Pr | $CH_2$-4-Pyr |
| Pr | TET | $(CH_2)_2OMe$ | Me |
| Pr | TET | Pr | $CH_2$-3-Pyr |
| Pr | TET | Pr | $CH_2$-2-Pyr |
| Pr | TET | $(CH_2)_2OMe$ | $CH_2$-4-Pyr |
| $CH_2OMe$ | TET | iBu | Me |
| $CH_2OMe$ | TET | Pr | $CH_2$-2-Pyr |
| Pr | $SO_2NHBz$ | Bn | Pn |
| Pr | TET | Et | $CH_2$-2-Pyr |
| Pr | TET | Pr | Bn-4-$NO_2$ |
| Pr | TET | Pr | Bn-4-$NH_2$ |
| Pr | TET | Pr | Bn-4-$NMe_2$ |
| H | TET | iBu | Me |

In a second specific embodiment of the compounds according to formula (IVa), $R^5$ is $CONR^8R^9$. One class of this embodiment is represented by the compounds of the formula (IIa) wherein:

$R^1$ is tetrazol-5-yl or $SO_2NHCOR^3$ or $NHSO_2CF_3$,
$R^3$ is
a) phenyl,
b) substituted phenyl in which the substituent is F, Cl, Br, I or $C_1$-$C_4$ alkoxy,
c) $C_1$-$C_8$ alkyl substituted with di-($C_1$-$C_4$-alkyl)amino or $NH_2$, or
d) $C_3$-$C_7$-cycloalkyl;
$R^4$ is
a) $C_2$-$C_6$ alkyl,
b) substituted $C_2$-$C_6$ alkyl in which the substituent is: CHO, $CO_2C_1$-$C_4$ alkyl, $CO_2H$, $OC_1$-$C_4$ alkyl, cyclohexyl, phenyl, or $NHCO_2$ Bu,
c) benzyl,
d) substituted benzyl in which the substituent on the phenyl group is: F, Cl, Br, I, OH, $OPO(OC_1$-$C_4$ alkyl$)_2$, OPO (Obenzyl$)_2$, $OPO(OH)_2$, —$PO(OC_1$-$C_4$-alkyl$)_2$, —PO (Obenzyl$)_2$, —$OPO(OH)_2$, $NO_2$, $NH_2$, $N(C_1$-$C_4$ alkyl$)_2$, or Obenzyl,
e) $CH_2$-heteroaryl, or
f) $C_3$-$C_6$ alkenyl;
$R^6$ is
a) $C_1$-$C_6$ alkyl,
b) substituted $C_1$-$C_6$ alkyl in which the substituent is: -benzyl, —$C_1$-$C_3$ alkyl, or —$OC_1$-$C_4$ alkyl, or
c) cyclopropyl;
$R^8$ is
a) $C_1$-$C_6$ alkyl or
b) hydrogen;
$R^9$ is
a) $C_1$-$C_6$ alkyl, or
b) when taken with $R^8$ and the nitrogen atom to which they are attached from a morpholinyl, N—($C_1$-$C_6$ alkyl)piperazinyl, N—($COC_1$-$C_6$ alkyl)piperazinyl, or N-aryl-piperazinyl ring system,
$R^{11}$ and $R^{12}$ are hydrogen.

Illustrating the first class of this second embodiment are the following compounds (with their Compound Number designation) of the formula (IVa):

| $R^6$ | $R^1$ | $N(R^8)R^9$ | $R^4$ |
|---|---|---|---|
| Bu | TET | N(Me)iPr | Me |
| Pr | TET | N(Pn)$_2$ | Me |
| Pr | TET | N(Me)Pr | Bn |
| Pr | TET | N(Me)Et | Bn |
| Pr | TET | morpholino | Bn |
| Et | TET | NHPr | Bn |
| Pr | TET | N(Me)iPr | Bn-4-F |
| Pr | TET | N(Me)iPr | $CH_2$-2-Pyr |

In a third specific embodiment of the compounds of the formula (IVa), $R^5$ is $COR^{10}$. One class of this embodiment is represented by the compounds of the formula (IVa) wherein:
$R^1$ is tetrazol-5-yl, $SO_2NHCOR^3$ or $NHSO_2CF_3$;
$R^3$ is
a) phenyl,
b) substituted phenyl in which the substituent is F, Cl, Br, I or $C_1$-$C_4$ alkoxy,
c) $C_1$-$C_8$ alkyl substituted with di-($C_1$-$C_4$ alkyl)amino or $NH_2$, or
d) $C_3$-$C_7$-cycloalkyl;
$R^4$ is
a) $C_2$-$C_6$ alkyl,
b) substituted $C_2$-$C_6$ alkyl in which the substituent is: CHO, $CO_2C_1$-$C_4$ alkyl, $CO_2H$, $OC_1$-$C_4$ alkyl, cyclohexyl, phenyl, or $NHCO_2tBu$,
c) benzyl,
d) substituted benzyl in which the substituent on the phenyl group is: F, Cl, Br, I, OH, $OPO(OC_1$-$C_4$ alkyl$)_2$, OPO (Obenzyl$)_2$, $OPO(OH)_2$, —$PO(OC_1$-$C_4$ alkyl$)_2$, —PO (Obenzyl$)_2$, $OPO(OH)_2$, $NO_2$, $NH_2$, $N(C_1$-$C_4$ alkyl$)_2$, Obenzyl, $OC_1$-$C_4$ alkyl, COOH, or $CO_2CH_3$,
e) $CH_2$-heteroaryl or
f) $C_3$-$C_6$ alkenyl;
$R^6$ is
a) $C_1$-$C_6$ alkyl,
b) substituted $C_1$-$C_6$ alkyl in which the substituent is: -benzyl, —$C_1$-$C_3$ alkyl, or —$OC_1$-$C_4$ alkyl or
c) cyclopropyl;
$R^{10}$ is
(a) phenyl,
(b) substituted phenyl in which the substituent is F, Cl, Br, I, methoxy, methyl, $CF_3$, SMe, $SO_2Me$, OH, OPO(O—$C_1$-$C_4$ alkyl$)_2$, $OPO(OH)_2$, OPO(OBn$)_2$, $CO_2C_1$-$C_4$ alkyl, COOH, Obenzyl or $OC_6H_5$,
(c) benzyl,
(d) heteroaryl,
(e) $C_1$-$C_6$ alkyl or
(f) substituted $C_1$-$C_6$ alkyl substituted with: imidazole, piperazine, morpholinyl, N—($C_1$-$C_6$ alkyl)piperazinyl, N—($COC_1$-$C_6$ alkyl)piperazinyl, or N-aryl-piperazinyl;
$R^{11}$ and $R^{12}$ are hydrogen.

Illustrating the first class of this third embodiment are the following compounds (with their Compound Number designation) of the formula (IVa):

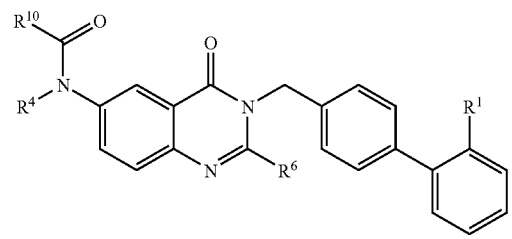

| $R^6$ | $R^1$ | $R^{10}$ | $R^4$ |
|---|---|---|---|
| Pr | TET | Ph | Pn |
| Pr | TET | Bn | Pn |
| Pr | TET | 4-Pyr | Pn |
| Pr | TET | Ph | Bn |
| Pr | TET | Ph-4-Cl | Pn |
| Pr | TET | Ph-4-Cl | Pn |
| Pr | TET | Ph-4-Ome | 4-Methylpentyl |
| Pr | TET | 2-Furyl | Pn |
| Pr | TET | 3-methylbutyl | |
| Pr | TET | Bu | Bn |
| Pr | TET | Ph-4-F | Pn |
| Pr | TET | Ph-4-F | Bu |
| Pr | TET | Ph-4-Me | Pn |
| Pr | TET | Ph-3-Br | Pn |
| Pr | TET | 3-Methylbutyl | Bn-4-OH |
| Pr | TET | Bu | Bu |
| Et | TET | Ph | Bn |
| Pr | TET | Ph-4-$CF_3$ | Pn |
| Et | TET | Ph-4-F | Pn |
| 1-Methylpentyl | TET | Ph-4-F | Pn |
| Et | TET | Ph-4-F | Bu |
| Et | TET | Ph | Bn-4-F |
| cPr | TET | Ph | Bn |
| cPr | TET | Ph | Pn |
| 1-Methyl-3-phenethyl | TET | Ph | Bn |
| cPr | TET | Ph | Bn |

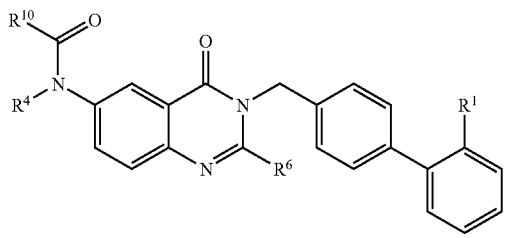

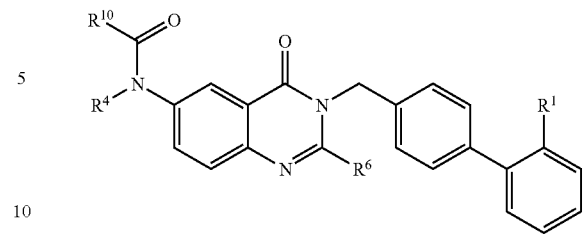

| R⁶ | R¹ | R¹⁰ | R⁴ |
|---|---|---|---|
| cPr | TET | Ph | Bn |
| Pr | TET | 4-Py | Bu |
| Me | TET | Ph | Bn |
| iPr | TET | Ph | Bn |
| Et | SO₂NHBz | Ph | Bn |
| Pr | TET | 3-Pyr | Pn |
| Pr | SO₂NHCOcPr | Ph | Pn |
| Pr | SO₂NHBz | Ph | Pn |
| Et | TET | 4-Pyr | Bn |
| Pr | TET | Ph-4-SMe | Pn |
| Pr | TET | Ph | Pr |
| Et | TET | Ph-2-Cl | Bn |
| Et | TET | Ph-2-Cl | Bn-2-Cl |
| Pr | TET | Ph-4-SOMe | Pn |
| Pr | TET | Ph | (CH₂)CHO |
| Pr | TET | Ph-4-SO₂Me | Pn |
| Et | TET | Ph | Bn-2-Cl |
| Et | TET | Ph | CH₂CH=CMe₂ |
| Pr | SO₂NHCOcPr | Me | Pr |
| Pr | SO₂NHCOcPr | cPr | Pn |
| Pr | SO₂NHCOcPr | Me | Pn |
| Pr | SO₂NHCOPh | cPr | Pr |
| Pr | TET | Ph-4-F | Pr |
| Et | TET | Ph | iPn |
| iPr | TET | Ph | Bn-2-Cl |
| iPr | TET | cPr | Bn |
| iPr | TET | cPr | Bn-2-Cl |
| H | TET | Ph | Bn |
| H | TET | Ph | Bn-2-Cl |
| Et | TET | Ph | Bn-4-Cl |
| Et | TET | Ph | Bn-4-F |
| Et | TET | Ph | Bn-3-Et |
| 1-ethyl-ethyl | TET | Ph | Bn |
| 1-ethyl-ethyl | TET | Ph | Bn-2-Cl |
| Pr | TET | Ph | iBu |
| Pr | TET | Ph | (CH₂)₃CO₂Et |
| Pr | NHSO₂CF₃ | Ph | Pn |
| Pr | TET | Ph | (CH₂)₃CO₂H |
| Me | TET | Ph | Bn-2-Cl |
| Me | TET | 4-Pyr | Bn |
| Pr | SO₂NHCOcPr | Me | Me |
| Pr | TET | Ph | CH₂CO₂Et |
| Me | TET | 4-Pyr | Bn-2-Cl |
| Me | TET | 4-Pyr | CH₂CH=CMe₂ |
| Et | TET | Ph | Bn-4-I |
| Pr | TET | 2-thienyl | Pn |
| Pr | TET | 2-thienyl | Me |
| iPr | TET | Ph | Bn-4-I |
| Et | TET | Ph-4-I | Bn |
| Et | TET | Ph | Bz-2-I |
| Et | TET | 2-thienyl | Bn |
| (L-161,638) | | | |
| Pr | TET | 4-Pyr | (CH₂)₂)OMe |
| Pr | TET | Ph | CH₂CO₂H |
| CH₂OMe | TET | Ph-4-Cl | Pn |
| Et | TET | 2-furoyl | Bn |
| Pr | TET | 2-thienyl | Bn |
| Pr | TET | 2-thienyl | Et |
| Pr | TET | 2-furoyl | Et |
| Pr | TET | Ph-2-OMe | Bn |
| Pr | TET | Ph-2-OMe | Pr |
| Pr | TET | Ph-4-OBn | Pn |
| Pr | TET | Ph-4-OBn | Pr |
| Pr | TET | Ph-4-OH | Pn |
| Pr | TET | Ph-4-OH | Pr |
| Pr | TET | CH₂imidazole | Bn |
| Pr | TET | CH₂PIPBoc | Bn |
| Pr | TET | 3-Pyr | Bn |
| Pr | TET | 2-Pyr | Bn |
| Pr | TET | Ph | CH₂-2-Pyr |
| Pr | TET | Ph | CH₂-4-Pyr |
| Pr | TET | 4-Pyr | Bn |
| Pr | TET | 2-Pyr | Bn |
| Pr | TET | Ph | CH₂-3-Pyr |
| Pr | TET | Ph | CH₂-2-Pyr |
| Pr | TET | Ph-4-OPO(OBn)₂ | Pn |
| Pr | TET | Ph-4-OH | Bu |
| Pr | TET | 4-Pyr | CH₂-2-Pyr |
| Pr | TET | Ph-4-OP(OH)₂ | Pn |
| Pr | TET | Ph-4-OH | Bn |
| Pr | TET | 2-furoyl | CH₂-2-Pyr |
| Pr | TET | Ph-4-OPO(ONa)₂ | Bu |

In a fourth embodiment of the compounds of the formula (IVa), R⁵ is SO₂R¹⁰. One class of this embodiment is represented by the compounds of the formula (IVa) wherein:

R¹ is tetrazol-5-yl, SO₂NHSO₂CF₃ or NHSO₂CF₃

R³ is
(a) phenyl,
(b) substituted phenyl in which the substituent is F, Cl, Br, I or $C_1$-$C_4$ alkoxy,
(c) $C_1$-$C_8$ alkyl substituted with di-($C_1$-$C_4$ alkyl)amino or NH₂, or
(d) $C_3$-$C_7$-cycloalkyl;

R⁴ is
(a) $C_2$-$C_6$ alkyl,
(b) substituted $C_1$-$C_6$ alkyl in which the substituent is: CHO, CO₂$C_1$-$C_4$ alkyl, CO₂H, O$C_1$-$C_4$ alkyl, cyclohexyl, phenyl, or NHCO₂tBu,
(c) benzyl,
(d) substituted benzyl in which the substituent on the phenyl group is: F, Cl, Br, I, OH, OPO(O$C_1$-$C_4$ alkyl)₂, OPO(Obenzyl)₂, OPO(OH)₂, —PO(O$C_1$-$C_4$ alkyl)₂, —PO(Obenzyl)₂, —OPO(OH)₂, NO₂, NH₂, N($C_1$-$C_4$ alkyl)₂, or Obenzyl,
(e) CH₂-heteroaryl or
(f) $C_3$-$C_6$ alkenyl;

R⁶ is
(a) $C_1$-$C_6$ alkyl,
(b) substituted $C_1$-$C_6$ alkyl in which the substituent is: -benzyl, —$C_1$-$C_3$ alkyl, or —O$C_1$-$C_4$ alkyl or,
(c) cyclopropyl;

R¹⁰ is
(a) phenyl,
(b) substituted phenyl in which the substituent is F, Cl, Br, I, methoxy, methyl, CF₃, SMe, SOMe, SO₂Me, OH, OPO(O—$C_1$-$C_4$ alkyl)₂, OPO(OH)₂, OPO(OBn)₂, CO₂$C_1$-$C_4$ alkyl, or COOH,
(c) benzyl,
(d) heteroaryl,
(e) $C_1$-$C_6$ alkyl, or (f) substituted $C_1$-$C_6$ alkyl substituted with: imidazole, piperazine, morpholinyl, N—($C_1$—C alkyl)-piperazinyl, N—(CO$C_1$-$C_6$ alkyl)-piperazinyl, or N-aryl-piperazinyl;
$R^{11}$ and $R^{12}$ are hydrogen.

Illustrating this class of the fourth embodiment is the following compounds (with its Example Number designation) of the formula (IVa):

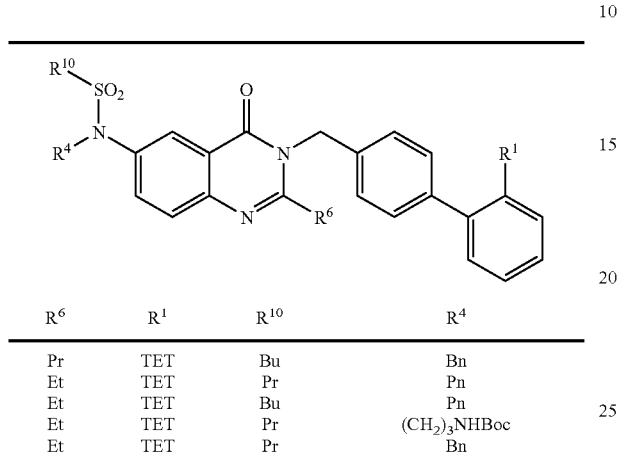

| $R^6$ | $R^1$ | $R^{10}$ | $R^4$ |
|---|---|---|---|
| Pr | TET | Bu | Bn |
| Et | TET | Pr | Pn |
| Et | TET | Bu | Pn |
| Et | TET | Pr | (CH$_2$)$_3$NHBoc |
| Et | TET | Pr | Bn |

In still other embodiments, the $AT_2$ receptor antagonist is selected from the imidazole compounds listed in U.S. Pat. No. 5,545,651 and especially in the compound claims of this patent. Representative examples of such compounds are represented by the formula (VI):

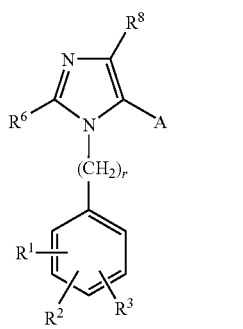

(VI)

wherein:
$R^1$ is in the meta or para position and is
(a) 4-CO$_2$H,
(b) —CH$_2$CO$_2$H,
(c) —C(CF$_3$)$_2$OH,
(d) —CONHNHSO$_2$CF$_3$,
(e) 4-CONHCH(CO$_2$H)CH$_2$C$_6$H$_5$ (L-isomer),
(f) 4-CONHOR$^{12}$,
(g) —CONHSO$_2$R$^{10}$,
(h) —CONHSO$_2$NHR$^9$,
(i) —C(OH)R$^9$PO$_3$H$_2$,
(j) —NHCOCF$_3$,
(k) —NHCONHSO$_2$R$^{10}$,
(l) —NHPO$_3$H$_2$,
(m) 4-NHSO$_2$R$^{10}$,
(n) —NHSO$_2$NHCOR$^{10}$,
(o) —OPO$_3$H$_2$,
(p) —OSO$_3$H,
(q) —PO$_3$H$_2$,
(r) —PO(OH)R$^9$,
(s) —SO$_3$H,
(t) —SO$_2$NHR$^9$,
(u) —SO$_2$NHCOR$^{10}$,
(v) —SO$_2$NHCONHR$^9$,

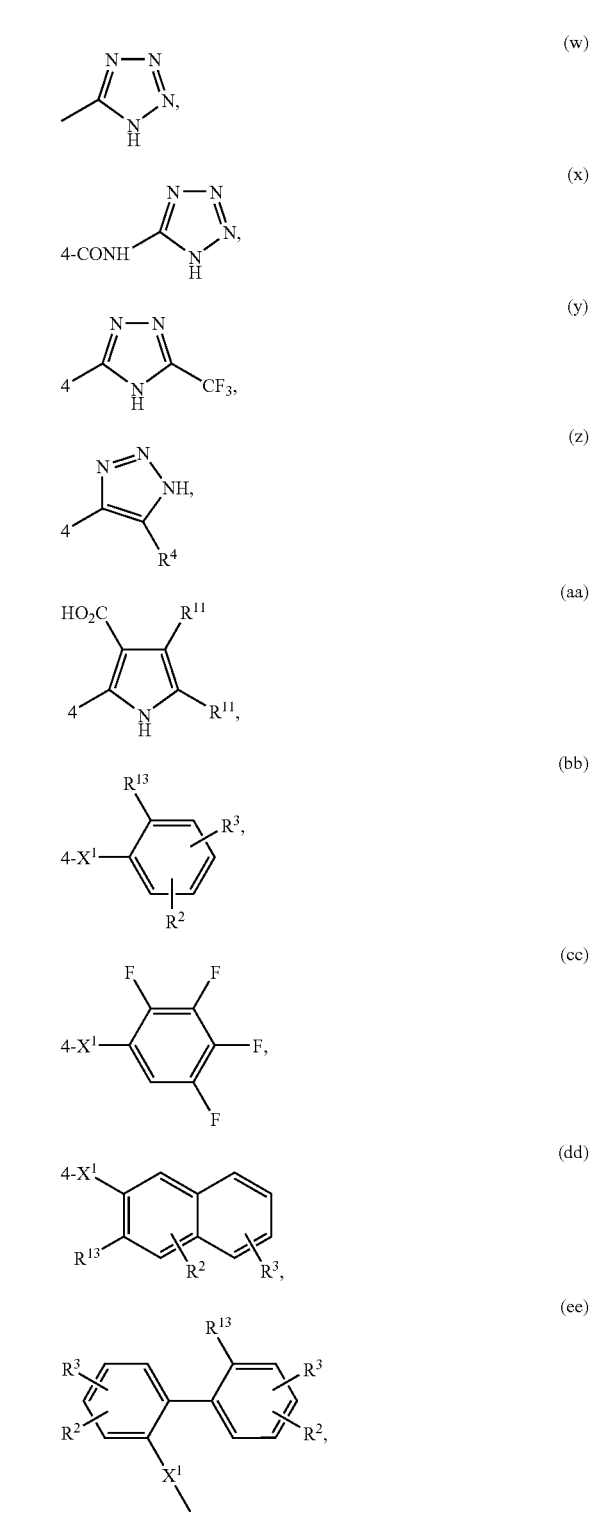

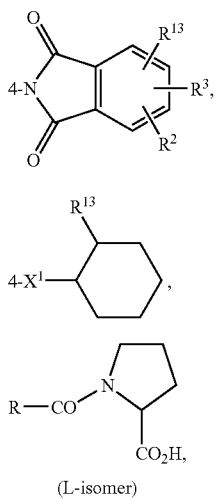

(ff)

(gg)

(hh)

(L-isomer)

(ii) -SO$_2$NHCO$_2$R$^{10}$;
R$^2$ is independently
(a) H,
(b) halo (F, Cl, Br, I),
(c) C1-4-alkyl,
(d) C1-4-alkoxy,
(e) C1-4-acyloxy,
(f) C1-4-alkylthio,
(g) C1-4-alkylsulfinyl,
(h) C1-4-alkylsulfonyl,
(i) —(C1-4-alkyl)—OH,
(j) —(C1-4) alkyl-aryl,
(k) —CO2H,
(l) —CN,
(m) tetrazol-5-yl,
(n) —CONHOR12,
(o) —SO2NHR9,
(p) —NH2,
(q) C1-4-alkylamino,
(r) C1-4-dialkylamino,
(s) —NHSO2R10,
(t) —NO2,
(u) furyl,
(v) phenyl or phenyl optionally substituted with one or two substituents selected from the group consisting of halo, C1-4-alkyl, C1-4-alkoxy, —NO2, —CF3, C1-4-alkylthio, —OH, —NH2, C1-4-alkylamino, C1-4-dialkylamino, —CN, —CO12R12, acetyl;
R$^3$ is independently
(a) H,
(b) halo,
(c) C$_{1-4}$-alkyl,
(d) C$_{1-4}$-alkoxy, or
(e) —C$_{1-4}$-alkyl-(C$_1$-C$_4$-alkoxy);
R$^4$ is
(a) —CN,
(b) —NO$_2$, or
(c) —CO$_2$R$^{11}$;
R$^5$ is
(a) H,
(b) C$_{1-6}$-alkyl,
(c) C$_{3-6}$-cycloalkyl,
(d) C$_{2-4}$-alkenyl, or
(e) C$_{2-4}$-alkynyl;

R$^6$ is
(a) C$_{1-10}$-alkyl,
(b) C$_{3-10}$-alkenyl,
(c) C$_{3-10}$-alkynyl,
(d) C$_{3-8}$-cycloalkyl,
(e) C$_{3-4}$-cycloalkenyl,
(f) —C$_{1-3}$-alkyl-(C$_3$-C$_8$-cycloalkyl),
(g) —C$_{1-3}$-alkenyl-(C$_5$-C$_{10}$-cycloalkyl),
(h) —C$_{1-3}$-alkynyl-(C$_5$-C$_{10}$-cycloalkyl),
(i) —(CH$_2$), S(CH$_2$)$_m$R$^5$, or
(j) benzyl, optionally substituted on the phenyl ring with 1-2 substituents selected from the group consisting of halo, C$_{1-4}$-alkyl, C$_{1-4}$-alkoxy or —NO$_2$;
R$^7$ is
(a) C$_{1-6}$-alkyl,
(b) C$_{3-6}$-cycloalkyl,
(c) aryl, or
(d) benzyl, optionally substituted on the phenyl ring with 1-2 substituents selected from the group consisting of halo, C$_{1-4}$-alkyl, C$_{1-4}$-alkoxy or —NO$_2$;
R$^8$ is
(a) H,
(b) halogen (F, Cl, Br, I),
(c) phenyl, or phenyl optionally substituted with halogen (F, Cl, Br, I), C$_1$-C$_4$-alkyl, —OH, C$_1$-C$_4$-alkoxy, —NO$_2$, —NR$^{26}$R$^{27}$, —NR$^{26}$COR$^{11}$, —NR$^{26}$CO$_2$R$^7$, —S(O)$_r$R$^{10}$, —SO$_2$NR$^{26}$R$^{27}$, —NR$^{26}$SO$_2$R$^{10}$, —CF$_3$,
(d) C$_1$-C$_6$-alkyl, optionally substituted with
  i) OR$^{25}$,
  ii) S(O)$_r$R$^{10}$,
  iii) NR$^{23}$R$^{24}$,
  iv) NR$^{26}$COR$^{11}$,
  v) NR$^{26}$CO$_2$R$^7$,
  vi) NR$^{26}$CONR$^{23}$R$^{24}$,
  vii) OCONR$^{23}$R$^{24}$,
  viii) OCOR$^{11}$,
  ix) aryl,
(e) C$_{2-6}$-alkenyl,
(f) —C$_{1-4}$-alkyl-aryl,
(h) C$_{1-4}$-alkoxy,
(i) C$_v$F$_{2v+1}$ where v=1 to 3,
(j) —S(O)$_r$R$^{10}$,
(k) —S(O)$_2$NR$^{23}$R$^{24}$,
(l) —CONR$^{23}$R$^{24}$,
(m) —COR$^7$, or
(n) —CO$_2$R$^{12}$;
R$^9$ is
(a) H,
(b) C$_{1-5}$-alkyl,
(c) aryl,
(d) —(C$_{1-4}$-alkyl)-aryl,
(e) heteroaryl, or
(f) C$_{3-5}$-cycloalkyl;
R$^{10}$ is
(a) aryl,
(b) C$_{3-7}$cycloalkyl,
(c) C$_{1-4}$-perfluoroalkyl,
(d) C$_{1-4}$-alkyl, optionally substituted with a substituent selected from the group consisting of aryl, heteroaryl, —OH, —SH, C$_{1-4}$-alkyl, C$_{1-4}$-alkoxy, —CF$_3$, halo, —NO$_2$, —CO$_2$R$^{12}$, —NH$_2$, C$_{1-4}$-alkylamino, —PO$_3$H$_2$, or
(e) heteroaryl;
R$^{11}$, R$^{11a}$ and R$^{11b}$ are independently
(a) H,
(b) C$_{1-6}$-alkyl,
(c) C$_{3-6}$-cycloalkyl, (d) aryl,
(e) —($C_{1-5}$-alkyl)-aryl, or
(f) heteroaryl;

$R^{12}$ is
(a) H,
(b) methyl, or
(c) benzyl, optionally substituted on the phenyl ring with 1-2 substituents selected from the group consisting of halo, $C_{1-4}$-alkyl, $C_{1-4}$-alkoxy or —$NO_2$;

$R^{13}$ is
(a) —$CO_2H$,
(b) —$CH_2CO_2H$,
(c) —$C(CF_3)_2OH$,
(d) —$CONHNHSO_2CF_3$,
(e) —$CONHOR^{12}$,
(f) —$CONHSO_2R^{10}$,
(g) —$CONHSO_2NHR^9$,
(h) —$C(OH)R^9PO_3H_2$,
(i) —$NHCOCF_3$,
(j) —$NHCONHSO_2R^{10}$,
(k) —$NHPO_3H_2$,
(l) —$NHSO_2R^{10}$,
(m) —$NHSO_2NHCOR^{10}$,
(n) —$OPO_3H_2$,
(o) —$OSO_3H$,
(p) —$PO(OH)R^9$,
(q) —$PO_3H_2$,
(r) —$SO_3H$,
(s) —$SO_2NHR^9$,
(t) —$SO_2NHCOR^{10}$,
(u) —$SO_2NHCONHR^9$,
(v) —$SO_2NHCO_2R^{10}$, (w) 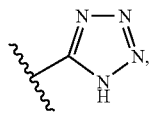

(x) 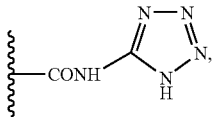

(y) 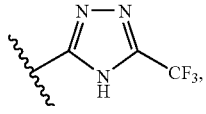

(z) 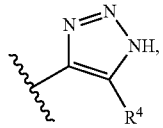

(aa) 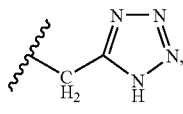

$R^{14}$ is
(a) H,
(b) $C_{1-6}$-alkyl,
(c) —$CH_2CH=CH_2$, or
(d) benzyl, optionally substituted on the phenyl ring with 1-2 substituents selected from the group consisting of halo, $C_{1-4}$-alkyl, $C_{1-4}$-alkoxy or —$NO_2$;

$R^{15}$ is
(a) H,
(b) $C_{1-8}$-alkyl,
(c) $C_{1-8}$ perfluoroalkyl,
(d) $C_{3-6}$-cycloalkyl,
(e) aryl, or
(f) benzyl, optionally substituted on the phenyl ring with 1-2 substituents selected from the group consisting of halo, $C_{1-4}$alkyl, $C_{1-4}$-alkoxy or —$NO_2$;

$R^{16}$ is
(a) H,
(b) $C_{1-6}$-alkyl, or
(c) benzyl, optionally substituted on the phenyl ring with 1-2 substituents selected from the group consisting of halo, $C_{1-4}$-alkyl, $C_{1-4}$-alkoxy or —$NO_2$;

$R^{17}$ is
(a) H,
(b) $C_{1-6}$-alkyl,
(c) $C_{3-6}$-cycloalkyl,
(d) aryl, or
(e) benzyl, optionally substituted on the phenyl ring with 1-2 substituents selected from the group consisting of halo, $C_{1-4}$-alkyl, $C_{1-4}$alkoxy or —$NO_2$;

$R^{18}$ is
(a) —$NR^{19}R^{20}$,
(b) —$NHCONH_2$,
(c) —$NHCSNH_2$, or
(d) —$NHSO_2$—$C_6H_5$;

$R^{19}$ and $R^{20}$ are independently
(a) H,
(b) $C_{1-5}$alkyl, or
(c) aryl, $R^{21}$ and $R^{22}$ are independently
(a) $C_{1-4}$-alkyl,
or taken together are
(b) —$(CH_2)_q$—;

$R^{23}$ and $R^{24}$ are, independently
(a) H,
(b) $C_{1-6}$-alkyl,
(c) aryl, or
(d) —($C_{1-4}$-alkyl)-aryl, or
(e) $R^{23}$ and $R^{24}$ when taken together constitute a pyrrolidine, piperidine or morpholine ring;

$R^{25}$ is
(a) H,
(b) $C_{1-6}$-alkyl,
(c) aryl,
(d) —($C_{1-4}$-alkyl)-aryl,
(e) $C_{3-6}$-alkenyl, or
(f) —($C_{3-6}$-alkenyl)-aryl;

$R^{26}$ and $R^{27}$ are independently
(a) H,
(b) $C_{1-4}$-alkyl,
(c) aryl, or
(d) —$CH_2$-aryl;

$R^{28}$ is
(a) aryl, or
(b) heteroaryl;

$R^{29}$ is
(a) —CHO,
(b) —$CONH_2$,
(c) —NHCHO,
(d) —CO—($C_{1-6}$ perfluoroalkyl),
(e) —$S(O)_r$—($C_{1-6}$ perfluoroalkyl),
(f) —O—($C_{1-6}$ perfluoroalkyl), or
(g) —$NR^{11a}$—($C_{1-6}$ perfluoroalkyl);

$R^{30}$ is
(a) —CHO,
(b) —SO$_2$—(C$_1$-C$_6$ perfluoroalkyl), or
(c) —CO—(C$_1$-C$_6$ perfluoroalkyl);

A is
(a) —(CH$_2$)$_n$-L$^1$-B-(T)$_y$-(B)$_y$—X$^2$—(B)$_y$—R$^{28}$,
(b) —(CH$_2$)$_n$-L$^1$-B-T-(B)$_y$—R$^{28}$,
(c) —(CH$_2$)$_n$-L$^1$-B-(T)$_y$-(B)$_y$—X$^2$—B,
(d) —(CH$_2$)$_n$-L$^1$-B-T-(B)$_y$—R$^{29}$,
(e) —(CH$_2$)$_n$-L$^1$-T-(B)$_y$—X$^2$ (B)$_y$—R$^{28}$,
(f) —(CH$_2$)$_n$-L$^1$-T-(B)$_y$—R$^{28}$,
(g) —(CH$_2$)$_n$-L$^1$-T-(B)$_y$—X$^2$—B,
(h) —(CH$_2$)$_n$-L$^1$-(CR$^{19}$R$^{20}$)-D-(T)$_y$-(B)$_y$—X$^3$—(B)$_y$—R$^{28}$,
(i) —(CH$_2$)$_n$-L$^1$-(CR$^{19}$R$^{20}$)-D-T-(B)$_y$—R$^{28}$,
(j) —(CH$_2$)$_n$-L$^1$-(CR$^{19}$R$^{20}$)-D-(T)$_y$-(B)$_y$—X$^3$—B,
(k) —(CH$_2$)$_n$-L$^1$-(CR$^{19}$R$^{20}$)-D-T-(B)$_y$—R$^{29}$,
(l) —(CH$_2$)$_n$-L$^1$-(CR$^{19}$R$^{20}$)-D-T-(B)$_y$—X$^4$—(B)$_y$—R$^{28}$,
(m) —(CH$_2$)$_n$-L$^1$-(CR$^{19}$R$^{20}$)-D-B—X$^4$—(B)$_y$—R$^{28}$,
(n) —(CH$_2$)$_n$-L$^1$-(CR$^{19}$R$^{20}$)-D-T-(B)$_y$—X$^4$—B,
(o) —(CH$_2$)$_n$-L$^1$-(CR$^{19}$R$^{20}$)-D-B—X$^4$—B,
(p) —(CH$_2$)$_n$-L$^2$-B-(T)$_y$-(B)$_y$—X$^2$—(B)$_y$—R$^{28}$,
(q) —(CH$_2$)$_n$-L$^2$-B-T-(B)$_y$—R$^{28}$,
(r) —(CH$_2$)$_n$-L$^2$-B-(T)$_y$-(B)$_y$—X$^2$—B,
(s) —(CH$_2$)$_n$-L$^2$-B-T-(B)$_y$—R$^{29}$,
(t) —(CH$_2$)$_n$-L$^2$-T-(B)$_y$—X$^2$—(B)$_y$—R$^{28}$,
(u) —(CH$_2$)$_n$-L$^2$-T-(B)$_y$—R$^{28}$,
(v) —(CH$_2$)$_n$-L$^2$-T-(B)$_y$—X$^2$—B,
(w) —(CH$_2$)$_n$-L$^2$-D-(T)$_y$-(B)$_y$—X$^3$—(B)$_y$—R$^{28}$,
(x) —(CH$_2$)$_n$-L$^2$-D-T-(B)$_y$—R$^{28}$,
(y) —(CH$_2$)$_n$-L$^2$-D-(T)$_y$-(B)$_y$—X$^3$—B,
(z) —(CH$_2$)$_n$-L$^2$-D-T-(B)$_y$—R$^{29}$,
(aa) —(CH$_2$)$_n$-L$^2$-D-T-(B)$_y$—X$^4$—(B)$_y$—R$^{28}$,
(bb) —(CH$_2$)$_n$-L$^2$-D-B—X$^4$—(B)$_y$—R$^{28}$,
(cc) —(CH$_2$)$_n$-L$^2$-D-T-(B)$_y$—X$^4$—B,
(dd) —(CH$_2$)$_n$-L$^2$-D-B—X$^4$—B,
(ee) —(CH$_2$)$_m$-L$^3$-B-(T)$_y$-(B)$_y$—X$^2$—(B)$_y$—R$^{28}$,
(ff) —(CH$_2$)$_m$-L$^3$-B-T-(B)$_y$—R$^{28}$,
(gg) —(CH$_2$)$_m$-L$^3$-B-(T)$_y$-(B)$_y$—X$^2$—B,
(hh) —(CH$_2$)$_m$-L$^3$-B-T-(B)$_y$—R$^{29}$,
(ii) —(CH$_2$)$_m$-L$^3$-T-(B)$_y$—X$^2$—(B)$_y$—R$^{28}$,
(jj) —(CH$_2$)$_m$-L$^3$-T-(B)$_y$—R$^{28}$,
(kk) —(CH$_2$)$_m$-L$^3$-T-(B)$_y$—X$^2$—B,
(ll) —(CH$_2$)$_m$-L$^3$-(CR$^{19}$R$^{20}$)-D-(T)$_y$-(B)$_y$—X$^3$—(B)$_y$—R$^{28}$,
(mm) —(CH$_2$)$_m$-L$^3$-(CR$^{19}$R$^{20}$)-D-T-(B)$_y$—R$^{28}$,
(nn) —(CH$_2$)$_m$-L$^3$-(CR$^{19}$R$^{20}$)-D-(T)$_y$-(B)$_y$—X$^3$—B,
(oo) —(CH$_2$)$_m$-L$^3$-(CR$^{19}$R$^{20}$)-D-T-(B)$_y$—R$^{29}$,
(pp) —(CH$_2$)$_m$-L$^3$-(CR$^{19}$R$^{20}$)-D-T-(B)$_y$—X$^4$—(B)$_y$—R$^{28}$,
(qq) —(CH$_2$)$_m$-L$^3$-(CR$^{19}$R$^{20}$)-D-(B)—X$^4$—(B)$_y$—R$^{28}$,
(rr) —(CH$_2$)$_m$-L$^3$-(CR$^{19}$R$^{20}$)-D-T-(B)$_y$—X$^4$—B,
(ss) —(CH$_2$)$_m$-L$^3$-(CR$^{19}$R$^{20}$)-D-B—X$^4$—B,

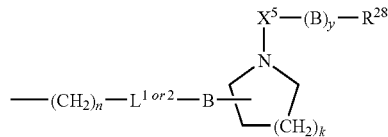
(tt)

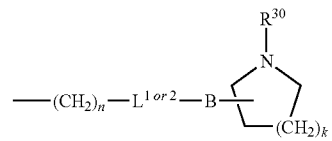
(uu)

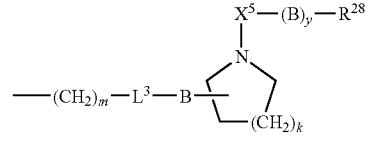
(vv)

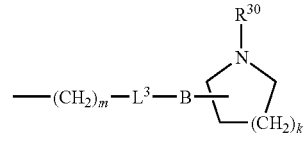
(ww)

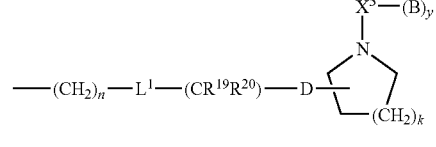
(xx)

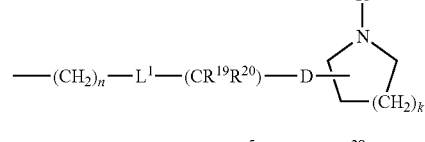
(yy)

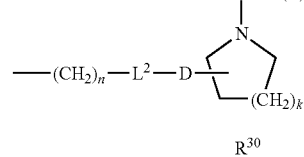
(zz)

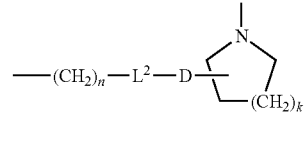
(aaa)

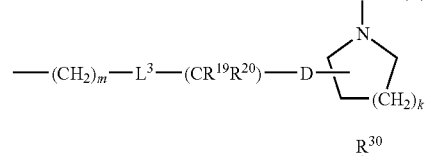
(bbb)

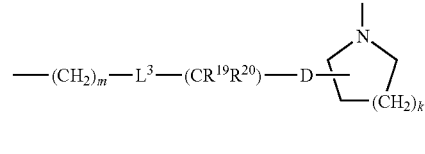
(ccc)

L$^1$ is
(a) —CO$_2$—,
(b) —CONR$^{11a}$—,
(c) —NR$^{11a}$CO$_2$—, or
(d) —NR$^{11a}$CONR$^{11b}$—;

L$^2$ is
(a) —CO—,
(b) NR$^{11a}$CO—, or
(c) —O$_2$C—;

L³ is
(a) —O—,
(b) —SO—, or
(c) —NR¹¹ᵃ—;
B is $C_{1-6}$ alkyl;
D is $C_{2-8}$ alkenyl or $C_{2-8}$ alkynyl;
T is
(a) arylene, or
(b) heteroarylene
X¹ is
(a) a carbon-carbon single bond,
(b) —CO—,
(c) —C(R¹⁹)(R²⁰)—,
(d) —O—,
(e) —S—,
(f) —SO—,
(g) —SO₂—,
(h) —NR¹⁴—,
(i) —CONR¹⁶—,
(j) —R¹⁶CO—,
(k) —OC(R¹⁹)(R²⁰)—,
(l) —C(R¹⁹)(R²⁰)O—,
(m) —SC(R¹⁹)(R²⁰)—,
(n) —C(R¹⁹)(R²⁰)S—,
(o) —NHC(R¹⁹)(R²⁰)—,
(p) —C(R¹⁹)(R²⁰)NH—,
(q) —NR¹⁶SO₂—,
(r) —SO₂NR¹⁶—,
(s) —CH=CH—,
(t) —CF=CF—,
(u) —CF=CH—,
(v) —CH=CF—,
(w) —CF₂CF₂—,
(x) —CH(OR¹⁵)—,
(y) —CH(OCOR¹⁷)—,
(z) —C(=NR¹⁸)—,
(aa) —C(OR²¹)(OR²²)—,
(bb) 1,2-cyclopropyl, or
(cc) 1,1-cyclopropyl;
X² is
(a) —CO—,
(b) —O—,
(c) —S(O)ᵣ—,
(d) —(C₁₋₄-alkylene)-,
(e) —NR¹¹ᵃCONR¹¹ᵇ—,
(f) —CONR¹¹ᵃ—,
(g) —NR¹¹ᵃCO—,
(h) —SO₂NR¹⁶—,
(i) —NR¹⁶SO₂—,
(j) —OCONR¹¹ᵃSO₂—,
(k) —SO₂NR¹¹ᵃCO—,
(l) —SO₂NR¹¹ᵃCO—,
(m) —OCONR¹¹ᵃSO₂—,
(n) —SO₂NR¹¹ᵃCONR¹¹ᵇ—,
(o) —NR¹¹ᵃCONR¹¹ᵇSO₂—,
(p) —SO₂NR¹¹ᵃSO₂—,
(q) —ONR¹¹ᵃSO₂NR¹¹ᵇ—, or
(r) —NR¹¹ᵃ SO₂NR¹¹ᵇCO—;
X³ is
(a) —C—,
(b) —SO—,
(c) —SO₂—,
(d) single bond,
(e) —CONR¹¹ᵃ—,
(f) —SO₂NR¹⁶—,
(g) —CONR¹¹ᵃSO₂—,
(h) —SO₂NR¹¹ᵃCO—, (i) —SO₂NR¹¹ᵃCO₂—,
(j) —SO₂ NR¹¹ᵃCONR¹¹ᵇ—,
(k) —SO₂ NR¹¹ᵃ SO₂—, or
(l) —CONR¹¹ᵃ SO₂ NR¹¹ᵇ—;
X⁴ is
(a) —NR¹¹ᵃCONR¹¹ᵇ—,
(b) —OCONR¹¹ᵃSO₂—,
(c) —NR¹⁶SO₂—,
(d) —OCONR¹¹ᵃSO₂—,
(e) —NR¹¹ᵃCONR¹¹ᵇSO₂—, or
(f) —NR¹¹ᵃSO₂NR¹¹ᵇCO—;
X⁵ is
(a) —CO—,
(b) —SO₂—,
(c) —COO—, or
(d) —CONR¹¹ᵃ—;
Z is
(a) —O—,
(b) —S—, or
(c) —NR¹¹—;
k is 1 or 2;
m is 1 to 5;
n is 0 to 2;
q is 2 to 3;
r is 0 to 2;
s is 0 to 5;
t is 0 to 3;
u is 2 to 5;
y is 0 or 1;
and pharmaceutically compatible salts of these compounds.

In specific embodiments, the above compounds are those of formula (VI) wherein
A is
(a) —(CH₂)ₙ-L¹-S-(T)ᵧ-(S)ᵧ—X²—(S)ᵧ—R²⁸,
(b) —(CH₂)ₙ-L¹-B-T-(B)ᵧ—R²⁸,
(c) —(CH₂)ₙ-L¹-B-T-(B)ᵧ—X²—B,
(d) —(CH₂)ₙ-L¹-B-T-(B)ᵧ—R²⁹
(e) —(CH₂)ₙ-L²-B-(T)ᵧ-(B)ᵧ—X²—(B)ᵧ—R²⁸,
(f) —(CH₂)ₙ-L²-B-T-(B)ᵧ—R²⁸, or
(g) —(CH₂)ₙ-L²-B-(T)ᵧ-(B)ᵧ—X²—B,
(h) —(CH₂)ₙ-L²-B-T-(B)ᵧ—R²⁹;

An illustrative example of the specific embodiments described above is a compound of formula (VIa)

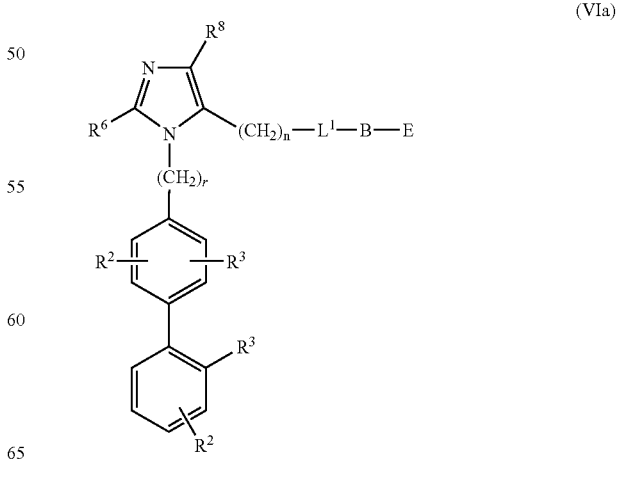

wherein:
R² is independently
(a) H,
(b) halo (F, Cl, Br, I), or
(c) $C_{1-4}$-alkyl;
R³ is
(a) H, or
(b) halo (F, Cl, Br, I);
R⁶ is
(a) $C_{1-10}$ alkyl,
(b) $C_{3-10}$ alkenyl, or
(c) $C_{3-10}$ alkynyl;
R⁹ is
(a) H,
(b) $C_{1-5}$-alkyl,
(c) aryl,
(d) —($C_{1-4}$-alkyl)-aryl, or
(e) heteroaryl;
R¹⁰ is
(a) aryl,
(b) $C_{3-7}$-cycloalkyl,
(c) $C_{1-4}$perfluoroalkyl,
(d) $C_{1-4}$-alkyl, optionally substituted with a substituent selected from the group consisting of aryl, heteroaryl, —OH, —SH, $C_{1-4}$-alkyl, $C_{1-4}$-alkoxy, $C_{1-4}$-alkylthio, —CF₃, halo, —NO₂, —CO₂ R¹², —NH₂, $C_{1-4}$-alkylamino, $C_{1-4}$-dialkylamino, —PO₃H₂, or
(e) heteroaryl;
R¹¹, R¹¹ᵃ and R¹¹ᵇ are independently
(a) H,
(b) $C_{1-6}$-alkyl,
(c) $C_{3-6}$-cycloalkyl,
(d) aryl,
(e) —($C_{1-5}$-alkyl)-aryl, or
(f) heteroaryl;
R¹³ is
(a) —CO₂H,
(b) —CONHSO₂R¹⁰,
(c) —CONHSO₂NHR⁹,
(d) —NHCONHSO₂ R¹⁰,
(e) —NHSO₂R¹⁰,
(f) —NHSO₂NHCOR¹⁰,
(g) —SO₂NHR⁹,
(h) —SO₂NHCOR¹⁰,
(i) —SO₂NHCONHR⁹,
(j) —SO₂NHCO₂R¹⁰, or (k)

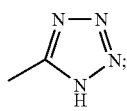

R¹⁶ is
(a) H,
(b) $C_{1-6}$-alkyl, or
(c) benzyl, optionally substituted on the phenyl ring with 1-2 substituents selected from the group consisting of halo, $C_{1-4}$-alkyl, $C_{1-4}$-alkoxy or —NO₂;
R²⁸ is
(a) aryl, or
(b) heteroaryl;
R²⁹ is
(a) —CHO,
(b) —CONH₂,
(c) —NHCHO, (d) —CO—($C_{1-6}$ perfluoroalkyl),
(e) —S(O)ᵣ—($C_{1-6}$ perfluoroalkyl),
E is
(a) -(T)ᵧ-(B)ᵧ—X²—(B)ᵧ—R²⁸,
(b) -T-(B)ᵧ—R²⁸,
(c) -(T)ᵧ-(B)ᵧ—X²—B or,
(d) -T-(B)ᵧ—R²⁹;
L¹ is
(a) —CO₂—,
(b) —CONR¹¹ᵃ—,
(c) —NR¹¹ᵃCO₂—,
(d) —NR¹¹ᵃCONR¹¹ᵇ—;
B is $C_1$-$C_6$ alkyl;
X² is
(a) —CO—,
(b) —O—,
(c) —S(O)ᵣ—,
(d) —($C_1$-$C_4$-alkylene)-,
(e) —R¹¹ᵃCONR¹¹ᵇ—,
(f) —CONR¹¹ᵃ—,
(g) —NR¹¹ᵃCO—,
(h) —SO₂NR¹⁶—,
(i) —NR¹⁶SO₂—,
(j) —CONR¹¹ᵃSO₂—,
(k) —SO₂NR¹¹ᵃCO—,
(l) —SO₂NR¹¹ᵃCO₂—,
(m) —OCONR¹¹ᵃSO₂—,
(n) —SO₂NR¹¹ᵃCONR¹¹ᵇ—,
(o) —NR¹¹ᵃCONR¹¹ᵇSO₂—,
(p) —SO₂NR¹¹ᵃSO₂—,
(q) —CONR¹¹ᵃSO₂NR¹¹ᵇ—, or
(r) —NR¹¹ᵃSO₂NR¹¹ᵇCO— and pharmaceutically compatible salts of these compounds.

Another illustrative example of the specific embodiments described above is a compound of formula (VIb)

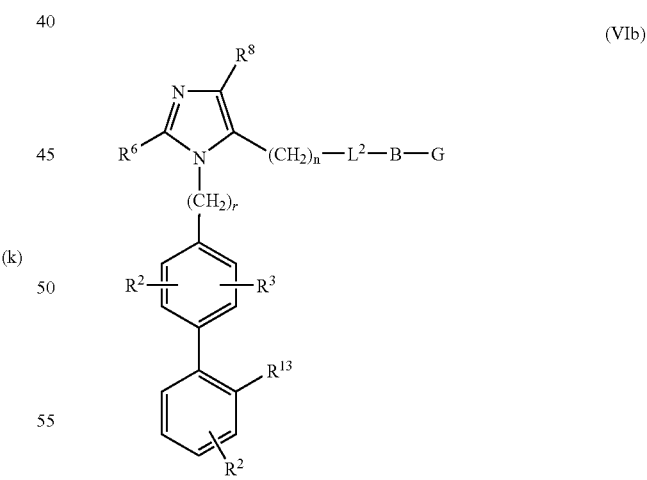

(VIb)

wherein:
R² is independently
(a) H,
(b) halo (F, Cl, Br, I), or
(c) $C_{1-4}$-alkyl;
R³ is
(a) H, or
(b) halo (F, Cl, Br, I);

R⁶ is
(a) $C_{1-10}$ alkyl,
(b) $C_{3-10}$ alkenyl, or
(c) $C_{3-10}$ alkynyl;
R⁹ is
(a) H,
(b) $C_{1-5}$-alkyl,
(c) aryl
(d) —($C_{1-4}$-alkyl)-aryl, or
(e) heteroaryl;
R¹⁰ is
(a) aryl,
(b) $C_{3-7}$-cycloalkyl,
(c) $C_{1-4}$-perfluoroalkyl,
(d) $C_{1-4}$-alkyl, optionally substituted with a substituent selected from the group consisting of aryl, heteroaryl, —OH, —SH, $C_{1-4}$-alkyl, $C_{1-4}$-alkoxy, $C_{1-4}$-alkylthio, —CF₃, halo, —NO₂, —CO₂R¹², —NH₂, $C_{1-4}$-alkylamino, $C_{1-4}$-dialkylamino, —PO₃H₂, or
(e) heteroaryl;
R¹¹, R¹¹ᵃ and R¹¹ᵇ are independently
(a) H,
(b) $C_{1-6}$-alkyl,
(c) $C_{3-6}$-cycloalkyl,
(d) aryl,
(e) —($C_{1-5}$-alkyl)-aryl, or
(f) heteroaryl;
R¹³ is
(a) —CO₂H,
(b) —CONHSO₂R¹⁰,
(c) —CONHSO₂NHR⁹,
(d) —NHCONHSO₂R¹⁰,
(e) —NHSO₂R¹⁰,
(f) —NHSO₂NHCOR¹⁰,
(g) —SO₂NHR⁹,
(h) —SO₂NHCOR¹⁰,
(i) —SO₂NHCONHR⁹,
(j) —SO₂NHCO₂R¹⁰, or

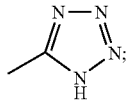 (k)

R¹⁶ is
(a) H,
(b) $C_{1-6}$-alkyl, or
(c) benzyl, optionally substituted on the phenyl ring with 1-2 substituents selected from the group consisting of halo, $C_{1-4}$-alkyl, $C_{1-4}$-alkoxy or —NO₂;
R²⁸ is
(a) aryl, or
(b) heteroaryl;
R²⁹ is
(a) —CHO,
(b) —CONH₂,
(c) —HCHO,
(d) —CO—($C_1$-$C_6$ perfluoroalkyl),
(e) —S(O)ᵣ—($C_1$-$C_6$ perfluoroalkyl),
G is
(a) -(T)ᵧ-(B)ᵧ—X²—(B)ᵧ—R²⁸,
(b) -T-(B)ᵧ—R²⁸,
(c) -(T)ᵧ-(B)ᵧ—X²—B, or
(d) -T-(B)ᵧ—R²⁹;

L² is —CO—, —NR¹¹ᵃCO— or —O₂C—;
B is $C_{1-6}$ alkyl;
X₂ is
(a) —CO—,
(b) —O—,
(c) —S(O)ᵣ—,
(d) —($C_{2-4}$-alkylene)-,
(e) —NR¹¹ᵃ CO, —NR¹¹ᵃCONR¹¹ᵇ—
(f) —CONR¹¹ᵃ—,
(g) —NR¹¹ᵃCO—,
(h) —SO₂NR¹⁶—,
(i) —NR¹⁶SO₂—,
(j) —O₂NR¹¹ᵃSO₂—,
(k) —SO₂NR¹¹ᵃCO₂—,
(l) —SO₂NR¹¹ᵃCO₂—,
(m) —OCONR¹¹ᵃSO₂—,
(n) —SO₂NR¹¹ᵃCONR¹¹ᵇ—,
(o) —N^{R11a}CONR¹¹ᵇSO₂—,
(p) —SO₂NR¹¹ᵃSO₂—,
(q) —CONR¹¹ᵃSO₂NR¹¹ᵇ—, or
(r) —NR¹¹ᵃSO₂NR¹¹ᵇCO—, and pharmaceutically compatible salts of these compounds.

Illustrative of the compounds according to the specific embodiments mentioned above are the following:

1-[[2'-[[(isopentoxycarbonyl)amino]sulfonyl]-3-fluoro(1,1'-biphenyl)-4-yl]methyl]-5-13-(N-pyridin-3 ylbutanamido)propanoyl]-4-ethyl-2-propyl-1H-imidazole (XR510);

1-((2'-((1-Amyloxycarbonylamino)sulfonyl)-3-fluoro-(1,1'-biphenyl)-4-yl)methyl)-5-[2-(N-benzoyl-N-phenylamino)ethylcarbonyl]-4-ethyl-2-propyl-1H-imidazole;

1-((2'-((n-Butyloxycarbonylamino)sulfonyl)-3-fluoro-(1,1'-biphenyl)-4-yl)methyl)-5-[2-(N-benzoyl-N-phenylamino)ethylcarbonyl]-4-ethyl-2-propyl-1H-imidazole;

1-((2'-((n-Propyloxycarbonylamino)sulfonyl)-3-fluoro-(1,1'-biphenyl)-4-yl)methyl)-5-[2-(N-benzoyl-N-phenylamino)ethylcarbonyl]-4-ethyl-2-propyl-1H-imidazole;

1-((2'-((n-Butyloxycarbonylamino)sulfonyl)-3-fluoro-(1,1'-biphenyl)-4-yl)methyl)-5-[2-(N-benzoyl-N-butylamino)ethylcarbonyl]-4-ethyl-2-propyl-1H-imidazole;

1-((2'-((n-Butyloxycarbonylamino)sulfonyl)-3-fluoro-(1,1'-biphenyl)-4-yl)methyl)-5-[2-(N-benzoyl-N-propylamino)ethylcarbonyl]-4-ethyl-2-propyl-1H-imidazole;

1-((2'-((n-Butyloxycarbonylamino)sulfonyl)-3-fluoro-(1,1'-biphenyl)-4-yl)methyl)-5-[2-(N-butyryl-N-propylamino)ethylcarbonyl]-4-ethyl-2-propyl-1H-imidazole;

1-((2'-((n-Butyloxycarbonylamino)sulfonyl)-3-fluoro-(1,1'-biphenyl)-4-yl)methyl)-5-[2-(N-butyryl-N-phenylamino)ethylcarbonyl]-4-ethyl-2-propyl-1H-imidazole;

1-((2'-((1-Amyloxycarbonylamino)sulfonyl)-3-fluoro-(1,1'-biphenyl)-4-yl)methyl)-5-[2-(N-butyryl-N-phenylamino)ethylcarbonyl]-4-ethyl-2-propyl-1H-imidazole;

1-((2'-((1-Amyloxycarbonylamino)sulfonyl)-3-fluoro-(1,1'-biphenyl)-4-yl)methyl)-5-[2-(N-isonicotinoyl-N-pyridin-3-ylamino)ethylcarbonyl]-4-ethyl-2-propyl-1H-imidazole;

1-((2'-((n-Butyloxycarbonylamino)sulfonyl)-3-fluoro-(1,1'-biphenyl)-4-yl)methyl)-5-[2-(N-isonicotinoyl-N-pyridin-3-ylamino)ethylcarbonyl]-4-ethyl-2-propyl-1H-imidazole;

1-((2'-((n-Butyloxycarbonylamino)sulfonyl)-3-fluoro-(1,1'-biphenyl)-4-yl)methyl)-5-[2-(N-nicotinoyl-N-pyridin-3-ylamino)ethylcarbonyl]-4-ethyl-2-propyl-1H-imidazole;

1-((2'-((1-Amyloxycarbonylamino)sulfonyl)-3-fluoro-(1,1'-biphenyl)-4-yl)methyl)-5-[2-(N-nicotinoyl-N-pyridin-3-ylamino)ethylcarbonyl]-4-ethyl-2-propyl-1H-imidazole;

1-((2'-((1-Amyloxycarbonylamino)sulfonyl)-3-fluoro-(1,1'-biphenyl)-4-yl)methyl)-5-[2-(N-nicotinoyl-N-pyridin-2-ylamino)ethylcarbonyl]-4-ethyl-2-propyl-1H-imidazole;

1-((2'-((1-Amyloxycarbonylamino)sulfonyl)-3-fluoro-(1,1'-biphenyl)-4-yl)methyl)-5-[2-(N-isonicotinoyl-N-phenylamino)ethylcarbonyl]-4-ethyl-2-propy 1-1H-imidazole;

1-((2'-((1-Amyloxycarbonylamino)sulfonyl)-3-fluoro-(1,1'-biphenyl)-4-yl)methyl)-5-[2-(N-butyryl-N-pyridin-3-ylamino)ethylcarbonyl]-4-ethyl-2-propyl-1H-imidazole;

1-((2'-((1-Amyloxycarbonylamino)sulfonyl)-3-fluoro-(1,1'-biphenyl)-4-yl)methyl)-5-[2-(N-isobutyryl-N-pyridin-3-ylamino)ethylcarbonyl]-4-ethyl-2-propyl-1H-imidazole;

1-((2'-((n-Butyloxycarbonylamino)sulfonyl)-3-fluoro-(1,1'-biphenyl)-4-yl)methyl)-5-[2-(N-acetyl-N-pyridin-3-ylamino)ethylcarbonyl]-4-ethyl-2-propyl-1H-imidazole;

1-((2'-((1-Amyloxycarbonylamino)sulfonyl)-3-fluoro-(1,1'-biphenyl)-4-yl)methyl)-5-[2-(N-butyryl-N-pyridin-2-ylamino)ethylcarbonyl]-4-ethyl-2-propyl-1H-imidazole 1-((2'-((1-Amyloxycarbonylamino)sulfonyl)-(1,1'-biphenyl)-4-yl)methyl)-5-[2-(N-butyryl-N-pyridin-3-ylamino)ethylcarbonyl]-2-butyl-4-chloro-1H-imidazole;

1-((2'-((1-amyloxycarbonylamino)sulfonyl)-3-fluoro-(1,1'-biphenyl)-4-yl)methyl)-5-[2-(N-propionyl-N-pyridin-3-ylamino)ethylcarbonyl]-4-ethyl-2-propyl-1H-imidazole;

1-((2'-((1-Amyloxycarbonylamino)sulfonyl)(1,1'-biphenyl)-4-yl)methyl)-5-[2-(N-nicotinoyl-N-pyridin-3-ylamino)ethylcarbonyl]-4-ethyl-2-propyl-1H-imidazole;

1-((2'-((i-Amyloxycarbonylamino)sulfonyl)(1,1'-biphenyl)-4-yl)methyl)-5-[2(N-butyryl-N-pyridin-3-ylamino)ethylcarbonyl]-4-ethyl-2-propyl-1H-imidazole;

1-((2'-((n-Butyloxycarbonyl-amino)sulfonyl)-3-fluoro-(1,1'-biphenyl)-4-yl)methyl)-4-ethyl-5-(2-(2-phenoxyphenyl)ethylcarbonyl)-2-propyl-1H-imidazole;

4-[((5-(2-Benzoylbenzyloxycarbonyl)-4-ethyl-2-n-propyl)imidazol-1-yl)methyl]-3-fluoro-2'-n-butyloxycarbonylaminosulfonyl-1,1'-biphenyl;

4-[((5-(2-Benzoylbenzyloxycarbonyl)-4-ethyl-2-n-propyl)imidazol-1-yl)methyl]-3-fluoro-2'-((2-phenyl)ethyloxycarbonylaminosulfonyl)-1,1'-biphenyl;

4-[((5-(2-Benzoylbenzyloxycarbonyl)-4-ethyl-2-n-propyl)imidazol-1-yl)methyl]-2'-((2-phenyl)ethyloxycarbonylaminosulfonyl)-1,1'-biphenyl;

4-[((5-(2-Benzoylbenzyloxycarbonyl)-4-ethyl-2-n-propyl)imidazol-1-yl)methyl]-3-fluoro-2'-n-butyloxycarbonylaminosulfonyl-1,1'-biphenyl;

4-[((5-(2-Benzoylbenzyloxycarbonyl)-4-ethyl-2-n-propyl)imidazol-1-yl)methyl]-3-fluoro-2'-n-isoamyloxycarbonylaminosulfonyl-1,1'-biphenyl;

4-[((5-(2-Benzoylbenzyloxycarbonyl)-4-ethyl-2-n-propyl)imidazol-1-yl)methyl]-2'-n-isoamyloxycarbonylaminosulfonyl-1,1'-biphenyl;

4-[((5-(2-Benzoylbenzyloxycarbonyl)-4-ethyl-2-n-propyl)imidazol-1-yl)methyl]-3-fluoro-2'-n-propyloxycarbonylaminosulfonyl-1,1'-biphenyl;

4-[((5-(2-Isoamyloxybenzyloxycarbonyl)-4-ethyl-2-n-propyl)imidazol-1-yl)methyl]-3-fluoro-2'-n-butyloxycarbonylaminosulfonyl-1,1'-biphenyl;

4-[((5-(2-Phenylaminocarbonyl)benzyloxycarbonyl-4-ethyl-2-n-propyl)imidazol-1-yl)methyl]-3-fluoro-2'-n-butyloxycarbonylaminosulfonyl-1,1'-biphenyl;

4-[((5-(2-Benzoylbenzyloxycarbonyl)-4-ethyl-2-n-propyl)imidazol-1-yl)methyl]-3-fluoro-2'41H-tetrazol-5-yl)-1,1'-biphenyl;

4-[((5-)-2-trifluorophenyl)methylaminocarbonyl)-4-ethyl-2-n-propyl)imidazol-1-yl)methyl]-3-fluoro-2'-isoamyloxycarbonylaminosulfonyl-1,1'-biphenyl;

N-butyl, N-benzyl-2-(aminocarbonyl)ethynylmethyl 4-ethyl-2-propyl-1-[[2'-(1H-tetrazol-5-yl)biphenyl-4-yl]methyl]imidazole-5-carboxylate;

N,N-diphenyl-2-(aminocarbonyl)ethynylmethyl 4-ethyl-2-propyl-1-[[2'-(1H-tetrazol-5-yl)biphenyl-4-yl]methyl]imidazole-5-carboxylate;

N-phenyl-2-(aminocarbonyl)ethyl-4-ethyl-2-propyl-1-[[2'-(1H-tetrazol-5-yl)biphenyl-4-yl]methyl]imidazole-5-carboxylate, N-butyl, N-benzyl-4-(aminocarbonyl)propyl-4-ethyl-2-propyl-1-[[2'-(1H-tetrazol-5-yl)biphenyl-4-yl]methyl]imidazole-5-carboxylate;

N,N-dipentyl-4-(aminocarbonyl)propyl 4-ethyl-2-propyl-1-[[2'-(tetrazol-5-yl)biphenyl-4-yl]methyl]imidazole-5-carboxylate;

4-[(5-((2-benzoyl)phenylcarbonyloxymethyl)-4-chloro-2-n-propyl imidazol-1-yl)methyl]-3-fluoro-2'-isoamyloxycarbonylaminosulfonylbiphenyl; and 1-((2'-((n-butyloxycarbonylamino)sulfonyl)-3-fluoro-(1,1'-biphenyl)-4-yl)methyl)-2-(n-propyl)-4-ethyl-5-(2-(phenoxy)phenoxy)acetyl-1H-imidazole.

In the embodiments described above for compounds according to formulae (VI)-(VIb), when an alkyl substituent is mentioned, the normal alkyl structure is meant (e.g. butyl is n-butyl) unless otherwise specified. However, in the definition of radicals above (e.g. $R^3$), both branched and straight chains are included in the scope of alkyl, alkenyl and alkynyl.

In the embodiments described above for compounds according to formulae (VI)-(VIb), the term "aryl" is meant to include phenyl, biphenyl, napthyl, or fluorenyl group optionally substituted with one to three substituents selected from the group consisting of —OH, —SH, $C_1$-$C_4$-alkyl, $C_1$-$C_4$-alkoxy, —$CF_3$, halo, —$NO_2$, —$CO_2H$, —$CO_2CH_3$, —$CO_2$-benzyl, —$NH_2$, —NH($C_1$-$C_4$-alkyl), —N($C_1$-$C_4$-alkyl)$_2$.

The term heteroaryl is meant to include unsubstituted, monosubstituted or disubstituted 5- to 10-membered mono- or bicyclic aromatic rings which can optionally contain from 1 to 3 heteroatoms selected from the group consisting of O, N, and S. Included in the definition of the group heteroaryl, but not limited to, are the following: pyridyl, pyridazinyl, pyrimidinyl, pyrazinyl, 1,3,5-triazinyl, furyl, thiophenyl, imidazolyl, oxazolyl, thiazolyl, benzofuranyl, benzothiophenyl, benzimidazolyl, benzoxazolyl, benzothiazolyl, indolin-2-onyl, indolinyl, indolyl, pyrrolyl, quinonlinyl and isoquinolinyl. Particularly preferred are 2-, 3-, or 4-pyridyl; 2-, or 3-furyl; 2-, or 3-thiophenyl; 2-, 3-, or 4-quinolinyl; or 1-, 3-, or 4-isoquinolinyl optionally substituted with one to three substituents selected from the group consisting of —OH, —SH, $C_1$-$C_4$-alkoxy, —$CF_3$, halo, —$NO_2$, —$CO_2H$, —$CO_2CH_3$, —$CO_2$-benzyl, —$NH_2$, —NH($C_1$-$C_4$-alkyl), —N($C_1$-$C_4$-alkyl)$_2$. The term arylene is meant to include a phenyl, biphenyl, napthyl, or fluorenyl group which is used as a link for two groups to form a chain. Included in the definition of arylene, but not limited to, are the following isomeric linkers: 1,2-phenyl, 1,3-phenyl, 1,4-phenyl; 4,4'-biphenyl, 4,3'-biphenyl, 4,2'-biphenyl, 2,4'-biphenyl, 2,3'-biphenyl, 2,2'-biphenyl, 3,4'-biphenyl, 3,3'-biphenyl, 3,2'-biphenyl, 1,2-napthyl, 1,3-napthyl, 1,4-napthyl, 1,5-napthyl, 1,6-napthyl, 1,7-napthyl, 1,8-napthyl, 2,6-napthyl, 2,3-napthyl; 1,4-fluorenyl. Particularly preferred are 1,2-phenyl, 1,3-phenyl, 1,4-phenyl, 4,4'-biphenyl, 3,3'-biphenyl, and 2,2'-biphenyl optionally substituted with one to three substituents selected from the group consisting of —OH, —SH, $C_1$-$C_4$-alkoxy, —$CF_3$, halo, —$NO_2$, —$CO_2H$, —$CO_2CH_3$, —$CO_2$-benzyl, —$NH_2$, —NH($C_1$-$C_4$-alkyl), —N($C_1$-$C_4$-alkyl)$_2$.

In the embodiments described above for compounds according to formulae (VI)-(VIb), the term heteroarylene is meant to include unsubstituted 5- to 10-membered aromatic ring which can optionally contain from 1 to 3 heteroatoms selected from the group consisting of O, N, and S which is used as a link for two groups to form a chain. Included in the definition of the group heteroaryl, but not limited to, are the following: 2,3-pyridyl, 2,4-pyridyl, 2,5-pyridyl, 2,6-pyridyl, 3,4-pyridyl, 3,5-pyridyl, 3,6-pyridyl; 2,3-furyl, 2,4-furyl, 2,5-furyl; 2,3-thiophenyl, 2,4-thiophenyl, 2,5-thiophenyl; 4,5-imidazolyl, 4,5-oxazolyl; 4,5-thiazolyl; 2,3-benzofuranyl; 2,3-benzothiophenyl; 2,3-benzimidazolyl; 2,3-benzoxazolyl; 2,3-benzothiazolyl; 3,4-indolin-2-onyl; 2,4-indolinyl; 2,4-indolyl; 2,4-pyrrolyl; 2,4-quinolinyl, 2,5-quinolinyl, 4,6-quinolinyl; 3,4-isoquinolinyl, 1,5-isoquinolinyl. Particularly preferred are 2,3-pyridyl, 3,4-pyridyl, 2,3-furyl, 3,4-furyl 2,3-thiophenyl, 3,4-thiophenyl, 2,3-quinolinyl, 3,4-quinolinyl and 1,4-isoquinolinyl optionally substituted with one to three substituents selected from the group consisting of —OH, —SH, $C_1$-$C_4$-alkyl, $C_1$-$C_4$-alkoxy, —$CF_3$, halo, —$NO_2$, —$CO_2H$, —$CO_2CH_3$, —$CO_2$-benzyl, —$NH_2$, —NH($C_1$-$C_4$-alkyl), —N($C_1$-$C_4$-alkyl)$_2$;

It should be noted in the foregoing structural formula, when a radical can be a substituent in more than one previously defined radical, that first radical ($R^{\#}$, B or y) can be selected independently in each previously defined radical. For example, $R^1$ and $R^2$ can each be —$CONHOR^{12}$. $R^{12}$ need not be the same substituent in each of $R^1$ and $R^2$, but can be selected independently for each of them. Or if, for example, the same R group (let us take $R^2$, for instance) appears twice in a molecule, each of those R groups is independent of each other (one $R^2$ group may be —$CONHOR^{12}$, while the other $R^2$ group may be —CN).

In still other embodiments, the $AT_2$ receptor antagonist is selected from the compounds listed in U.S. Pat. No. 5,338,740 and especially in the compound claims of this patent, which a heterocyclic ring (hereafter referred to as "Het") is connected to an aryl or thienyl group (hereafter referred to as "Ar") via a carbobicyclic or heterobicyclic spacer group (hereafter referred to as "W"). Representative examples of such compounds are represented by the formula (VII):

Ar—W-Het  (VII)

wherein:
Ar is selected from the group consisting of

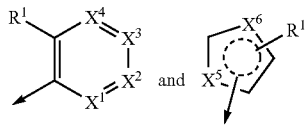

and $X^1$, $X^2$, $X^3$ and $X^4$ are independently selected from $CR^2$ and nitrogen;
one of $X^5$ and $X^6$ is CH and the other is S;
$R^1$ is selected from the group consisting of $CO_2H$, —$NHSO_2CF_3$, —$CONHSO_2$—($C_1$-$C_8$)alkyl, $PO_3H_2$, $SO_3H$, —$CONHSO_2(C_6H_5)$, —$CONHSO_2CF_3$, tetrazole,

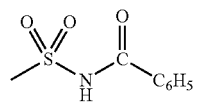

and —$SO_2NHCO_2$—($C_1$-$C_8$)alkyl;

$R^2$ is selected from hydrogen, ($C_1$-$C_8$)alkyl, ($C_2$-$C_{10}$)alkenyl, ($C_3$-$C_8$)cycloalkyl, halo, hydroxy, —S—($C_1$-$C_6$)alkyl, —SO—($C_1$-$C_6$)alkyl —$SO_2$—($C_1$-$C_6$)alkyl, —$NR^3R^4$, and phenyl, wherein said phenyl is optionally mono-, di- or tri-substituted with substituents independently selected from hydrogen, ($C_1$-$C_8$)alkyl, ($C_2$-$C_{10}$)alkenyl, ($C_3$-$C_8$)cycloalkyl, halo, ($C_1$-$C_6$)alkoxy, —S—($C_1$-$C_6$)alkyl, —SO—($C_1$-$C_6$)alkyl, —$SO_2$—($C_1$-$C_6$)alkyl, —O—($C_1$-$C_6$)alkyl, and —$NR^3R^4$;

$R^3$ and $R^4$ are independently selected from hydrogen, ($C_1$-$C_8$)alkyl, ($C_2$-$C_{10}$)alkenyl and ($C_3$-$C_8$)cycloalkyl, or $R^3$ and $R^4$, together with the nitrogen to which they are attached, form a cyclic 5-7 membered saturated or partially saturated carbocyclic or heterocyclic ring with one or two heteroatoms independently selected from nitrogen, oxygen and sulfur; and the dotted line represents that the ring containing $X^5$ and $X^6$ is aromatic:

W is a carbobicyclic or heterobicyclic ring system having the formula:

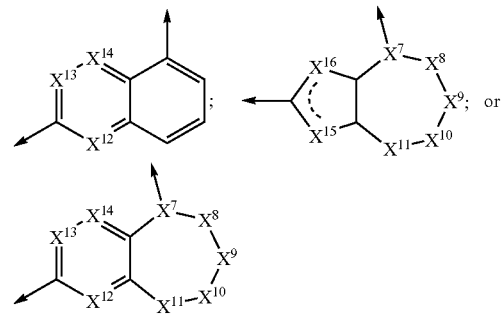

and $X^8$, $X^9$, $X^{10}$ and $X^{11}$ are present or absent, and each of $X^7$, $X^8$, $X^9$, $X^{10}$ and $X^{11}$ is independently selected from $CHR^5$, O, S, SO, $SO^2$, and $NR^6$;

$X^{12}$, $X^{13}$, and $X^{14}$ are independently selected from $CR^7$ or N;

$X^{15}$ and $X^{16}$ are independently selected from $CR^7$ and S;

$R^5$ is absent when the CH moiety of $CHR^5$ is connected to Het and when $R^5$ is present it is selected from hydrogen, ($C_1$-$C_8$)alkyl, ($C_2$-$C_{10}$)alkenyl, ($C_3$-$C_8$)cycloalkyl, —O—($C_1$-$C_6$)alkyl, and phenyl, wherein said phenyl is optionally mono-, di- or tri-substituted with substituents independently selected from hydrogen, ($C_1$-$C_8$)alkyl, ($C_2$-$C_{10}$)alkenyl, ($C_3$-$C_8$)cycloalkyl, halo, ($C_1$-$C_6$)alkoxy, —S—($C_1$-$C_6$)alkyl, —SO—($C_1$-$C_6$)alkyl, —$SO_2$—($C_1$-$C_6$)alkyl, —O—($C_1$-$C_6$)alkyl, and —$NR^3R^4$;

$R^6$ is selected from ($C_1$-$C_8$)alkyl, ($C_3$-$C_8$)cycloalkyl and phenyl, wherein said cycloalkyl is saturated or partially saturated and wherein said cycloalkyl may optionally contain a heteroatom selected from nitrogen, oxygen, and sulfur, and said phenyl is optionally mono-, di- or tri-substituted with substituents independently selected from hydrogen, ($C_1$-$C_8$)alkyl, ($C_1$-$C_{10}$)alkenyl, ($C_3$-$C_8$)cycloalkyl, halo, ($C_1$-$C_6$)alkoxy, —S—($C_1$-$C_6$)alkyl, —SO—($C_1$-$C_6$)alkyl, —$SO_2$—($C_1$-$C_6$)alkyl, —O—($C_1$-$C_6$)alkyl, and —$NR^3R^4$;

$R^7$ is selected from hydrogen, ($C_1$-$C_8$)alkyl, ($C_2$-$C_{10}$)alkenyl, ($C_3$-$C_8$)cycloalkyl, halo, hydroxy, —O—($C_1$-$C_6$)alkyl, —S—($C_1$-$C_6$)alkyl, SO—($C_1$-$C_6$)alkyl, —$SO_2$—($C_1$-$C_6$)alkyl, —$NR^3R^4$, and phenyl, wherein said phenyl is optionally mono-, di- or tri-substituted with substituents selected from hydrogen, ($C_1$-$C_8$)alkyl, ($C_1$-

$C_{10}$)alkenyl, ($C_3$-$C_8$)cycloalkyl, halo, ($C_1$-$C_6$)alkoxy, —S—($C_1$-$C_6$)alkyl, —SO—($C_1$-$C_6$)alkyl, —$SO_2$—($C_1$-$C_6$)alkyl, —O—($C_1$-$C_6$)alkyl, and —$NR^3R^4$;

and the dotted line represents that the ring containing $X^{15}$ and $X^{16}$ contain one or two double bonds; and Het is selected from the group consisting of:

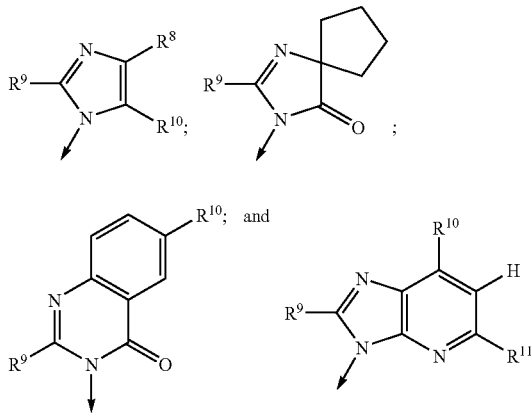

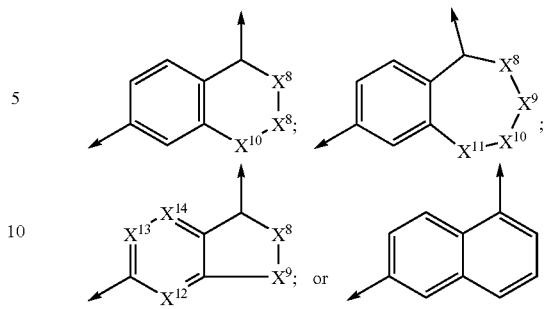

and $R^8$, $R^9$, $R^{10}$ and $R^{11}$ are independently selected from hydrogen, ($C_1$-$C_8$)alkyl, ($C_1$-$C_{10}$)alkenyl, ($C_3$-$C_8$)cycloalkyl, halo, ($C_1$-$C_8$)alkoxy, —S—($C_1$-$C_6$)alkyl, —SO—($C_1$-$C_6$)alkyl, —$CO_2H$, —$SO_2NR_3R_4$, —$NR_3R_4$, and phenyl, wherein said phenyl is optionally mono-, di-, or tri-substituted with halo, hydroxy, nitro, ($C_1$-$C_8$)alkyl, ($C_3$-$C_6$)cycloalkyl, ($C_1$-$C_7$)alkoxy, ($C_1$-$C_7$)alkylthio, and amino, wherein said amino is optionally mono- or di-substituted with ($C_1$-$C_7$)alkyl;

and wherein each occurrence of $R^3$ can be the same or different from any other occurrence of $R^3$, and each occurrence of $R^4$ can be the same or different from any other occurrence of $R^4$;

with the proviso that: (a) no more than two of $X^1$, $X^2$, $X^3$ and $X^4$ can be nitrogen; and (b) at least two of $X^7$, $X^8$, $X^9$, $X^{10}$ and $X^{11}$ are present;

and to pharmaceutically compatible salts thereof.

As used herein for compounds according to formula (VII):

the term "halo," unless otherwise indicated, includes chloro, fluoro, bromo and iodo;

the term "alkyl", unless otherwise indicated, includes saturated monovalent hydrocarbon radicals having straight, branched or cyclic moieties or combinations thereof, for example methyl, ethyl, n-propyl, isopropyl, n-butyl, isobutyl and t-butyl;

the term "alkenyl," unless otherwise indicated, means straight or branched unsaturated hydrocarbon radicals, for example, ethenyl, 1- or 2-propenyl, 2-methyl-1-propenyl and 1- or 2-butenyl;

the term "cycloalkyl," unless otherwise indicated, means a saturated carbocyclic radical, for example, cyclopropyl, cyclobutyl, cyclopentyl and cyclohexyl; and the term "alkoxy", unless otherwise indicated, includes O-alkyl groups wherein "alkyl" is defined as above.

In specific embodiments, compounds according to formula (VII) include those wherein W has the formula Examples of specific preferred compounds according to formula (VII) are:

2-butyl-5-chloro-1-{5-[2-(1H-tetrazol-5-yl)-phenyl]-indan-1-yl}-1H-imidazole-4-carboxylic acid ethyl ester;

2-butyl-5-chloro-1-{5-[2-(1H-tetrazol-5-yl)-phenyl]-indan-1-yl}-1H-imidazole-4-carboxylic acid;

2-butyl-3-{5-[2-(1H-tetrazol-5-yl)-phenyl]-indan-1-yl}-1,3-diazaspiro[4.4]non-1-en-4-one;

(2-butyl-5-chloro-1-{5-[2-(1H-tetrazol-5-yl)-phenyl]-indan-1-yl}-1H-imidazo 1-4-yl)methanol 2-ethyl-5,7-dimethyl-3-{5-[2-(1H-tetrazol-5-yl)-phenyl]-indan-1-yl}-3H-imidazole[4,5-b]pyridine;

(S)-2-ethyl-5,7-dimethyl-3-{5-[2-(1H-tetrazol-5-yl)-phenyl]-indan-1-yl}-3H-imidazo[4,5-b]pyridine;

(R)-2-ethyl-5,7-dimethyl-3-{5-[2-(1H-tetrazol-5-yl)-phenyl]-indan-1-yl}-3H-imidazol[4,5-b]pyridine;

2-ethyl-7-methyl-3-{5-[2-(1H-tetrazol-5-yl)-phenyl-indan-1-yl}-3H-imidazo[4,5-b]pyridine;

5,7-dimethyl-2-propyl-3-{5-[2-(1H-tetrazol-5-yl)-phenyl]-indan-1-yl}-3H-imidazo[4,5-b]pyridine;

2-cyclopropyl-5,7-dimethyl-3-{5-[2-(1H-tetrazol-5-yl)-phenyl]-indan-1-yl}-3H-imidazo[4,5-b]pyridine;

2-butyl-5,7-dimethyl-3-{5-[2-(1H-tetrazol-5-yl)-phenyl]-indan-1-yl}-3H-imidazo[4,5-b]pyridine;

2-butyl-3-{5-[2-(1H-tetrazol-5-yl)-phenyl]-indan-1-yl}-3H-imidazo[4,5-b]pyridine;

2-[1-(2-ethyl-5,7-dimethyl-imidazo[4,5-b]pyridin-3-yl)-indan-5-yl-benzoic acid;

2-[5-(2-ethyl-5,7-dimethyl-imidazo[4,5-b]pyridin-3-yl)-5,6,7,8-tetrahydro-4H-naphthalen-2-yl]-benzoic acid;

2-ethyl-5,7-dimethyl-3-{6-[2-(1H-tetrazol-5-yl)-phenyl]-1,2,3,4-tetrahydro-4H-naphthalen-1-yl}-3H-imidazo[4,5-b]pyridine;

2-ethyl-5,7-dimethyl-3-{2-[2-(1H-tetrazol-5-yl)-phenyl]-6,7,8,9-tetrahydro-5H-benzocyclohepten-5-yl}-3H-imidazo[4,5-b]pyridine;

2-ethyl-5,7-dimethyl-3-{7-[2-(1H-tetrazol-5-yl)-phenyl]-chroman-4-yl}-3H-imidazo[4,5-b]pyridine;

2-ethyl-5,7-dimethyl-3-{3-[2-(1H-tetrazol-5-yl)-phenyl]-bicyclo[4.2.0]octa-1,3,5-trien-7-yl}-3H-imidazo[4,5-b]pyridine;

2-ethyl-5,7-dimethyl-3-{7-[2-(1H-tetrazol-5-yl)-phenyl]-chroman-4-yl}-3H-imidazo[4,5-b]pyridine;

2-ethyl-5,7-dimethyl-3-{3-[2-(1H-tetrazol-5-yl)-phenyl]-6,7-dihydro-5H-[1]pyridin-7-yl}-3H-imidazo[4,5-b]pyridine;

2-[5-(2-butyl-imidazo[4,5-b]pyridin-3-yl)-naphthalen-2-yl]-benzoic acid;

2-butyl-3-{6-[2-(1H-tetrazol-5-yl)-phenyl]-naphthalen-1-yl}3H-imidazo[4,5-b]pyridine; and 2-ethyl-5,7-dimethyl-3-{6-[2-(1H-tetrazol-5-yl)-phenyl-naphthalen-1-yl}-3H-imidazo[4,5-b]pyridine.

Other compounds of according to formula (VII) include the following:

2-ethyl-5,7-dimethyl-3-{7-[2-(2H-tetrazol-5-yl)-phenyl]-thiochroman-4-yl}-3H-imidazo[4,5-b]pyridine;
3-{1,1-dioxo-7-[2-(2H-tetrazol-5-yl)-phenyl]-thiochroman-4-yl}-2-ethyl-5,7-dimethyl-3H-imidazo[4,5-b]pyridine;
2-ethyl-5,7-dimethyl-3-{2-[2-(2H-tetrazol-5-yl)-phenyl]-5,6-dihydro-4H-thieno[2,3-b]thiopyran-4-yl}-3H-imidazo[4,5-b]pyridine;
2-ethyl-5,7-dimethyl-3-{2-[2-(2H-tetrazol-5-yl)-phenyl]-4,5,6,7-tetrahydrobenzo[b]thiophen-4-yl}-3H-imidazo[4,5-b]pyridine; P0 2-ethyl-5,7-dimethyl-3-{2-[2-(2H-tetrazol-5-yl)-phenyl]-5,6-dihydro-4H-cyclopenta[b]thiophen-4-yl}-3H-imidazo[4,5-b]pyridine;
2-ethyl-5,7-dimethyl-3-{6-[2-(2H-tetrazol-5-yl)-phenyl]-3,4-dihydro-2H-thieno[2,3-b]pyran-4-yl}-3H-imidazo[4,5-b]pyridine;
2-ethyl-5,7-dimethyl-3-{2-[2-(2H-tetrazol-5-yl)-phenyl]-6,7-dihydro-5H-[1]pyridin-5-yl}-3H-imidazo[4,5-b]pyridine;
5-(2-ethyl-5,7-dimethyl-imidazo[4,5-b]pyridin-3-yl)-2-[2-(2H-tetrazol-5-yl)-phenyl]-5,6,7,8-tetrahydro-quinoline;
4-(2-ethyl-5,7-dimethyl-imidazo[4,5-b]pyridin-3-yl)-7-[2-(2H-tetrazol-5-yl)-phenyl]-3,4-dihydro-2H-thiopyrano[2,3-b]pyridine-1,1-dioxide;
2-ethyl-5,7-dimethyl-3-{2-[2-(2H-tetrazol-5-yl)-phenyl]-6,7-dihydro-5H-cyclopentapyrimidin-5-yl}-3H-imidazo[4,5-b]pyridine;
2-ethyl-5,7-dimethyl-3-{3-[2-(2H-tetrazol-5-yl)-phenyl]-6,7-dihydro-5H-[2]pyridin-7-yl}-3H-imidazo[4,5-b]pyridine;
2-ethyl-5,7-dimethyl-3-{5-[3-(2H-tetrazol-5-yl)-thiophen-2-yl]-indan-1-yl}-3H-imidazo[4,5-b]pyridine;
2-ethyl-5,7-dimethyl-3-{5-[2-(2H-tetrazol-5-yl)-thiophen-3-yl]-indan-1-yl}-3H-imidazo[4,5-b]pyridine;
2-ethyl-5,7-dimethyl-3-{5-[4-(2H-tetrazol-5-yl)-thiophen-3-yl]-indan-1-yl}-3H-imidazo[4,5-b]pyridine;
2-ethyl-5,7-dimethyl-3-{5-[3-(2H-tetrazol-5-yl)-pyridin-4-yl]-indan-1-yl}-3H-imidazo[4,5-b]pyridine;
2-ethyl-5,7-dimethyl-3-{5-[4-(2H-tetrazol-5-yl)-pyridin-3-yl]-indan-1-yl}-3H-imidazo[4,5-b]pyridine;
2-ethyl-5,7-dimethyl-3-{5-[3-(2H-tetrazol-5-yl)-pyridin-2-yl]-indan-1-yl}-3H-imidazo[4,5-b]pyridine;
(2-butyl-5-chloro-3-{5-[2-(2H-tetrazol-5-yl)-phenyl]-indan-1-yl}-3H-imidazole-4-yl)methanol;
2-butyl-5-chloro-3-{5-[2-(2H-tetrazol-5-yl)-phenyl]-indan-1-yl}-3H-imidazole-4-carboxylic acid;
2-butyl-5-(1,1,2,2,2-pentafluoro-ethyl)-3-{5-[2-(2H-tetrazol-5-yl)-phenyl]-indan-1-yl}-3H-imidazole-4-carboxylic acid;
2-butyl-5-ethyl-3-{5-[2-(2H-tetrazol-5-yl)-phenyl]-indan-1-yl}-3H-imidazole-4-carboxylic acid;
2-ethoxy-3-{5-[2-(2H-tetrazol-5-yl)-phenyl]-indan-1-yl}-3H-benzoimidazole-4-carboxylic acid;
2-ethylsulfanyl-3-{5-[2-(2H-tetrazol-5-yl)-phenyl]-indan-1-yl}-3H-benzoimidazole-4-carboxylic acid;
N-benzoyl-2-[1-(2-ethyl-5,7-dimethyl-imidazo[4,5-b]pyridin-3-yl)-indan-5-yl]-benzenesulfonamide; and
N-{2-[1-(2-ethyl-5,7-dimethyl-imidazo[4,5-b]pyridin-3-yl)-indan-5-yl]-phenyl}-benzenesulfonamide.

Other illustrative AT$_2$ receptor antagonist compounds are described for example by Rosentrö, Ulrika in a thesis entitled "Design and synthesis of AT$_2$ receptor antagonist selective angiotensin II analogues encompassing β and γ turn mimetics", 2004, Uppsala University, Sweden; and by Timmermans et al., 1993, *Pharmacol Reviews* 45(2): 205-251.

In further embodiments, the AT$_2$ receptor antagonist is selected from AT$_2$ receptor antagonist peptides, illustrative examples of which include hexa-, hepta- and octapeptides represented by the formula:

$$R_1\text{-}R_2\text{-}R_3\text{-}R_4\text{-}R_5\text{-}R_6\text{-}Pro\text{-}R_7 \text{(SEQ ID NO: 28)} \quad \text{(VIII)}$$

wherein:

$R_1$ is absent or is selected from hydrogen, succinyl, L-aspartyl, sarcosyl, L-seryl, succinamyl, L-propyl, glycyl, L-tyrosyl, N$_\alpha$-nicotinoyl-tyrosyl, or D- or L-asparagyl;

$R_2$ is selected from arginyl or N-benzoylcarbonyl arginyl;

$R_3$ is absent or valyl;

$R_4$ is absent or is selected from L-phenylalanyl or L-tyrosyl;

$R_5$ is selected from valyl, L-isoleucyl, L-alanyl or L-lysyl;

$R_6$ is selected from L-histidyl, L-isoleucyl, L-tyrosyl or p-aminophenylalanyl; and $R_7$ is selected from L-alanine, L-tyrosine, L- or D-leucine, glycine, L-isoleucine or β-alanine residue.

and pharmaceutically acceptable salts of these peptides.

Representative examples according to formula (VIII) include, but are not limited to:

| | |
|---|---|
| H-Asn-Arg-Val-Tyr-Val-His-Pro-Ala-OH; | [SEQ ID NO: 1] |
| H-Asn-Arg-Val-Tyr-Val-His-Pro-Leu-OH; | [SEQ ID NO: 2] |
| Succinyl-Arg-Val-Tyr-Val-His-Pro-Ala-OH; | [SEQ ID NO: 3] |
| H-Asp-Arg-Val-Tyr-Val-His-Pro-Ala-OH; | [SEQ ID NO: 4] |
| H-Arg-Val-Tyr-Val-His-Pro-Ala-OH; | [SEQ ID NO: 5] |
| H-Sar-Arg-Val-Tyr-His-Pro-Ala-OH; | [SEQ ID NO: 6] |
| H-Ser-Arg-Val-Tyr-His-Pro-Ala-OH; | [SEQ ID NO: 7] |
| Succinamyl-Arg-Val-Tyr-Val-His-Pro-Ala-OH; | [SEQ ID NO: 8] |
| H-Asn-Arg-Val-Tyr-Val-His-Pro-Gly-OH; | [SEQ ID NO: 9] |
| H-Asn-Arg-Val-Tyr-Val-His-Pro-Ile-OH; | [SEQ ID NO: 10] |
| H-Sar-Arg-Val-Tyr-Val-His-Pro-Gly-OH; | [SEQ ID NO: 11] |
| H-Pro-Arg-Val-Tyr-Val-His-Pro-Gly-OH; | [SEQ ID NO: 12] |
| H-Asn-Arg-Val-Tyr-Val-His-Pro-Gly-OH; | [SEQ ID NO: 13] |
| H-Sar-Arg-Val-Tyr-Val-His-Pro-β-Ala-OH; | [SEQ ID NO: 14] |

-continued

H-Asn-Arg-Val-Tyr-Val-His-Pro-β-Ala-OH; [SEQ ID NO: 15]

H-Gly-Arg-Val-Tyr-Val-His-Pro-Ala-OH; [SEQ ID NO: 16]

H-Sar-Arg-Val-Tyr-Ile-His-Pro-Leu-OH; [SEQ ID NO: 17]

H-Asn-Arg-Val-Tyr-Val-His-Pro-Leu-OH; [SEQ ID NO: 18]

H-Sar-Arg-Val-Tyr-Ile-His-Pro-Ala-OH also known as saralasin;, [SEQ ID NO: 19]

H-Asn-Arg-Val-Tyr-Ile-His-Pro-Ala-OH; [SEQ ID NO: 20]

H-Asn-Arg-Val-Tyr-Ala-His-Pro-Ala-OH; [SEQ ID NO: 21]

H-Asp-Arg-Val-Phe-Ile-His-Pro-Tyr-OH also known as Phe$^4$-Tyr$^8$-Ang II;, [SEQ ID NO: 22]

H-Asp-Arg-Val-Tyr-Ile-p-NH$_2$Phe-Pro-Phe-OH also known as [p-NH$_2$Phe]$^6$-Ang II;, and [SEQ ID NO: 23]

nicotinic acid-Tyr-(N-benzoylcarbonyl-Arg)-Lys-His-Pro-Ile-OH, also known as CGP-42112A; [SEQ ID NO: 24]

In other embodiments, the AT$_2$ receptor antagonist is selected from antigen-binding molecules that are immuno-interactive with an AT$_2$ receptor polypeptide. Illustrative antigen-binding molecules include whole polyclonal antibodies. Such antibodies may be prepared, for example, by injecting an AT$_2$ receptor polypeptide or fragment thereof into a production species, which may include mice or rabbits, to obtain polyclonal antisera. Methods of producing polyclonal antibodies are well known to those skilled in the art. Exemplary protocols which may be used are described for example in Coligan et al., "Current Protocols In Immunology", (John Wiley & Sons, Inc, 1991), and Ausubel et al., (Current Protocols in Molecular Biology", John Wiley & Sons Inc, 1994-1998), in particular Section III of Chapter 11.

In lieu of the polyclonal antisera obtained in the production species, monoclonal antibodies may be produced using the standard method as described, for example, by Köhler and Milstein (1975, Nature 256, 495-497), or by more recent modifications thereof as described, for example, in Coligan et al., (1991, supra) by immortalizing spleen or other antibody-producing cells derived from a production species which has been inoculated with an AT$_2$ receptor polypeptide or fragment thereof.

The invention also contemplates as antigen-binding molecules Fv, Fab, Fab' and F(ab')$_2$ immunoglobulin fragments. Alternatively, the antigen-binding molecule may be in the form of a synthetic stabilized Fv fragment, a single variable region domain (also known as a dAbs), a "minibody" and the like as known in the art.

Also contemplated as antigen binding molecules are humanized antibodies. Humanized antibodies are produced by transferring complementary determining regions from heavy and light variable chains of a non human (e.g., rodent, preferably mouse) immunoglobulin into a human variable domain. Typical residues of human antibodies are then substituted in the framework regions of the non human counterparts. The use of antibody components derived from humanized antibodies obviates potential problems associated with the immunogenicity of non human constant regions. General techniques for cloning non human, particularly murine, immunoglobulin variable domains are described, for example, by Orlandi et al. (1989, Proc. Natl. Acad. Sci. USA 86: 3833). Techniques for producing humanized monoclonal antibodies are described, for example, by Jones et al. (1986, Nature 321:522), Carter et al. (1992, Proc. Natl. Acad. Sci. USA 89: 4285), Sandhu (1992, Crit. Rev. Biotech. 12: 437), Singer et al. (1993, J. Immun. 150: 2844), Sudhir (ed., Antibody Engineering Protocols, Humana Press, Inc. 1995), Kelley ("Engineering Therapeutic Antibodies," in Protein Engineering: Principles and Practice Cleland et al. (eds.), pages 399-434 (John Wiley & Sons, Inc. 1996), and by Queen et al., U.S. Pat. No. 5,693,762 (1997).

Illustrative antigen-binding molecules that are immuno-interactive with AT$_2$ receptor polypeptides and methods for their preparation are described by Nora et al. (1998, Am J Physiol. 275(4 Pt 2):H1395-403), Yiu et al. (1997, Regul Pept. 70(1):15-21), Reagan et al. (1993, Proc Natl Acad Sci USA. 90(17):7956-7960), Rakugi et al. (1997, Hypertens Res. 20(1):51-55) and Wang et al. (1998 Hypertension. 32(1): 78-83), and some are available commercially, such as but not limited to H-143 (Santa Cruz Biotechnology, Santa Cruz, Calif.), which is directed against amino acid residues 221-363 from the carboxy terminus of human AT$_2$, rAT2 (Ab #1), which is directed against an 18-residue C-terminal fragment of rat AT$_2$), rAT2 (Ab #2) which is directed against an 18-residue C-terminal fragment of rat AT$_2$) and rAT2 (Ab #3), which is directed against a 10-residue N-terminal fragment of rat AT$_2$ (Alpha Diagnostic International, Inc.—5415 Lost Lane, SA).

In still other embodiments, the AT$_2$ receptor antagonist is selected from nucleic acid molecules that inhibit or otherwise reduce the level or functional activity of an expression product of an AT$_2$ gene, illustrative examples of which include antisense molecules, ribozymes and RNAi molecules. Thus, the present invention contemplates antisense RNA and DNA molecules as well as ribozymes and RNAi molecules that function to inhibit the translation, for example, of Agtr2 mRNA. Antisense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of an Agtr2 gene, are desirable. Exemplary antisense oligonucleotides can be derived from any nucleic acid molecule that encodes an AT$_2$ receptor, such as those described in U.S. Pat. No. 5,556,780, and in U.S. Pat. Appl. Pub. No. 20030083339. Therapeutic methods utilizing antisense oligonucleotides have been described in the art, for example, in U.S. Pat. Nos. 5,627,158 and 5,734,033. Generally, antisense molecules comprise from about 8 to about 30 bases (i.e., from about 8 to about 30 linked nucleosides) and typically comprise from about 12 to about 25 bases.

Ribozymes are enzymatic RNA molecules capable of catalyzing the specific cleavage of RNA. The mechanism of ribozyme action involves sequence specific hybridization of the ribozyme molecule to complementary target RNA, followed by an endonucleolytic cleavage. Within the scope of the invention are engineered hammerhead motif ribozyme molecules that specifically and efficiently catalyze endonucleolytic cleavage of Agtr2 RNA sequences. Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Both antisense RNA and DNA molecules and ribozymes may be prepared by any method known in the art for the synthesis of nucleic acid molecules. These include techniques for chemically synthesizing oligodeoxyribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to nucleic acid molecules may be introduced as a means of increasing intracellular stability and half-life. Possible modifications include but are not limited to the addition of flanking sequences of ribo- or deoxy-nucleotides to the 5' and/or 3' ends of the molecule or the use of artificial linkages rather than phosphodiesterase linkages within the oligodeoxyribonucleotide backbone. Illustrative modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or to 5'-2'. Various salts, mixed salts and free acid forms are also included.

Other agents that may be used to decrease the expression of an Agtr2 gene or the level and/or functional activity of an expression product of that gene include RNA molecules that mediate RNA interference (RNAi) of a Agtr2 gene or gene transcript. RNAi refers to interference with or destruction of the product of a target gene by introducing a single stranded, and typically a double stranded RNA (dsRNA), which is homologous to the transcript of the target gene. Thus, in one embodiment, dsRNA per se and especially dsRNA-producing constructs that encode an amino acid sequence corresponding to at least a portion of an $AT_2$ receptor polypeptide may be used to decrease its level and/or functional activity. RNAi-mediated inhibition of gene expression may be accomplished using any of the techniques reported in the art, for instance by transfecting a nucleic acid construct encoding a stem-loop or hairpin RNA structure into the genome of the target cell, or by expressing a transfected nucleic acid construct having homology for a target gene from between convergent promoters, or as a head to head or tail to tail duplication from behind a single promoter. Any similar construct may be used so long as it produces a single RNA having the ability to fold back on itself and produce a dsRNA, or so long as it produces two separate RNA transcripts which then anneal to form a dsRNA having homology to a target gene.

Absolute homology is not required for RNAi, with a lower threshold being described at about 85% homology for a dsRNA of about 200 base pairs (Plasterk and Ketting, 2000, Current Opinion in Genetics and Dev. 10: 562-567). Therefore, depending on the length of the dsRNA, the RNAi-encoding nucleic acids can vary in the level of homology they contain toward the target gene transcript, i.e., with dsRNAs of 100 to 200 base pairs having at least about 85% homology with the target gene, and longer dsRNAs, i.e., 300 to 100 base pairs, having at least about 75% homology to the target gene. RNA-encoding constructs that express a single RNA transcript designed to anneal to a separately expressed RNA, or single constructs expressing separate transcripts from convergent promoters, are preferably at least about 100 nucleotides in length. RNA-encoding constructs that express a single RNA designed to form a dsRNA via internal folding are preferably at least about 200 nucleotides in length.

The promoter used to express the dsRNA-forming construct may be any type of promoter if the resulting dsRNA is specific for a gene product in the cell lineage targeted for destruction. Alternatively, the promoter may be lineage specific in that it is only expressed in cells of a particular development lineage. This might be advantageous where some overlap in homology is observed with a gene that is expressed in a non-targeted cell lineage. The promoter may also be inducible by externally controlled factors, or by intracellular environmental factors.

In another embodiment, RNA molecules of about 21 to about 23 nucleotides, which direct cleavage of specific mRNA to which they correspond, as for example described by Tuschl et al. in U.S. Pat. Appl. Pub. No. 20020086356, can be utilized for mediating RNAi. Such 21-23 nt RNA molecules can comprise a 3' hydroxyl group, can be single-stranded or double stranded (as two 21-23 nt RNAs) wherein the dsRNA molecules can be blunt ended or comprise overhanging ends (e.g., 5', 3').

4. Identification of $AT_2$ Receptor Antagonists

The invention also features methods of screening for agents that antagonize an $AT_2$ receptor, including reducing the expression of an $AT_2$ gene (also known as an Agtr2 gene) or the level and/or functional activity of an expression product of that gene. Thus, a candidate agent identified according to these methods has an ability to reduce the biological activity or property of an $AT_2$ receptor polypeptide.

Candidate agents falling within the scope of the present invention include antagonistic antigen-binding molecules, and inhibitor peptide fragments, antisense molecules, ribozymes, RNAi molecules and co-suppression molecules. Other candidate agents include small organic compounds having a molecular weight of more than 50 and less than about 2,500 Dalton and will typically comprise functional groups necessary for structural interaction with proteins, particularly hydrogen bonding, and typically include at least an amine, carbonyl, hydroxyl or carboxyl group, suitably at least two of the functional chemical groups. Candidate agents often comprise cyclical carbon or heterocyclic structures or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogues or combinations thereof.

Small (non-peptide) molecule $AT_2$ receptor antagonists are generally advantageous because such molecules are more readily absorbed after oral administration, have fewer potential antigenic determinants, or are more likely to cross the cell membrane than larger, protein-based pharmaceuticals. Small organic molecules may also have the ability to gain entry into an appropriate cell and affect the expression of a gene (e.g., by interacting with the regulatory region or transcription factors involved in gene expression); or affect the activity of a gene by inhibiting or enhancing the binding of accessory molecules.

Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc to produce structural analogues.

Screening may also be directed to known pharmacologically active compounds and chemical analogues thereof.

In some embodiments, the methods comprise: (1) contacting a preparation with a test agent, wherein the preparation contains (i) a polypeptide comprising an amino acid sequence corresponding to at least a biologically active fragment of an $AT_2$ receptor, or to a variant or derivative thereof; or (ii) a polynucleotide comprising at least a portion of a genetic sequence that regulates an $AT_2$ gene, which is operably linked to a reporter gene; and (2) detecting a decrease in the level and/or functional activity of the polypeptide, or an expression product of the reporter gene, relative to a normal or reference level and/or functional activity in the absence of the test agent, which indicates that the agent antagonizes the $AT_2$ receptor.

In illustrative examples of this type, the methods comprise the steps of establishing a control system comprising an $AT_2$ receptor polypeptide and a ligand which is capable of binding to the polypeptide; establishing a test system comprising an $AT_2$ receptor polypeptide, the ligand, and a candidate compound; and determining whether the candidate compound inhibits or otherwise reduces the functional activity of the polypeptide by comparison of the test and control systems. Representative ligands can comprise a compound according to any one of formulae I-VIII, and in these embodiments, the functional activity screened can include binding affinity. In certain embodiments, the methods comprise (a) incubating an $AT_2$ receptor polypeptide with a ligand (e.g., angiotensin II) in the presence of a test inhibitor compound; (b) determining an amount of ligand that is bound to the $AT_2$ receptor polypeptide, wherein decreased binding of ligand to the $AT_2$ receptor polypeptide in the presence of the test inhibitor compound relative to binding in the absence of the test inhibitor compound is indicative of inhibition; and (c) identifying the test compound as an $AT_2$ receptor antagonist if decreased ligand binding is observed. In other embodiments, the methods comprise: (a) incubating a cell membrane, which comprises an $AT_2$ receptor polypeptide, with a first ligand (e.g., angiotensin II) in the presence of a test inhibitor compound; (b) optionally blocking any $AT_1$ receptors present on or in the membrane with a second ligand that binds specifically to the $AT_1$ receptor (e.g., losartan or candesartan) if the first ligand also binds to the $AT_1$ receptor; (c) determining an amount of first ligand that is bound to the membrane, wherein decreased binding of ligand to the membrane in the presence of the test inhibitor compound relative to binding in the absence of the test inhibitor compound is indicative of inhibition; and (d) identifying the test compound as an $AT_2$ receptor antagonist if decreased first ligand binding is observed.

In other illustrative examples, a form of an $AT_2$ receptor polypeptide or a catalytic or immunogenic fragment or oligopeptide thereof, is used for screening libraries of compounds in any of a variety of drug screening techniques. The fragment employed in such a screening can be affixed to a solid support. The formation of binding complexes, between an $AT_2$ receptor polypeptide and the agent being tested, will be detected. In specific embodiments, an $AT_2$ receptor polypeptide comprises an amino acid sequence corresponding to any one of:

[SEQ ID NO: 25]
MKGNSTLATTSKNITSGLHFGLVNISGNNESTLNCSQKPSDKHLDAIPIL

YYIIFVIGFLVNIVVVTLFCCQKGPKKVSSIYIFNLAVADLLLLATLPLW

ATYYSYRYDWLFGPVMCKVFGSFLTLNMFASIFFITCMSVDRYQSVIYPF

LSQRRNPWQASYIVPLVWCMACLSSLPTFYFRDVRTIEYLGVNACIMAFP

PEKYAQWSAGIALMKNILGFIIPLIFIATCYFGIRKHLLKTNSYGKNRIT

RDQVLKMAAAVVLAFIICWLPFHVLTFLDALAWMGVINSCEVIAVIDLAL

PFAILLGFTNSCVNPFLYCFVGNRFQQKLRSVFRVPITWLQGKRESMSCR

KSSSLREMETFVS (human AGTR2);

[SEQ ID NO: 26]
MKDNFSFAATSRNITSSRPFDNLNATGTNESAFNCSHKPSDKHLEAIPVL

YYMIFVIGFAVNIVVVSLFCCQKGPKKVSSIYIFNLALADLLLLATLPLW

ATYYSYRYDWLFGPVMCKVFGSFLTLNMFASIFFITCMSVDRYQSVIYPF

LSQRRNPWQASYVVPLVWCMACLSSLPTFYFRDVRTIEYLGVNACIMAFP

PEKYAQWSAGIALMKNILGFIIPLIFIATCYFGIRKHLLKTNSYGKNRIT

RDQVLKMAAAVVLAFIICWLPFHVLTFLDALTWMGIINSCEVIAVIDLAL

PFAILLGFTNSCVNPFLYCFVGNRFQQKLRSVFRVPITWLQGKRETMSCR

KGSSLREMDTFVS (murine AGTR2);
and

[SEQ ID NO: 27]
MKDNFSFAATSRNITSSLPFDNLNATGTNESAFNCSHKPADKHLEAIPVL

YYMIFVIGFAVNIVVVSLFCCQKGPKKVSSIYIFNLAVADLLLLATLPLW

ATYYSYRYDWLFGPVMCKVFGSFLTLNMFASIFFITCMSVDRYQSVIYPF

LSQRRNPWQASYVVPLVWCMACLSSLPTFYFRDVRTIEYLGVNACIMAFP

PEKYAQWSAGIALMKNILGFIIPLIFIATCYFGIRKHLLKTNSYGKNRIT

RDQVLKMAAAVVLAFIICWLPFHVLTFLDALTWMGIINSCEVIAVIDLAL

PFAILLGFTNSCVNPFLYCFVGNRFQQKLRSVFRVPITWLQGKRETMSCR

KSSSLREMDTFVS (rat AGTR2).

In still other illustrative examples, a plurality of different small test compounds are synthesized on a solid substrate, such as plastic pins or some other surface. The test compounds are reacted with an $AT_2$ receptor polypeptide, or fragments thereof. Bound polypeptide is then detected by methods well known to those of skill in the art. The polypeptide can also be placed directly onto plates for use in the aforementioned drug screening techniques.

In other illustrative examples, the methods comprise: contacting an $AT_2$ receptor polypeptide with individual members of a library of test samples; detecting an interaction between a test sample and an $AT_2$ receptor polypeptide; identifying a test sample that interacts with an $AT_2$ receptor polypeptide; and isolating a test sample that interacts with an $AT_2$ receptor polypeptide.

In each of the foregoing embodiments, an interaction can be detected spectrophotometrically, radiologically or immunologically. An interaction between $AT_2$ receptor polypeptide and a test sample can also be quantified using methods known to those of skill in the art.

In still other embodiments, the methods comprise incubating a cell (e.g., an endothelial cell such as a coronary endothelial cell (CEC), a PC12W cell, a SK-UT-1 cell, a 3T3 fibroblast cell or a NG108-15 cell), which naturally or recombinantly expresses an $AT_2$ receptor on its surface, in the presence and absence of a candidate agent under conditions in which the $AT_2$ receptor is able to bind an $AT_2$ receptor ligand, and the level of $AT_2$ receptor activation is measured by a suitable assay. For example, an $AT_2$ receptor antagonist can be identified by measuring the ability of a candidate agent to decrease $AT_2$ receptor activation in the cell from a baseline value in the presence of receptor ligand. In illustrative examples, PC12W cells are exposed to, or cultured in the presence of angiotensin II and in the presence and absence of, the candidate agent under conditions in which the $AT_2$ receptor is active on the cells, and differentiation of the cells is measured. An agent tests positive for $AT_2$ receptor antagonism if it inhibits differentiation of the cells. In other illustrative examples, PC12W cells are exposed to, or cultured in the presence of angiotensin II and in the presence and absence of, the candidate agent under conditions in which the $AT_2$ receptor is active on the cells, and the level of nitric oxide or the level or functional activity of nitric oxide synthase in the cells is measured. An agent tests positive for $AT_2$ receptor antagonism if it inhibits nitric oxide or the level or functional activity of nitric oxide synthase. In still other illustrative examples, coronary endothelial cells are exposed to, or cultured in the presence of angiotensin II and in the presence and absence of the candidate agent under conditions in which the $AT_2$ receptor is active on the cells, and expression of Zfhep, which is a protein associated with cell differentiation, in the cells is measured. An agent tests positive for $AT_2$ receptor antagonism if it inhibits Zfhep expression in the cells. In specific embodiments, any $AT_1$ receptors on the surface of the cells is blocked using an $AT_1$ receptor ligand such as losartan and candesartan.

5. Compositions

Another aspect of the present invention provides compositions for treating, preventing and/or relieving the symptoms of inflammatory pain, comprising an effective amount of an $AT_2$ receptor antagonist and a pharmaceutically acceptable carrier and/or diluent.

Any known $AT_2$ receptor antagonist can be used in the methods of the present invention, provided that the $AT_2$ receptor antagonist are pharmaceutically active. A "pharmaceutically active" $AT_2$ receptor antagonist is in a form which results in the treatment and/or prevention of inflammatory pain, including the prevention of incurring a symptom, holding in check such symptoms or treating existing symptoms associated with inflammatory pain, when administered to an individual.

The effect of compositions of the present invention may be examined by using one or more of the published models of pain/nociception, especially of inflammatory pain, known in the art. This may be demonstrated, for example using a model which assesses the onset and development of inflammatory pain. For example, there are several models that rely on injecting a pro-inflammatory tissue irritant into the rat hindpaw to induce hindpaw inflammation and testing whether the administration of a test drug has anti-hyperalgesic (pain-relieving) efficacy. Illustrative methods of this type include the Randall Selitto method (1957, *Arch Int Pharmacodyn Ther* 111: 409-419), which involves injection of a small volume (0.1 mL) of Brewer's yeast into the rat hindpaw to induce hindpaw inflammation with the test drugs being administered by the subcutaneous route at the same time as the yeast is injected into the hindpaw. Noxious pressure is then applied to the inflamed hindpaw of the rat and the ability of the test compounds to either prevent the development of inflammation and/or to alleviate inflammatory pain is assessed. The pressure at which an escape response is observed, is measured, for example, at 1, 2 and 4 h after administration of the test drug. Dose-response curves are constructed based on the responses measured at 1 h post-dosing. The duration of the swelling hypersensitivity is between 24 and 48 h.

The Randall Selitto method has been modified by several groups in which the test drug is administered (e.g., 2 h) after injection of yeast into the rat's hindpaw (Otterness and Bliven, 1985, Laboratory models for testing non-steroidal anti-inflammatory drugs, in: Non-steroidal anti-inflammatory drugs, Lombardino, J. G. (Ed.), pp. 111-252. Wiley-Interscience, New York). The rationale for this change is that it is a more difficult challenge to alleviate inflammation that is already established, compared with prevention of inflammation development.

Additional modifications to the Randall Selitto method include changing the tissue irritant that is injected into the rat's hindpaw such that different irritants produce markedly different apparent responsiveness of the test drugs. Specifically, three classes of pro-inflammatory tissue irritants have been defined (Otterness and Bliven, 1985, supra), as follows:

(i) agents such as carrageenan and kaolin which produce hindpaw inflammation in the rat that is highly sensitive to anti-inflammatory drugs but insensitive to anti-serotonin drugs.

(ii) agents such as trypsin and elastase that are relatively insensitive to anti-inflammatory and anti-serotonin drugs.

(iii) agents such as dextran, hyaluronidase, acid phosphatase and serotonin that are highly sensitive to anti-serotonin agents and insensitive to anti-inflammatory agents.

Oedema produced by an injection of yeast into the rat hindpaw is generally regarded as being a hybrid of types (ii) and (iii) above (Otterness and Bliven, 1985). Although NSAIDs have been shown to effectively alleviate yeast-induced inflammatory pain in the rat hindpaw, NSAIDs have little effect on yeast-induced swelling. However, anti-serotonin agents effectively reduce yeast-induced swelling and inflammatory pain in the rat hindpaw (Otterness and Bliven, 1985).

Another method based in part on the modified Randall Selitto methods noted above uses Freund's complete adjuvant (FCA) as the inflammatory tissue irritant as described for instance in Example 1.

The active compounds of the present invention may be provided as salts with pharmaceutically compatible counterions. Pharmaceutically compatible salts refer to those salts which are, within the scope of sound medical judgment, suitable for use in contact with the tissues of humans and lower animals without undue toxicity, irritation, allergic response and the like, and are commensurate with a reasonable benefit/ risk ratio. Pharmaceutically compatible salts are well known in the art. For example, S. M. Berge, et al. describe pharmaceutically compatible salts in detail in *J. Pharmaceutical Sciences*, 66: 1-19 (1977). The salts can be prepared in situ during the final isolation and purification of the active compounds of the invention, or separately by reacting the free base function with a suitable organic acid. Examples of pharmaceutically compatible, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically compatible salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically compatible salts include, when appropriate, non-toxic ammonium, quaternary ammonium, and amine cations formed using counterions such as halide, hydroxide, carboxylate, sulfate, phosphate, nitrate, lower alkyl sulfonate and aryl sulfonate.

Pharmaceutical compositions suitable for use in the present invention include compositions wherein the pharmaceutically active compounds are contained in an effective amount to achieve their intended purpose. The dose of active compounds administered to a patient should be sufficient to achieve a beneficial response in the patient over time such as a reduction in at least one symptom associated with inflammatory pain. The quantity of the pharmaceutically active compounds(s) to be administered may depend on the subject to be treated inclusive of the age, sex, weight and general health condition thereof. In this regard, precise amounts of the active compound(s) for administration will depend on the judgement of the practitioner. In determining the effective amount of the active compound(s) to be administered in the treatment or prophylaxis of inflammatory pain, the physician may evaluate the level or amount of swelling, redness, hyperalgesia (e.g., mechanical and thermal hyperalgesia), and allodynia in, or experienced by, the subject. In any event, those of skill in the art may readily determine suitable dosages of the $AT_2$ receptor antagonists of the invention.

An effective amount of an $AT_2$ receptor antagonist is one that is effective for treating or preventing the symptoms associated with inflammatory pain, including the prevention of incurring a symptom, holding in check such symptoms, and/or treating existing symptoms associated with inflammatory pain. Modes of administration, amounts of $AT_2$ receptor antagonist administered, and $AT_2$ receptor antagonist formulations, for use in the methods of the present invention, are discussed below. Whether the inflammatory pain has been treated is determined by measuring one or more diagnostic parameters indicative of the course of the disease, compared to a suitable control. In the case of an animal experiment, a "suitable control" is an animal not treated with the $AT_2$ receptor antagonist, or treated with the pharmaceutical composition without the $AT_2$ receptor antagonist. In the case of a human subject, a "suitable control" may be the individual before treatment, or may be a human (e.g., an age-matched or similar control) treated with a placebo. In accordance with the present invention, the treatment of pain includes and encompasses without limitation: (i) preventing pain experienced by a subject which may be predisposed to the condition but has not yet been diagnosed with the condition and, accordingly, the treatment constitutes prophylactic treatment for the pathologic condition; (ii) inhibiting pain initiation or a painful condition, i.e., arresting its development; (iii) relieving pain, i.e., causing regression of pain initiation or a painful condition; or (iv) relieving symptoms resulting from a disease or condition believed to cause pain, e.g., relieving the sensation of pain without addressing the underlying disease or condition.

The methods of the present invention are suitable for treating an individual who has been diagnosed with inflammatory pain, who is suspected of having inflammatory pain, who is known to be susceptible and who is considered likely to develop inflammatory pain, or who is considered likely to develop a recurrence of a previously treated inflammatory pain.

In some embodiments, and dependent on the intended mode of administration, the $AT_2$ receptor antagonist-containing compositions will generally contain about 0.000001% to 90%, about 0.0001% to 50%, or about 0.01% to about 25%, by weight of $AT_2$ receptor antagonist, the remainder being suitable pharmaceutical carriers or diluents etc. The dosage of the $AT_2$ receptor antagonist can depend on a variety of factors, such as mode of administration, the species of the affected subject, age and/or individual condition, and can be easily determined by a person of skill in the art using standard protocols.

Depending on the specific inflammatory pain being treated, the active compounds may be formulated and administered systemically, topically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, inhaled, intranasal, or intraocular injections. For injection, the therapeutic agents of the invention may be formulated in aqueous solutions, suitably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

Alternatively, the compositions of the invention can be formulated for local or topical administration. In this instance, the subject compositions may be formulated in any suitable manner, including, but not limited to, creams, gels, oils, ointments, solutions and suppositories. Such topical compositions may include a penetration enhancer such as benzalkonium chloride, digitonin, dihydrocytochalasin B, capric acid, increasing pH from 7.0 to 8.0. Penetration enhancers which are directed to enhancing penetration of the active compounds through the epidermis are preferred in this regard. Alternatively, the topical compositions may include liposomes in which the active compounds of the invention are encapsulated.

The compositions of this invention may be formulated for administration in the form of liquids, containing acceptable diluents (such as saline and sterile water), or may be in the form of lotions, creams or gels containing acceptable diluents or carriers to impart the desired texture, consistency, viscosity and appearance. Acceptable diluents and carriers are familiar to those skilled in the art and include, but are not restricted to, ethoxylated and nonethoxylated surfactants, fatty alcohols, fatty acids, hydrocarbon oils (such as palm oil, coconut oil, and mineral oil), cocoa butter waxes, silicon oils, pH balancers, cellulose derivatives, emulsifying agents such as non-ionic organic and inorganic bases, preserving agents, wax esters, steroid alcohols, triglyceride esters, phospholipids such as lecithin and cephalin, polyhydric alcohol esters, fatty alcohol esters, hydrophilic lanolin derivatives, and hydrophilic beeswax derivatives.

Alternatively, the active compounds of the present invention can be formulated readily using pharmaceutically acceptable carriers well known in the art into dosages suitable for oral administration, which is also preferred for the practice of the present invention. Such carriers enable the compounds of the invention to be formulated in dosage forms such as tablets, pills, capsules, liquids, gels, syrups, slurries, suspensions and the like, for oral ingestion by a patient to be treated. These carriers may be selected from sugars, starches, cellulose and its derivatives, malt, gelatine, talc, calcium sulfate, vegetable oils, synthetic oils, polyols, alginic acid, phosphate buffered solutions, emulsifiers, isotonic saline, and pyrogen-free water.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatine, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more therapeutic agents as described above with the carrier which constitutes one or more necessary ingredients. In general, the pharmaceutical compositions of the present invention may be manufactured in a manner that is itself known, eg. by means of conventional mixing, dissolving, granulating, dragee-making, levigating, emulsifying, encapsulating, entrapping or lyophilizing processes.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceuticals which can be used orally include push-fit capsules made of gelatine, as well as soft, sealed capsules made of gelatine and a plasticiser, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Dosage forms of the active compounds of the invention may also include injecting or implanting controlled releasing devices designed specifically for this purpose or other forms of implants modified to act additionally in this fashion. Controlled release of an active compound of the invention may be achieved by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be achieved by using other polymer matrices, liposomes and/or microspheres.

The active compounds of the invention may be administered over a period of hours, days, weeks, or months, depending on several factors, including the severity of the inflammatory pain being treated, whether a recurrence of the inflammatory pain is considered likely, etc. The administration may be constant, e.g., constant infusion over a period of hours, days, weeks, months, etc. Alternatively, the administration may be intermittent, e.g., active compounds may be administered once a day over a period of days, once an hour over a period of hours, or any other such schedule as deemed suitable.

The compositions of the present invention may also be administered to the respiratory tract as a nasal or pulmonary inhalation aerosol or solution for a nebuliser, or as a microtine powder for insufflation, alone or in combination with an inert carrier such as lactose, or with other pharmaceutically acceptable excipients. In such a case, the particles of the formulation may advantageously have diameters of less than 50 micrometers, suitably less than 10 micrometers.

The $AT_2$ receptor antagonists may be provided alone or in combination with other compounds such as those that are useful in the control of inflammatory conditions. Illustrative compounds of this type include but are not restricted to non-steroidal anti-inflammatory compounds such as celecoxib, diflunisal, fenoprofen, indomethacin, ketoprofen, meclofenamin acid, naproxen, acyclovir, phenylbutazone, piroxicam, salsalate, sulindac, tolectin, rofecoxib, valdecoxib, and combinations of any two or more thereof. In some embodiments, the anti-inflammatory compounds are selected from: (a) Leukotriene biosynthesis inhibitors, 5-lipoxygenase (5-LO) inhibitors, and 5-lipoxygenase activating protein (FLAP) antagonists; (b) Receptor antagonists for leukotrienes $LTB_4$, $LTC_4$, $LTD_4$, and $LTE_4$; (c) 5-Lipoxygenase (5-LO) inhibitors and 5-lipoxygenase activating protein (FLAP) antagonists; (d) Dual inhibitors of 5-lipoxygenase (5-LO) and antagonists of platelet activating factor (PAF); (e) Leukotriene antagonists (LIRAS) of $LTB_4$, $LTC_4$, $LTD_4$, and $LTE_4$; (1) Antihistaminic $H_1$ receptor antagonists; (g) Gastroprotective $H_2$ receptor antagonists; (h) $\alpha_1$- and $\alpha_2$-adrenoceptor agonist vasoconstrictor sympathomimetic agents administered orally or topically for decongestant use; (i) one or more $\alpha_1$- and $\alpha_2$-adrenoceptor agonists as recited in (h) above in combination with one or more inhibitors of 5-lipoxygenase (5-LO) as recited in (a) above; (j) Theophylline and aminophylline; (k) Sodium cromoglycate; (l) Muscarinic receptor (M1, M2, and M3) antagonists; (m) COX-1 inhibitors (NTHEs); and nitric oxide NTHEs; (n) COX-2 selective inhibitors; (o) COX-3 inhibitor; (p) insulin-like growth factor type I (IGF-1) mimetics; (q) Ciclesonide; (r) Corticosteroids; (s) Tryptase inhibitors; (t) Platelet activating factor (PAF) antagonists; (u) Monoclonal antibodies active against endogenous inflammatory entities; (v) IPL 576; (w) Anti-tumor necrosis factor (TNF-α) agents; (x) DMARDs; (y) Elastase inhibitors; (z) TCR peptides; (aa) Interleukin converting enzyme (ICE) inhibitors; (bb) IMPDH inhibitors; (cc) Adhesion molecule inhibitors including VLA-4 antagonists; (dd) Cathepsins; (ee) Mitogen activated protein kinase (MAPK) inhibitors; (ff) Mitogen activated protein kinase kinase (MAPKK) inhibitors; (gg) Glucose-6 phosphate dehydrogenase inhibitors; (hh) Kinin-$B_1$- and $B_2$-receptor antagonists; (ii) Gold in the form of an aurothio group in combination with hydrophilic groups; (jj) Immunosuppressive agents; (kk) Anti-gout agents; (ll) Xanthine oxidase inhibitors; (mm) Uricosuric agents; (nn) Antineoplastic agents that are antimitotic drugs; (oo) Growth hormone secretagogues; (pp) Inhibitors of matrix metalloproteinases (MMPs); (qq) Transforming growth factor (TGF.beta.); (rr) Platelet-derived growth factor (PDGF); (ss) Fibroblast growth factor; (tt) Granulocyte macrophage colony stimulating factor (GM-CSF); (uu) Capsaicin; and (vv) Tachykinin $NK_1$ and $NK_3$ receptor antagonists. Non-limiting examples of this type are wherein: (a) the Leukotriene biosynthesis inhibitors, 5-lipoxygenase (5-LO) inhibitors, and 5-lipoxygenase activating protein (FLAP) antagonists are selected from the group consisting of zileuton; ABT-761; fenleuton; tepoxalin; Abbott-79175; Abbott-85761; N-(5-substituted)-thiophene-2-alkylsulfonamides; 2,6-di-tert-butylphenol hydrazones; Zeneca ZD-2138; SB-210661; pyridinyl-substituted 2-cyanonaphthalene compound L-739,010; 2-cyanoquinoline compound L-746,530; indole and quinoline compounds MK-591, MK-886, and BAY x 1005; (b) the receptor antagonists for leukotrienes $LTB_4$, $LTC_4$, $LTD_4$, and $LTE_4$ antagonists are selected from the group consisting of phenothiazin-3-one compound L-651,392; amidino compound CGS-25019c; benzoxazolamine compound ontazolast; benzenecarboximidamide compound BIIL 284/260; compounds zafirlukast, ablukast, montelukast, pranlukast, verlukast (MK-679), RG-12525, Ro-245913, iralukast (CGP 45715A), and BAY x 7195; (f) the antihistaminic $H_1$ receptor antagonists antagonists are selected from the group consisting of cetirizine, loratadine, desloratadine, fexofenadine, astemizole, azelastine, and chlorpheniramine; (h) $α_1$- and $α_2$-adrenoceptor agonist vasoconstrictor sympathomimetic agents are selected from the group consisting of propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride; (n) the COX-2 selective inhibitor are selected from the group consisting of rofecoxib and celecoxib; (o) the COX-3 inhibitor is acetaminophen; (r) the Corticosteroids are selected from the group consisting of prednisone, methylprednisone, triamcinolone, beclomethasone, fluticasone, budesonide, hydrocortisone, dexamethasone, mometasone furoate, azmacort, betamethasone, beclovent, prelone, prednisolone, flunisolide, triamcinolone acetonide, beclomethasone dipropionate, fluticasone propionate, mometasone furoate, solumedrol and salmeterol; (w) the anti-tumor necrosis factor (TNF-.alpha.) agents selected from the group consisting of etanercept, infliximab, and D2E7; (x) the DMARDs is leflunomide; (y) the Elastase inhibitors are selected from the group consisting of UT-77 and ZD-0892; (jj) the Immunosuppressive agents selected from the group consisting of cyclosporine, azathioprine, tacrolimus, and methotrexate; (kk) the anti-gout agents is colchicine; (ll) the Xanthine oxidase inhibitor is allopurinol; (mm) the Uricosuric agents are selected from the group consisting of probenecid, sulfinpyrazone, and benzbromarone; (nn) the antineoplastic agents are selected from the group consisting of vinblastine, vincristine, cyclophosphamide, and hydroxyurea; (pp) the inhibitors of matrix metalloproteinases (MMPs) are selected from the group consisting of stromelysins, the collagenases, the gelatinases, aggrecanase, collagenase-1 (MMP-1), collagenase-2 (MMP-8), collagenase-3 (MMP-13), stromelysin-1 (MMP-3), stromelysin-2 (MMP-10), and stromelysin-3 (MMP11); and, (vv) the Tachykinin NK.sub.1 and NK.sub.3 receptor antagonists are selected from the group consisting of NKP-608C; SB-233412 (talnetant); and D-4418.

In order that the invention may be readily understood and put into practical effect, particular preferred embodiments will now be described by way of the following non-limiting examples.

EXAMPLES

Example 1

PD-123,319 Produces Dose-Dependent Relief of Mechanical Hyperalgesia in the Inflamed Hindpaw of the FCA-Rat Model of Inflammatory Pain Single bolus doses of PD-123,319 were administered by the i.p. route to rats with FCA-induced unilateral hindpaw inflammation, a rat model of inflammatory pain. Anti-hyperalgesic (pain-relieving) efficacy was assessed using the Paw Pressure Test, a test which involves the application of noxious pressure to the inflamed hindpaw.

The results shown in FIG. 1 clearly show that PD-123,319 produced dose-dependent relief of mechanical hyperalgesia in the ipsilateral (inflamed) hindpaw of the FCA-rat model of inflammatory pain.

MATERIALS AND METHODS

Reagents and Materials

Isoflurane (Forthane®) was purchased from Abbott Australasia Pty Ltd (Sydney, Australia). Normal saline ampoules were obtained from Delta West Pty Ltd (Perth, Australia) and Abbott Australasia (Sydney, Australia). Dimethyl sulfoxide (DMSO) was purchased from Sigma Aldrich (Australia). Medical grade $O_2$ and $CO_2$ were purchased from BOC Gases Australia Ltd (Brisbane, Australia). PD-123,319, as described in U.S. Pat. No. 4,812,462, was synthesized in the laboratory of Dr Craig Williams, Dept of Chemistry, The University of Queensland (Brisbane, Australia).

Animals

Adult male Sprague-Dawley rats were purchased from the Herston Medical Research Centre, The University of Queensland. Rats were housed in a temperature controlled environment ($21\pm2°$ C.) with a 12 h/12 h light/dark cycle. Food and water were available ad libitum. Rats were given an acclimatization period of at least 3 days prior to initiation of experimental procedures. Ethical approval for this study was obtained from the Animal Experimentation Ethics Committee of The University of Queensland.

FCA Rat Model of Inflammatory Pain

Hindpaw inflammation was induced by the i.pl. injection of 150 μL of the tissue irritant, Freund's complete adjuvant (FCA), into the left hindpaw of adult male rats whilst they were anaesthetized with 3% isoflurane:97% oxygen. Following i.pl. FCA injection, the hindpaw volume increased approximately 1.5-2 fold over a 2-3 day period and this persisted for the study duration. This type of persistent tissue injury is well-documented to produce neuroplastic changes in the peripheral and central nervous systems, resulting in the development of thermal hyperalgesia (exaggerated response to the application of a noxious thennal stimulus). The ability of single bolus doses of PD-123,319 (~7-70 mg/kg) or vehicle to alleviate mechanical hyperalgesia in the ipsilateral (inflamed) hindpaw was assessed using the Paw Pressure Test (PPT). The contralateral (non-inflamed) hindpaw of the same animal served as an internal control.

Paw Pressure Thresholds (PPT)

Rats were gently restrained with a towel and noxious pressure was applied to each of the ipsilateral (inflamed) and the contralateral (non-inflamed) hindpaws using a Ugo Basile Analgesiometer. When the rats felt pain, they were able to freely withdraw their hindpaw. The Analgesiometer had a maximum cut-off of 250 g pressure to avoid tissue damage to the hindpaws when the rats' responses to the noxious mechanical stimulus were depressed by the test article. Paw pressure testing (PPT) was performed prior to i.pl. FCA administration and after day 4 post-FCA. Additionally, following administration of single i.p. bolus doses of PD-123, 319 or vehicle, PPT's were quantified at the following times: pre-dose, 0.08, 0.25, 0.5, 0.75, 1, 1.5, 2, 3 h post-dosing.

Example 2

Inflammatory Pain Model

Induction of Mechanical Hyperalgesia

Figure 2:
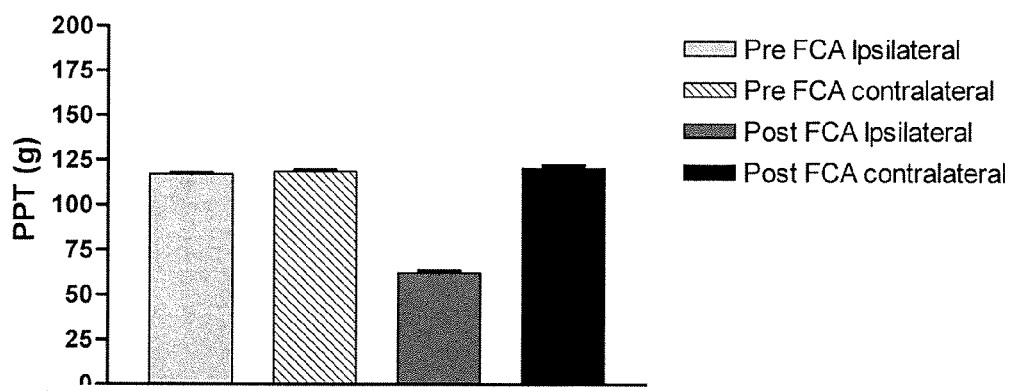
FIG. 2 is a graphical representation showing that administration of FCA induces mechanical hyperalgesia in the ipsilateral but not the contralateral hindpaw of rats (n=24). * Significantly (p<0.05) different from pre-FCA in the ipsilateral hindpaw.

Mechanical hyperalgesia developed in the ipsilateral (inflamed), but not the contralateral, hindpaw of rats following the i.pl. administration of FCA into one hindpaw. Specifically, the mean (±SEM) paw pressure thresholds (PPTs) for the ipsilateral hindpaw decreased significantly ($p<0.05$) from 117.1 (±0.8) g to 62.4 (±1.2) g by 5 days post-FCA administration. The mean (±SEM) PPT value for the contralateral hindpaw did not differ significantly ($p>0.05$) between that determined prior to FCA administration at 118.7 (±0.8) g and that determined 5 days later at 120.6 (±1.5) g in the same animals (FIG. 2).

Paw Volume

Figure 3:
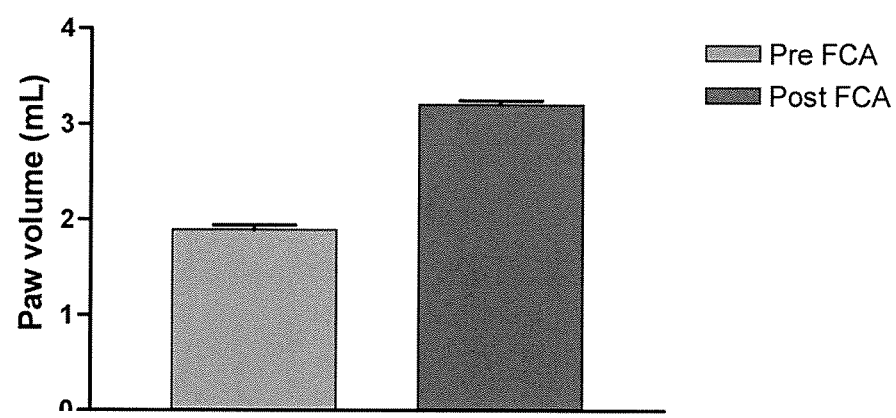
FIG. 3 is a graphical representation showing that administration of FCA increase paw volume in the ipsilateral hindpaw of rats, as expected. * Significantly (p<0.05) different from pre-FCA hindpaw volume.

Administration of FCA also increased the volume of the ipsilateral hindpaw, as expected. Specifically, the mean (±SEM) paw volume for the ipsilateral hindpaw increased significantly ($p<0.05$) from 1.9 (±0.04)mL to 3.2 (±0.04) mL by 5 days post-FCA administration (FIG. 3).

The Anti-Hyperalgesic Effect of Ema Compounds in Fca-Rats

Figure 4:
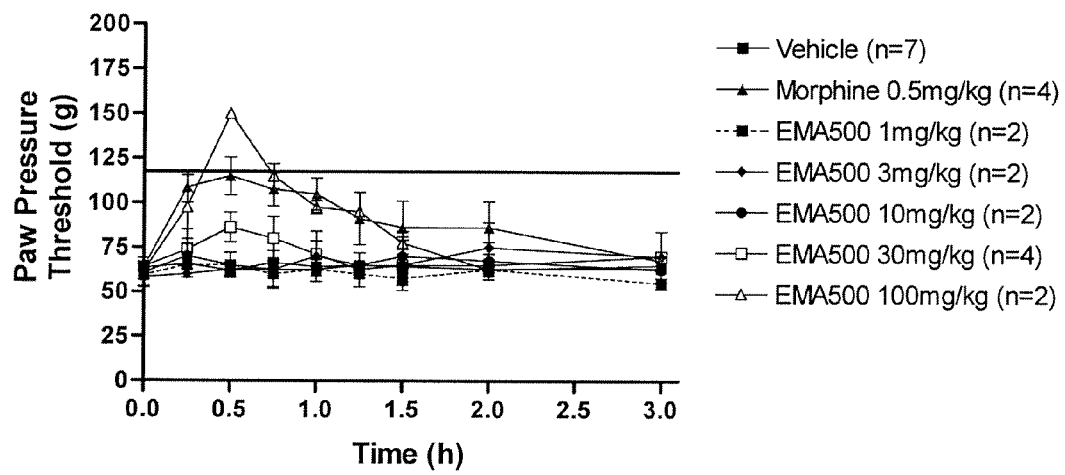
FIG. 4 is a graphical representation showing the anti-hyperalgesic (A) and antinociceptive (B) effects of EMA500 (1-100 mg/kg), morphine (0.5 mg/kg) and vehicle in FCA-rats.
Figure 4:
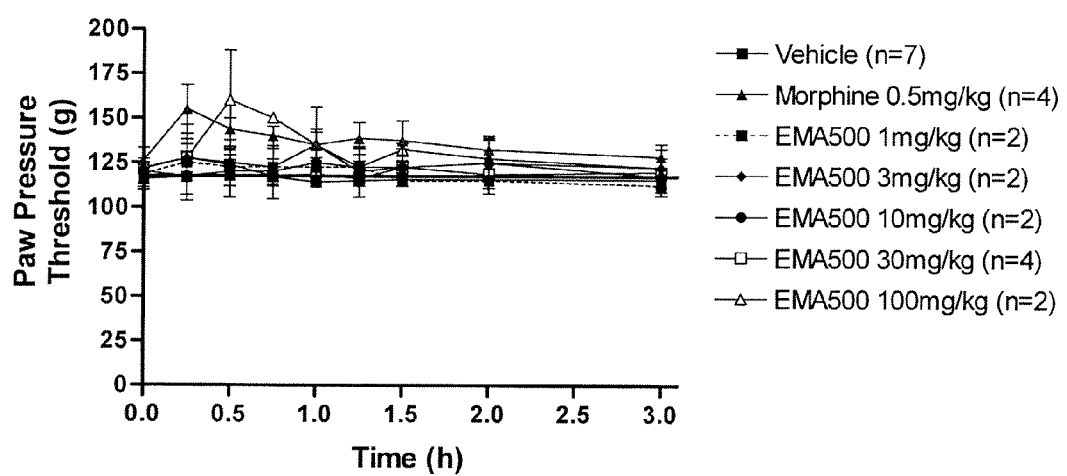

Administration of single i.p. bolus doses of EMA500 (sodium salt of L-161,638) (1 to 100 mg/kg) in FCA-rats, appeared to produce dose-dependent anti-hyperalgesia in the ipsilateral hindpaw (FIG. 4). For the doses tested, peak anti-hyperalgesia in the ipsilateral hindpaw occurred at approximately 0.5 h post-dosing and the corresponding duration of action was greater than 2 h at the highest dose tested (FIG. 4A). Specifically, at the highest dose tested (100 mg/kg), the mean(±SD) peak PPT increased from 61.7(±4.7) g pre-dose to 150(±0) g at 0.5 h post administration. Only at the highest dose tested (100 mg/kg) did EMA500 fully reverse mechanical hyperalgesia in FCA-rats. Administration of EMA500 in doses up to 100 mg/kg in FCA-rats produced insignificant antinociception in the contralateral hindpaw (FIG. 4B).

Figure 5:
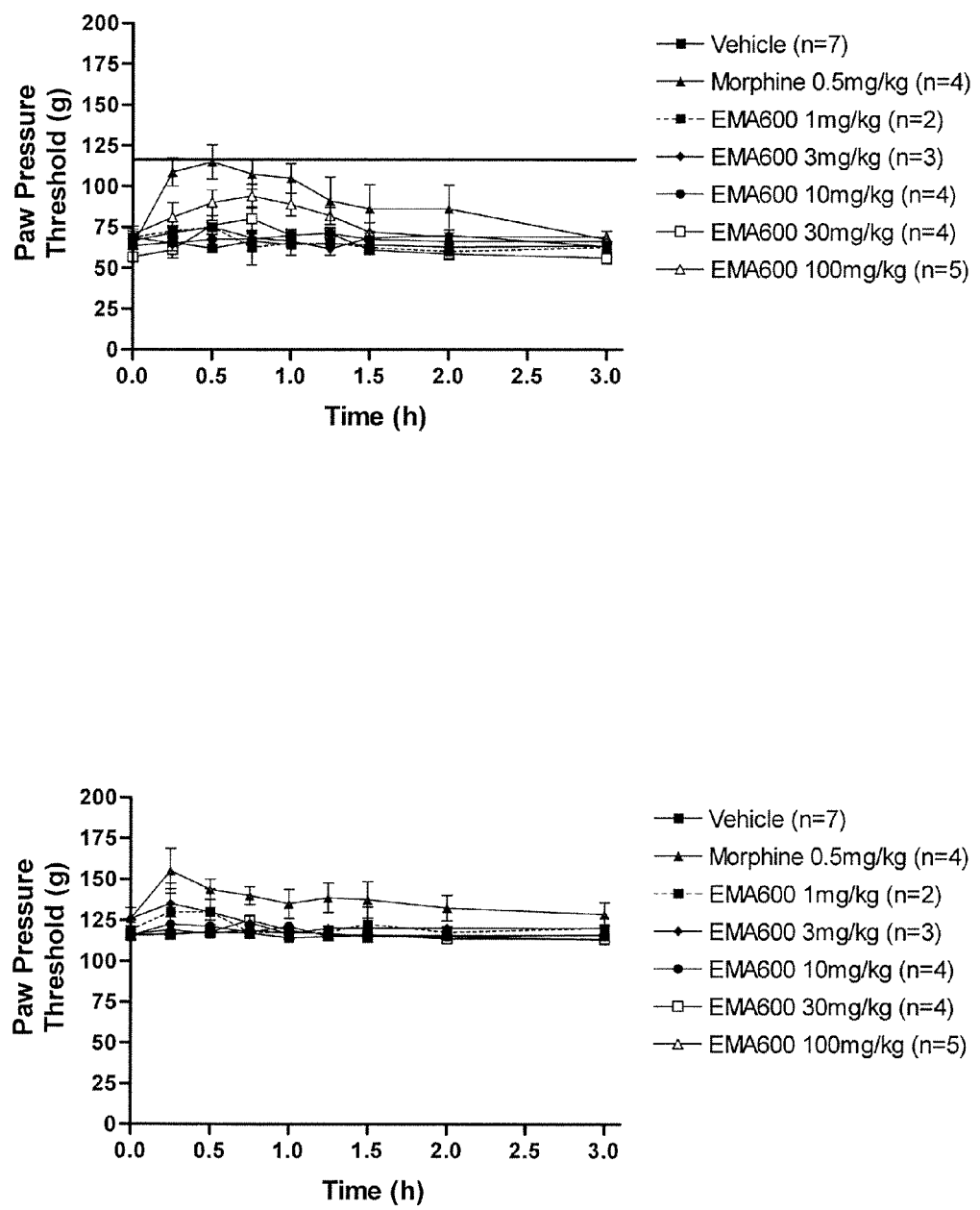
FIG. 5 is a graphical representation showing the anti-hyperalgesic (A) % maximum possible reversal (B) and antinociceptive (C) effects of EMA600 (1-100 mg/kg), morphine (0.5 mg/kg) and vehicle in FCA-rats

Following i.p. administration of single bolus doses of EMA600 (L-163,579) (1 to 100 mg/kg) in FCA-rats, there appeared to be dose-dependent anti-hyperalgesia produced in the ipsilateral hindpaw (FIG. 5). For the doses tested, peak anti-hyperalgesia in the ipsilateral hindpaw occurred at approximately 0.5-1 h post-dosing and the corresponding duration of action was approximately 1.5 h at the highest dose tested (FIG. 5A). Specifically, at the highest dose tested (100 mg/kg), the mean (±SEM) peak PPT increased from 70.7 (±3.3) g pre-dose to 94.0(±7.3) g at 0.75 h post administration. Administration of EMA600 in doses up to 100 mg/kg in FCA-rats produced insignificant antinociception in the contralateral hindpaw (FIG. 5B).

As expected, single bolus s.c. doses of morphine at 0.5 mg/kg produced an anti-hyperalgesic response which peaked at 0.5 h post-dosing, with a duration of action of approximately 2-3 h. Specifically, the mean (±SEM) PPT increased from 63.7 (±2.5) g pre-dosing to 115.0 (±10.6) g at the time of peak effect, demonstrating that morphine fully reversed FCA-induced mechanical hyperalgesia at 0.5 h post-dosing (FIGS. 3A and 4A). Additionally, morphine at 0.5 mg/kg produced a small antinociceptive effect in the contralateral hindpaw, but this did not reach statistical significance ($p>0.05$) (FIGS. 4B and 5B).

As expected, i.p. administration of vehicle did not produce anti-hyperalgesia or antinociception in the ipsilateral or contralateral hindpaws, respectively (FIGS. 4 and 5).

The Effect of EMA Compounds on Hindpaw Volume in FCA-Rats

Figure 6:
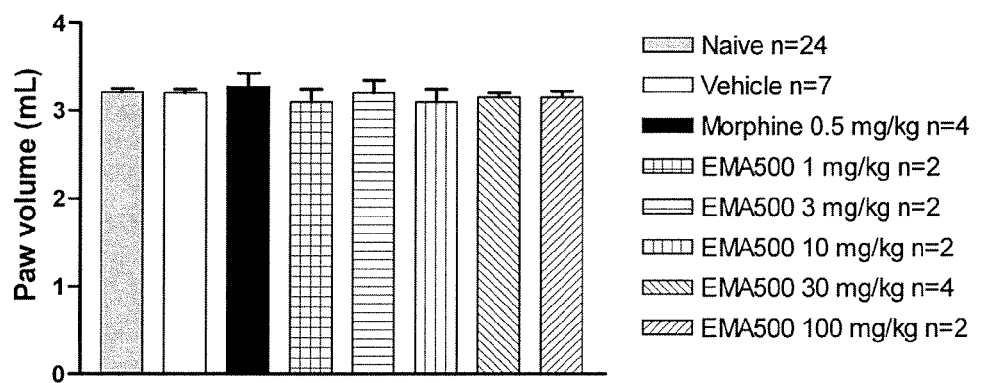
FIG. 6 is a graphical representation showing the effect of EMA500, EMA600, vehicle and morphine on the ipsilateral hindpaw volume at 3 h post dosing, in FCA-rats.
Figure 6:
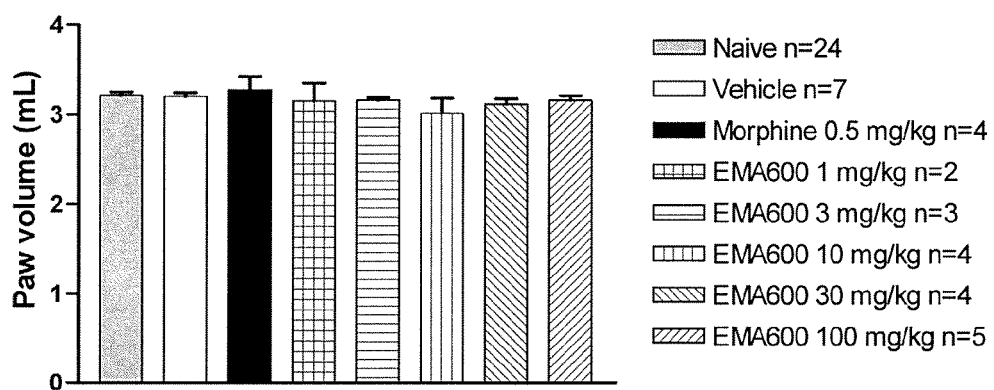

Single bolus doses of EMA500, EMA600, morphine or vehicle did not alter ipsilateral hindpaw volumes at 3 h post-dosing (FIG. 6).

DISCUSSION

Following i.p. administration of single bolus doses of EMA500 at 10 to 100 mg/kg, there was a dose-dependent relief of mechanical hyperalgesia (reversal) in the ipsilateral hindpaw which peaked at ~0.5 h post-dosing with a duration of action of 2 h. Following i.p. administration of single bolus doses of EMA600 at 100 mg/kg in FCA-rats, there was significant relief of mechanical hyperalgesia (~50% reversal) at the time of peak effect post-dosing. Administration of EMA500 (1-100 mg/kg) and EMA600 (1-100 mg/kg) in FCA-rats produced insignificant antinociception in the contralateral hindpaw.

Consistent with expectations, i.p. administration of vehicle did not result in significant relief of mechanical hyperalgesia in the ipsilateral hindpaw of FCA-rats, confirming that neither the surgical procedures nor the vehicle in which the test articles were dissolved, significantly alleviated mechanical hyperalgesia in the ipsilateral hindpaw of FCA-rats.

Paw volumes at 3 h post-dosing were unaffected by either EMA500, EMA600 or morphine at the doses tested.

Single i.p. bolus doses of EMA500 (1-100 mg/kg), EMA600 (1-30 mg/kg), morphine (0.5 mg/kg) and vehicle did not produce adverse behavioural effects in FCA-rats. However, single i.p. bolus doses of EMA600 at 100 mg/kg produced abnormal gait and abdominal retraction for 5-15 min post-dosing, suggestive of irritation in the peritoneal cavity at this dose.

METHODS

Experimental Animals

Ethical approval for this study was obtained from the Animal Experimentation Ethics Committee of The University of Queensland. Adult male Sprague-Dawley (SD) rats (270±3 g at the time of FCA injection), were used in this study. Rats were housed in a temperature controlled room (21±2.0° C.) with a 12 h/12 h light/dark cycle. Food and water were available ad libitum.

Drugs and Materials

Medical grade $O_2$ and $CO_2$ were purchased from BOC Gases Australia Ltd (Brisbane, Australia). Isoflurane (Iso-flo™) was purchased from Abbott Australasia (Sydney, Australia) Dimethyl sulfoxide (DMSO; lot #055K01033) and Freund's complete adjuvant (FCA) was purchased from Sigma-Aldrich (Sydney, Australia). Minivials (Eppendorf™) were purchased from Disposable Products (Brisbane, Australia). Morphine hydrochloride was from David Bull Laboratories (Melbourne, Australia).

Compounds for Administration

Test Articles

EMA500 (Lot# CHM502) and EMA600 (Lot# ALC 49-50-SPM151) were supplied by GlycoSyn, a business unit of Industrial Research Limited (New Zealand). EMA500, which is the sodium salt of L-161,638 (L-161,638 is described by Glinka et al. 1994, Bioorg. Med. Chem. Lett. 4:1479 and in U.S. Pat. No. 5,204,354) was synthesised as described in WO2006/066361. EMA600 (L-163,579) was synthesized as described by Glinka et al. (1994, Bioorg. Med. Chem. Lett. 4:2337) and in U.S. Pat. No. 5,441,959. EMA500 and EMA600 were supplied in powder form and were stored at room temperature. Stock solutions for EMA500 and EMA600 were made freshly each morning of every dosing day.

Positive Control

Single bolus s.c. doses of morphine at 0.5 mg/kg were utilised as the positive control for this study in FCA-rats.

Vehicle

The vehicle used to dissolve the Test Articles in this study was a 90%:10% mixture of DMSO:water, whereas sterile water for injection was the vehicle used for the positive control (morphine).

Experimental Protocol

FCA-Rat Model of Inflammatory Pain

Hindpaw inflammation was induced by the intraplantar (i.pl.) injection of 150 μL of the tissue irritant, Freund's complete adjuvant (FCA), into the left hindpaw of adult male rats, whilst they were anaesthetized with 3% isoflurane:97% oxygen ($O_2$). Following FCA injection, the hindpaw volume increased by 1.5-2 fold over a 2-3 day period and this persisted for the study duration. This type of persistent tissue injury is well-documented to produce neuroplastic changes in the peripheral and central nervous systems, resulting in the development of hyperalgesia (exaggerated response to the application of a noxious stimulus such as pressure in the ipsilateral (inflamed) hindpaw). The ability of single bolus doses of EMA500 and EMA600 to alleviate mechanical hyperalgesia (noxious pressure) was assessed using the Paw Pressure Test (see below for details). The contralateral (non-inflamed) hindpaw of the same animal served as an internal control.

Pharmacodynamic Assessment

Paw Pressure Thresholds (PPT)

Rats were gently restrained with a towel and noxious pressure was applied to each of the ipsilateral (inflamed) and the contralateral (non-inflamed) hindpaws using a Ugo Basile Analgesiometer. When the rats felt pain, they were able to freely withdraw their hindpaw. The Analgesiometer had a maximum cut-off of 250 g of pressure to avoid tissue damage to the hindpaws when the rats' responses to the noxious mechanical stimulus were depressed by the test article. Hyperalgesia is regarded as being fully developed when PPTs in the ipsilateral hindpaw are ≤80 g, whereas for non-injured rats the baseline PPTs in the hindpaws are ~120 g. Restoring PPTs in the ipsilateral hindpaw from ≤80 g to pre-FCA levels (~120 g) is the treatment goal representing full reversal of mechanical hyperalgesia.

Paw pressure testing was performed prior to i.pl. FCA administration, and on day 5 post-FCA, and at the following times: pre-dose and 0.25, 0.5, 0.75, 1, 1.25, 1.5, 2 and 3 h post-dosing.

Paw Volume Measurement

Paw volume was assessed using displacement of water by the hindpaw to indicate the paw volume. These measurements were undertaken for both the ipsilateral and contralateral hindpaws prior to and 5 days after i.pl. FCA administration and prior to and 3 h post-dosing.

Test Article Administration

Single bolus doses of EMA500, EMA600 and vehicle were administered by the i.p. route and paw withdrawal thresholds in the hindpaws were assessed using a Ugo Basile Analgesiometer in order to assess the anti-hyperalgesic efficacy of EMA500 and EMA600 in the injured (ipsilateral) hindpaw of FCA-rats. Similarly, single bolus doses of morphine were administered by the s.c. route to drug-naïve FCA-rats.

Behavioural Observations

The animals were monitored for visible and audible signs of distress throughout the testing period. The visible signs of distress included behavioural changes such as complete immobility, movement with abnormal gait, agitation, aggression, wet dog shakes, excessive grooming, restlessness with constant movement, repeated sudden movements or staring.

Rat Euthanasia and Disposal

After completion of the experimental protocol, rats were euthanized with 100% CO2 followed by cervical dislocation. Rat carcasses were frozen until removal by The University of Queensland biological waste removal service.

Data Analysis

Mean (±SEM) PPT versus time curves were plotted for each of the Test Articles, morphine and vehicle in FCA-rats. All data with n=2 was graphed as mean (±SD).

Statistical Analysis

The Mann-Whitney or Kruskall Wallis nonparametric tests, as implemented in the GraphPad Prism™ statistical analysis program (v3.0) were used to compare (i) paw pressure thresholds before and after i.pl. FCA injection (ii) the effect of EMA compounds, morphine or vehicle on paw pressure thresholds after i.pl. FCA injection.

Example 3

Effects of EMA Compounds on Monoarthritis Induced Mechanical Hyperalgesia in Rats Eighty rats were used. Three rats were excluded from the study because they were polyarthritic. The number of animals in the different experimental groups is mentioned below:
Vehicle: n=10
EMA300 (0.1 mg/kg): n=9
EMA300 (1 mg/kg): n=10
EMA300 (10 mg/kg): n=10
EMA400 (0.1 mg/kg): n=10
EMA400 (1 mg/kg): n=9
EMA400 (10 mg/kg): n=9
Morphine: n=10
Solubility issues were observed with EMA400 (PD-126,055) at 10 mg/kg but not at 1 mg/kg and 0.1 mg/kg. No solubility issue was evidenced with EMA300 (PD-121,981).

Figure 7:
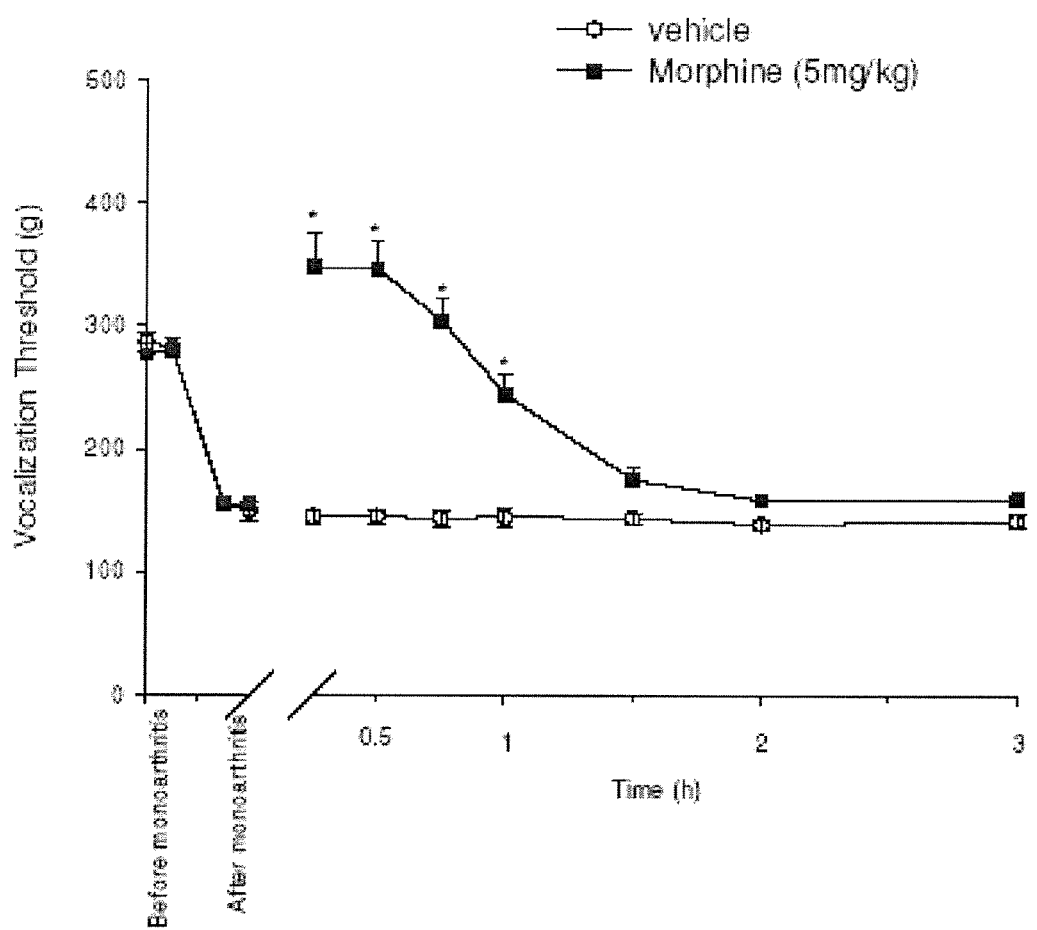
FIG. 7 is a graphical representation illustrating a time course effect (3 h) of i.p. injections of morphine on the vocalization threshold to paw pressure in monoarthritic rats. Vocalization thresholds (expressed in gram) were measured before and after (14 days) induction of monoarthritis induced by an intraarticular injection of CFA just before drug injections and 0.25, 0.5, 0.75, 1, 1.5, 2 and 3 h after drug injection. n=10 rats in each group. * p<0.05 vs vehicle-treated group.

Morphine induced an antinociceptive effect characterized by a significant increase in the vocalization threshold of monoarthritic rats as compared to the pre-induction values (FIG. 7).

Figure 8:
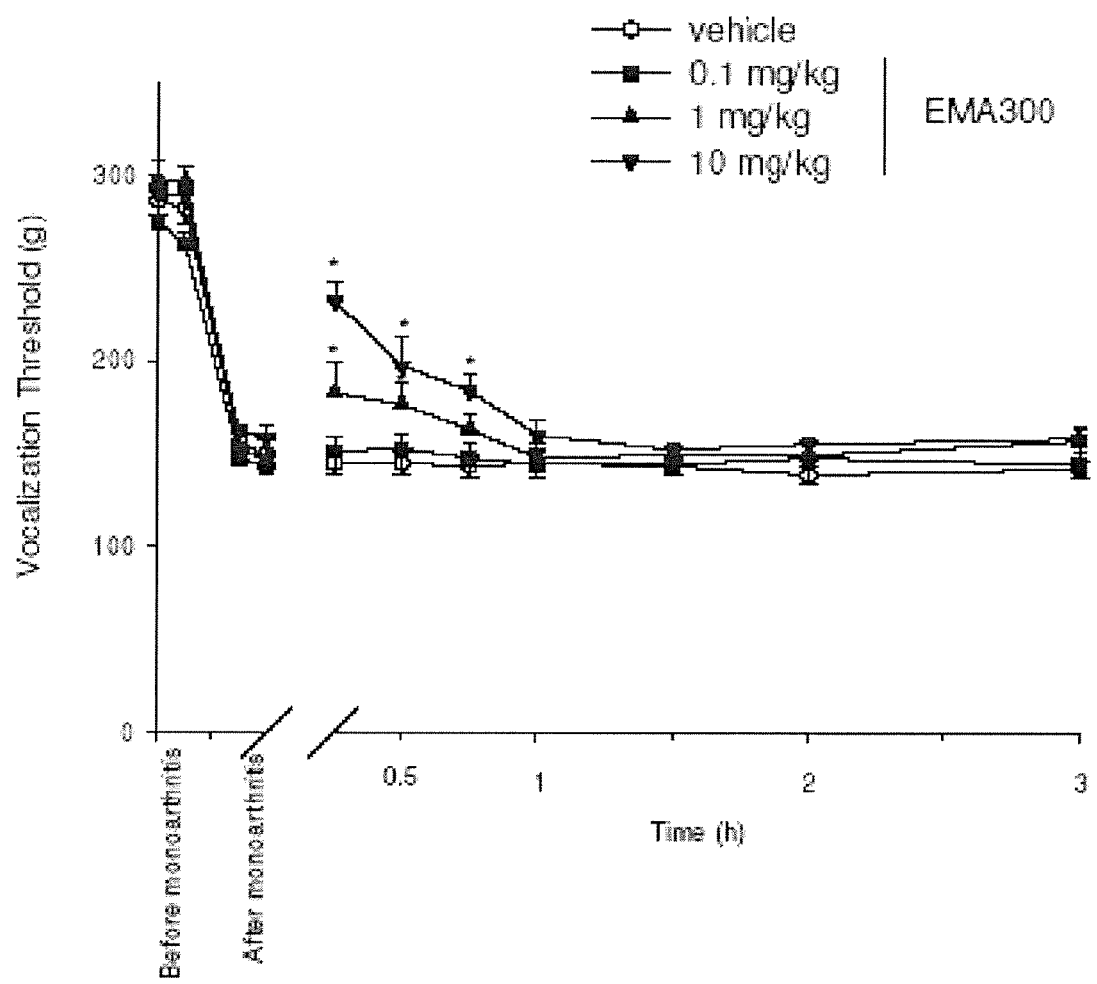
FIG. 8 is a graphical representation showing a time course effect (3 h) of i.p. injections of EMA300 on the vocalization threshold to paw pressure in monoarthritic rats. Vocalization thresholds (expressed in gram) were measured before and after (14 days) induction of monoarthritis induced by an intraarticular injection of CFA just before drug injection and 0.25, 0.5, 0.75, 1, 1.5, 2 and 3 h after drug injection. n=9-10 rats in each group. * p<0.05 vs vehicle-treated group.

EMA300 induced a dose-dependent antihyperalgesic effect (+6%, +22% and +56% at 15 and 30 minutes after drug injection for the doses of 0.1, 1 and 10 mg/kg, respectively) (FIG. 8).

Figure 9:
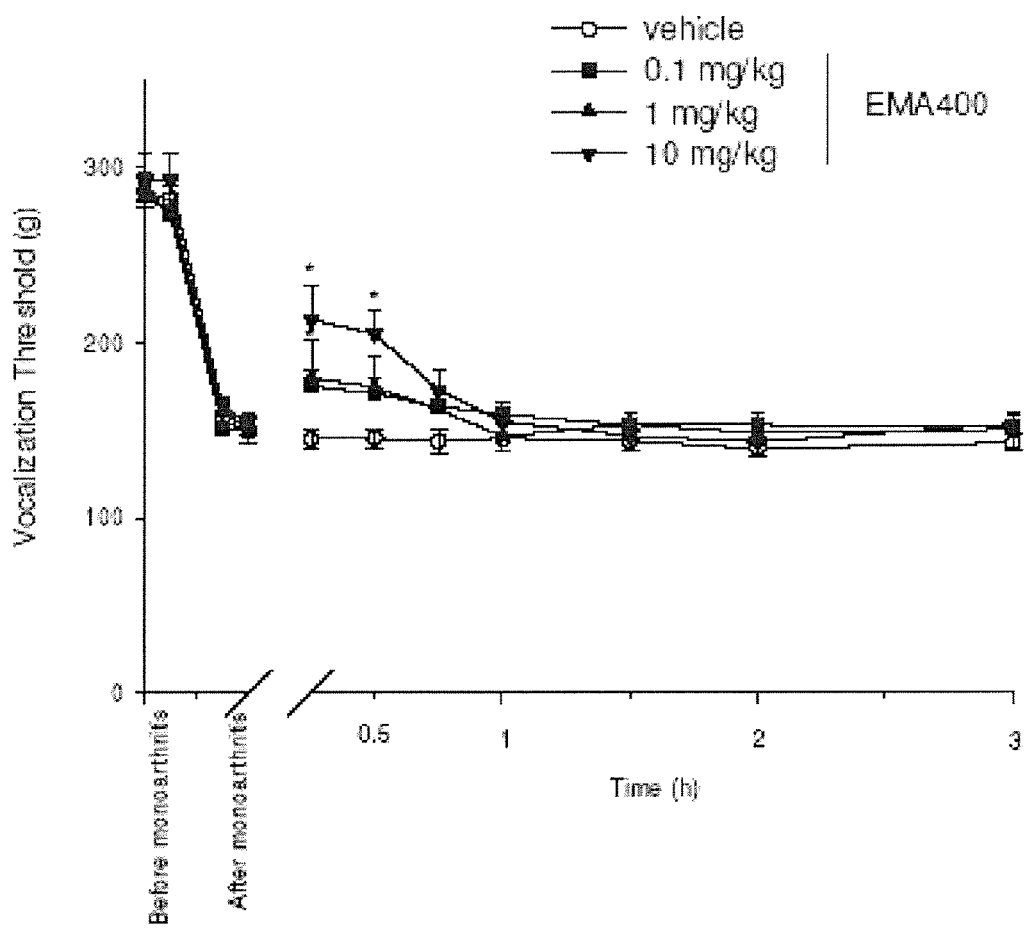
FIG. 9 is a graphical representation illustrating a time course effect (3 h) of i.p. injections of EMA400 on the vocalization threshold to paw pressure in monoarthritic rats. Vocalization thresholds (expressed in gram) were measured before and after (14 days) induction of monoarthritis induced by an intraarticular injection of CFA just before drug injection and 0.25, 0.5, 0.75, 1, 1.5, 2 and 3 h after drug injections. n=9-10 rats in each group. * p<0.05 vs vehicle-treated group.

EMA400 induced a significant antihyperalgesic effect 15 minutes after the injection of the 1 mg/kg dose (+20%). At 10 mg/kg, a significant antihyperalgesic effect was observed 15 minutes (+40%) and 30 minutes after the injection (FIG. 9).

CONCLUSION

This study clearly shows that EMA300 and EMA400 induce antihyperalgesic effects in a model of monoarthritis in rats. The lower effect of EMA400 relative to EMA300 might be explained by some dissolution issues.

MATERIALS AND METHODS

Animals 80 male Sprague-Dawley rats (Charles River, France) weighing 180 g to 200 g at the beginning of the experimental phase were included in this study. They were housed in a temperature (19.5° C.-24.5° C.) and relative humidity (45-65%) controlled room with a 12 h light/dark cycle, with ad libitum access to filtered tap-water and standard pelleted laboratory chow (SAFE, France) throughout the study. Rats were housed 4 per cage and a 7-day acclimatization period was observed before any testing. Animals were individually identified on the tail. The study was performed according to the guidelines of the Committee for Research and Ethical Issue of the I.A.S.P. (1983).

Test Articles

| Test substances (name/code) | Batch | Salt/Base ratio | Form | Source |
|---|---|---|---|---|
| EMA300 | Sm06-69 | sodium salt | powder | GlycoSyn |
| EMA400 | Sm05-196-2.1.1 | free carboxylic acid | powder | GlycoSyn |

EMA300 (PD-121,981) was prepared as described in U.S. Pat. No. 4,812,462. EMA400 (PD126,055) was prepared as described in International Publication No. WO 93/23378. Both EMA300 and EMA400 were synthesized and supplied by GlycoSyn, a business unit of Industrial Research Limited (New Zealand).

STUDY MATERIALS

Reference Substance

| Reference substance (name/code) | Batch | Salt/Base ratio | Form | Source |
|---|---|---|---|---|
| MORPHINE | D2893/9 | 1.13 | powder | COOPER |

Vehicle

NaCl 0.9% (4151A101, B. BRAUN, France), DMSO (0503831, PROLABO, France). The vehicle was NaCl 0.9%/DMSO (50/50)

Reagent

Freund's Complete Adjuvant (0640, DIFCO laboratories, USA).

Principal Equipment

Ugo Basile Analgesiometer (Ugo Basile, Italy) was used for the paw pressure test.

Principal Data Processing Systems

SigmaStat software was used for statistical analysis.

Experimental Design

| Group | # of rats | Compound | Dose (mg/kg) | Route | Volume |
|-------|-----------|----------|--------------|-------|--------|
| 1 | 10 | EMA300 | 0.1 | ip | 2 mL/kg |
| 2 | 10 | EMA300 | 1 | ip | 2 mL/kg |
| 3 | 10 | EMA300 | 10 | ip | 2 mL/kg |
| 4 | 10 | EMA400 | 0.1 | ip | 2 mL/kg |
| 5 | 10 | EMA400 | 1 | ip | 2 mL/kg |
| 6 | 10 | EMA400 | 10 | ip | 2 mL/kg |
| 7 | 10 | Morphine | 5 | ip | 2 mL/kg |
| 8 | 10 | Vehicle | — | ip | 2 mL/kg |

Experimental Procedure

Experimentation was done blindly using the block method with randomization. Unilateral monoarthritits was induced by an intraarticular injection of FCA (0.05 ml) into the tibia tarsal cavity of the right hindpaw of the rat under volatile anaesthetic (5% isofluorane). Fourteen days later, drugs were intraperitoneally given as a single administration. Pain reaction thresholds (vocalization or struggle) were measured using the paw pressure test before induction of monoarthritis, just before drug injections and 15 min, 30 min, 45 min, 1 h, 1 h30, 2 h and 3 h after drug injections. Pressure was gradually applied to the injected hindpaw of the rat (tibio tarsal articulation) and pain reaction thresholds were determined as the pressure (g) required to elicit struggle or vocalization.

Data Presentation and Statistical Analyses

Results were expressed as pressure (g) which induces pain reaction (mean+/−SEM). The cut-off value corresponds to the maximum pressure that the apparatus allows (750 g). Data were analyzed by a two-way analysis of variance (ANOVA) to compare time-course scores. These analyses were followed by a Tukey test when the F-value was significant. The significance level was $p<0.05$.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

---

What is claimed is:

1. A method for the treatment of an inflammatory pain in a subject, comprising administering to the subject an effective amount of an $AT_2$ receptor antagonist; wherein the $AT_2$ receptor antagonist is selected from compounds represented by the formula (I):

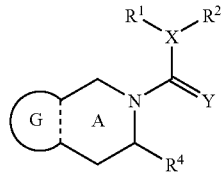

(I)

wherein:

$R^1$ and $R^2$ are independently selected from H, benzyl, substituted benzyl, phenyl, substituted phenyl, $C_{1-6}$alkyl, substituted $C_{1-6}$alkyl, $C_{3-6}$cycloalkyl, substituted $C_{3-6}$cycloalkyl, and heteroaryl, providing that both $R^1$ and $R^2$ are not hydrogen, $R^4$ is selected from a carboxylate, carboxylic acid, sulfate, phosphate, sulfonamide, phosphonamide or amide, X is selected from CH, nitrogen, sulfur or oxygen with the proviso that when X is sulfur or oxygen one of $R^1$ or $R^2$ is absent, Y is selected from sulfur, oxygen or N—$R^N$, where $R^N$ is selected from H, $C_{1-6}$alkyl, substituted $C_{1-6}$alkyl, aryl, substituted aryl, benzyl, substituted benzyl, $C_{1-4}$alkylaryl, substituted $C_{1-4}$-alkylaryl, OH, or $NH_2$, G is selected from one of the following rings systems:

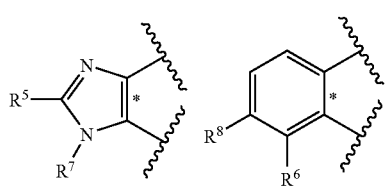

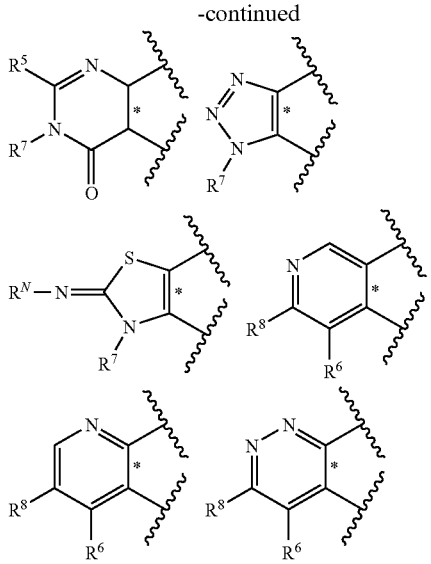

where the symbol '*' indicates the bond shared between the fused rings 'A' and 'G', R$^5$ is selected from H, C$_{1-6}$alkyl, phenyl, substituted phenyl, substituted C$_{1-6}$alkyl, C$_{1-6}$alkoxy, or substituted C$_{1-6}$alkoxy, R$^6$ and R$^8$ are independently selected from H, C$_{1-6}$alkyl, substituted C$_{1-6}$alkyl, C$_{1-6}$alkoxy, substituted; C$_{1-6}$alkoxy, phenyl, phenyloxy, benzyl, benzyloxy, benzylamino, biphenyl, substituted biphenyl, biphenyloxy, substituted biphenyloxy, naphthyl, substituted naphthyl, provided that one of R$^6$ or R$^8$ is not hydrogen, and R$^7$ is selected from phenyl, substituted phenyl, benzyl, substituted benzyl, biphenyl, substituted biphenyl, biphenylmethylene, substituted biphenylmethylene, naphthyl, substituted naphthyl, naphthylmethylene, and substituted naphthylmethylene, or a pharmaceutically acceptable salt thereof.

2. The method according to claim 1, wherein the AT$_2$ receptor antagonist is selected from compounds, or pharmaceutically acceptable salts thereof, represented by the formula (IX):

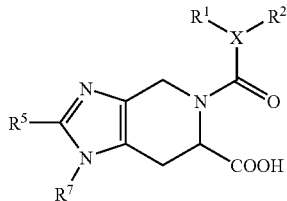

(IX)

wherein:
X is selected from CH or nitrogen,
R$^1$ and R$^2$ are independently selected from phenyl, substituted phenyl, benzyl, substituted benzyl, C$_{1-6}$alkyl, substituted C$_{1-6}$alkyl, C$_{3-6}$cycloalkyl, substituted C$_{3-6}$cycloalkyl and heteroaryl,
R$^5$ is selected from hydrogen, C$_{1-6}$alkyl, phenyl, substituted phenyl, substituted C$_{1-6}$alkyl, C$_{1-6}$alkoxy, and substituted C$_{1-6}$alkoxy, and
R$^7$ is selected from is selected from phenyl, substituted phenyl, benzyl, substituted benzyl, biphenyl, substituted biphenyl, biphenylmethylene, substituted biphenylmethylene, naphthyl, substituted naphthyl, naphthylmethylene, and substituted naphthylmethylene.

3. The method according to claim 1, wherein the AT$_2$ receptor antagonist is selected from compounds, or pharmaceutically acceptable salts thereof, represented by the formula (X):

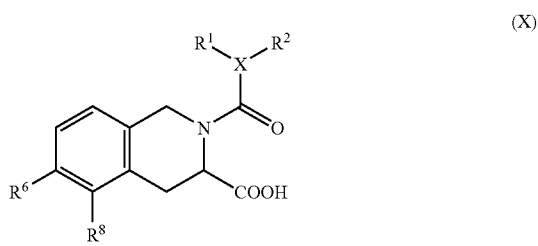

(X)

wherein:
X is selected from CH or nitrogen,
R$^1$ and R$^2$ are independently selected from phenyl, substituted phenyl, benzyl, substituted benzyl, C$_{1-6}$alkyl, substituted C$_{1-6}$alkyl, C$_{3-6}$cycloalkyl, substituted C$_{3-6}$cycloalkyl and heteroaryl, and
R$^6$ and R$^8$ are independently selected from H, C$_{1-6}$alkyl, substituted C$_{1-6}$alkyl, C$_{1-6}$alkoxy, substituted C$_{1-6}$alkoxy, phenyl, phenyloxy, benzyl, benzyloxy, benzylamino, biphenyl, substituted biphenyl, biphenyloxy, substituted biphenyloxy, naphthyl, substituted naphthyl, provided that one of R$^6$ or R$^8$ is not hydrogen.

4. The method according to claim 2, wherein the AT$_2$ receptor antagonist is selected from compounds, or pharmaceutically acceptable salts thereof, represented by the formula (IX), wherein R$^1$ and R$^2$ are phenyl, X is CH, R$^5$ is hydrogen or C$_{1-4}$alkyl, and R$^7$ is selected from substituted benzyl.

5. The method according to claim 2, wherein the AT$_2$ receptor antagonist is selected from compounds, or pharmaceutically acceptable salts thereof, represented by the formula (IX), R$^5$ is hydrogen and R$^7$ is selected from 4-(N,N-dimethylamino)-3-methylbenzyl, 4-methoxy-3-methylbenzyl, 4-amino-3-methylbenzyl.

6. The method according to claim 1, comprising administering the AT$_2$ receptor antagonist in the form of a composition comprising a pharmaceutically acceptable carrier or diluent.

7. The method according to claim 6, comprising administering the composition by a route selected from injection, topical application or the oral route, over a period of time and in an amount, which is effective to treat the inflammatory pain.

8. The method according to claim 1, wherein the inflammatory pain results from an infection.

9. The method according to claim 8, wherein the infection is selected from a viral, bacterial or fungal infection.

10. The method according to claim 1, wherein the inflammatory pain results from a tissue burn.

11. The method according to claim 10, wherein the tissue burn is selected from a burn of the cutaneous tissue or a sunburn.

12. The method according to claim 1, wherein the inflammatory pain results from an autoimmune disease.

13. The method according to claim 12, wherein the autoimmune disease is selected from rheumatoid arthritis, inflammatory arthritis, psoriasis, ankylosing spondylitis, osteoarthritis, colitis and irritable bowel disease.

14. The method according to claim 1, wherein the inflammatory pain results from an inflammatory condition of a tissue or organ selected from skin, muscle, and joints.

15. The method according to claim 1, wherein the inflammatory pain results from a cancer.

16. The method according to claim 1, wherein the inflammatory pain results from a traumatic injury or surgery.

17. The method according to claim 1 wherein the compound of formula (I) is selected from:
- 2-(Diphenylacetyl)-5-benzyloxy-6-methoxy-1,2,3,4-tetrahydroisoquinoline-3-carboxylic acid (PD-126055) or an enantiomer thereof;
- S(+)-1-[[4-(Dimethylamino)-3-methylphenyl]methyl]-5-(diphenylacetyl)-4,5,6,7-tetrahydro-1H-imidazo[4,5-c]pyridine-6-carboxylic acid (PD-123,319); and
- S(+)-1-[[4-hydroxy-3-methylphenyl]methyl]-5-(diphenylacetyl)-4,5,6,7-tetrahydro-1H-imidazo-[4,5-c]pyridine-6-carboxylic acid (PD-121,981);
- or pharmaceutically acceptable salts thereof.

18. The method according to claim 17 wherein the $AT_2$ receptor antagonist is 2-(Diphenylacetyl)-5-benzyloxy-6-methoxy-1,2,3,4-tetrahydroisoquinoline-3-carboxylic acid (PD-126055) or an enantiomer thereof);
or pharmaceutically acceptable salts thereof.

* * * * *

UNITED STATES PATENT AND TRADEMARK OFFICE
CERTIFICATE OF CORRECTION

PATENT NO.        : 8,551,950 B2                                                                 Page 1 of 1
APPLICATION NO.   : 12/294035
DATED             : October 8, 2013
INVENTOR(S)       : Maree Therese Smith It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1417 days.

Signed and Sealed this
Fifteenth Day of September, 2015

Michelle K. Lee
*Director of the United States Patent and Trademark Office*

SEQUENCE LISTING

```
<160> NUMBER OF SEQ ID NOS: 28

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Asn Arg Val Tyr Val His Pro Ala
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Asn Arg Val Tyr Val His Pro Leu
1               5
```

```
<210> SEQ ID NO 3
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Succinyl-Arg

<400> SEQUENCE: 3

Arg Val Tyr Val His Pro Ala
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide

<400> SEQUENCE: 4

Asp Arg Val Tyr Val His Pro Ala
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic peptide

<400> SEQUENCE: 5

Arg Val Tyr Val His Pro Ala
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is MeGly (sarcosine)

<400> SEQUENCE: 6

Xaa Arg Val Tyr His Pro Ala
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic peptide

<400> SEQUENCE: 7

Ser Arg Val Tyr His Pro Ala
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: Succinamyl-Arg

<400> SEQUENCE: 8

Arg Val Tyr Val His Pro Ala
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide

<400> SEQUENCE: 9

Asn Arg Val Tyr Val His Pro Gly
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

Asn Arg Val Tyr Val His Pro Ile
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is MeGly (sarcosine)

<400> SEQUENCE: 11

Xaa Arg Val Tyr Val His Pro Gly
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

Pro Arg Val Tyr Val His Pro Gly
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

Asn Arg Val Tyr Val His Pro Gly
1               5

<210> SEQ ID NO 14
```

```
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is MeGly (sarcosine)
<220> FEATURE:
<221> NAME/KEY: MISC_FEATURE
<222> LOCATION: (8)..(8)
<223> OTHER INFORMATION: beta-Ala

<400> SEQUENCE: 14

Xaa Arg Val Tyr Val His Pro Ala
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: beta-Ala

<400> SEQUENCE: 15

Asn Arg Val Tyr Val His Pro Ala
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide

<400> SEQUENCE: 16

Gly Arg Val Tyr Val His Pro Ala
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is MeGly (sarcosine)

<400> SEQUENCE: 17

Xaa Arg Val Tyr Ile His Pro Leu
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

Asn Arg Val Tyr Val His Pro Leu
1               5
```

```
<210> SEQ ID NO 19
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is MeGly (sarcosine)

<400> SEQUENCE: 19

Xaa Arg Val Tyr Ile His Pro Ala
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide

<400> SEQUENCE: 20

Asn Arg Val Tyr Ile His Pro Ala
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic peptide

<400> SEQUENCE: 21

Asn Arg Val Tyr Ala His Pro Ala
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic peptide

<400> SEQUENCE: 22

Asp Arg Val Phe Ile His Pro Tyr
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa is p-NH2Phe

<400> SEQUENCE: 23

Asp Arg Val Tyr Ile Xaa Pro Phe
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: nicotinic acid-Tyr
<220> FEATURE:
<221> NAME/KEY: MISC_FEATURE
<222> LOCATION: (2)..(2)
<223> OTHER INFORMATION: Xaa is N-benzoylcarbonyl-Arg

<400> SEQUENCE: 24

Tyr Xaa Lys His Pro Ile
1               5

<210> SEQ ID NO 25
<211> LENGTH: 363
<212> TYPE: PRT
<213> ORGANISM: Homo sapiens

<400> SEQUENCE: 25

Met Lys Gly Asn Ser Thr Leu Ala Thr Thr Ser Lys Asn Ile Thr Ser
1               5                   10                  15

Gly Leu His Phe Gly Leu Val Asn Ile Ser Gly Asn Asn Glu Ser Thr
                20                  25                  30

Leu Asn Cys Ser Gln Lys Pro Ser Asp Lys His Leu Asp Ala Ile Pro
            35                  40                  45

Ile Leu Tyr Tyr Ile Ile Phe Val Ile Gly Phe Leu Val Asn Ile Val
    50                  55                  60

Val Val Thr Leu Phe Cys Cys Gln Lys Gly Pro Lys Lys Val Ser Ser
65                  70                  75                  80

Ile Tyr Ile Phe Asn Leu Ala Val Ala Asp Leu Leu Leu Leu Ala Thr
                85                  90                  95

Leu Pro Leu Trp Ala Thr Tyr Tyr Ser Tyr Arg Tyr Asp Trp Leu Phe
                100                 105                 110

Gly Pro Val Met Cys Lys Val Phe Gly Ser Phe Leu Thr Leu Asn Met
            115                 120                 125

Phe Ala Ser Ile Phe Phe Ile Thr Cys Met Ser Val Asp Arg Tyr Gln
    130                 135                 140

Ser Val Ile Tyr Pro Phe Leu Ser Gln Arg Arg Asn Pro Trp Gln Ala
145                 150                 155                 160

Ser Tyr Ile Val Pro Leu Val Trp Cys Met Ala Cys Leu Ser Ser Leu
                165                 170                 175

Pro Thr Phe Tyr Phe Arg Asp Val Arg Thr Ile Glu Tyr Leu Gly Val
            180                 185                 190

Asn Ala Cys Ile Met Ala Phe Pro Pro Glu Lys Tyr Ala Gln Trp Ser
    195                 200                 205

Ala Gly Ile Ala Leu Met Lys Asn Ile Leu Gly Phe Ile Ile Pro Leu
210                 215                 220

Ile Phe Ile Ala Thr Cys Tyr Phe Gly Ile Arg Lys His Leu Leu Lys
225                 230                 235                 240

Thr Asn Ser Tyr Gly Lys Asn Arg Ile Thr Arg Asp Gln Val Leu Lys
                245                 250                 255

Met Ala Ala Ala Val Val Leu Ala Phe Ile Ile Cys Trp Leu Pro Phe
            260                 265                 270

His Val Leu Thr Phe Leu Asp Ala Leu Ala Trp Met Gly Val Ile Asn
    275                 280                 285

Ser Cys Glu Val Ile Ala Val Ile Asp Leu Ala Leu Pro Phe Ala Ile
290                 295                 300

Leu Leu Gly Phe Thr Asn Ser Cys Val Asn Pro Phe Leu Tyr Cys Phe
305                 310                 315                 320
```

```
Val Gly Asn Arg Phe Gln Gln Lys Leu Arg Ser Val Phe Arg Val Pro
            325                 330                 335

Ile Thr Trp Leu Gln Gly Lys Arg Glu Ser Met Ser Cys Arg Lys Ser
            340                 345                 350

Ser Ser Leu Arg Glu Met Glu Thr Phe Val Ser
            355                 360

<210> SEQ ID NO 26
<211> LENGTH: 363
<212> TYPE: PRT
<213> ORGANISM: Mus musculus

<400> SEQUENCE: 26

Met Lys Asp Asn Phe Ser Phe Ala Ala Thr Ser Arg Asn Ile Thr Ser
1               5                   10                  15

Ser Arg Pro Phe Asp Asn Leu Asn Ala Thr Gly Thr Asn Glu Ser Ala
            20                  25                  30

Phe Asn Cys Ser His Lys Pro Ser Asp Lys His Leu Glu Ala Ile Pro
        35                  40                  45

Val Leu Tyr Tyr Met Ile Phe Val Ile Gly Phe Ala Val Asn Ile Val
    50                  55                  60

Val Val Ser Leu Phe Cys Cys Gln Lys Gly Pro Lys Lys Val Ser Ser
65                  70                  75                  80

Ile Tyr Ile Phe Asn Leu Ala Leu Ala Asp Leu Leu Leu Leu Ala Thr
                85                  90                  95

Leu Pro Leu Trp Ala Thr Tyr Tyr Ser Tyr Arg Tyr Asp Trp Leu Phe
            100                 105                 110

Gly Pro Val Met Cys Lys Val Phe Gly Ser Phe Leu Thr Leu Asn Met
        115                 120                 125

Phe Ala Ser Ile Phe Phe Ile Thr Cys Met Ser Val Asp Arg Tyr Gln
    130                 135                 140

Ser Val Ile Tyr Pro Phe Leu Ser Gln Arg Arg Asn Pro Trp Gln Ala
145                 150                 155                 160

Ser Tyr Val Pro Leu Val Trp Cys Met Ala Cys Leu Ser Ser Leu
                165                 170                 175

Pro Thr Phe Tyr Phe Arg Asp Val Arg Thr Ile Glu Tyr Leu Gly Val
            180                 185                 190

Asn Ala Cys Ile Met Ala Phe Pro Pro Glu Lys Tyr Ala Gln Trp Ser
        195                 200                 205

Ala Gly Ile Ala Leu Met Lys Asn Ile Leu Gly Phe Ile Ile Pro Leu
    210                 215                 220

Ile Phe Ile Ala Thr Cys Tyr Phe Gly Ile Arg Lys His Leu Leu Lys
225                 230                 235                 240

Thr Asn Ser Tyr Gly Lys Asn Arg Ile Thr Arg Asp Gln Val Leu Lys
                245                 250                 255

Met Ala Ala Ala Val Val Leu Ala Phe Ile Ile Cys Trp Leu Pro Phe
            260                 265                 270

His Val Leu Thr Phe Leu Asp Ala Leu Thr Trp Met Gly Ile Ile Asn
        275                 280                 285

Ser Cys Glu Val Ile Ala Val Ile Asp Leu Ala Leu Pro Phe Ala Ile
    290                 295                 300

Leu Leu Gly Phe Thr Asn Ser Cys Val Asn Pro Phe Leu Tyr Cys Phe
305                 310                 315                 320

Val Gly Asn Arg Phe Gln Gln Lys Leu Arg Ser Val Phe Arg Val Pro
                325                 330                 335
```

```
Ile Thr Trp Leu Gln Gly Lys Arg Glu Thr Met Ser Cys Arg Lys Gly
                340                 345                 350

Ser Ser Leu Arg Glu Met Asp Thr Phe Val Ser
            355                 360

<210> SEQ ID NO 27
<211> LENGTH: 363
<212> TYPE: PRT
<213> ORGANISM: Rattus norvegicus

<400> SEQUENCE: 27

Met Lys Asp Asn Phe Ser Phe Ala Ala Thr Ser Arg Asn Ile Thr Ser
1               5                   10                  15

Ser Leu Pro Phe Asp Asn Leu Asn Ala Thr Gly Thr Asn Glu Ser Ala
            20                  25                  30

Phe Asn Cys Ser His Lys Pro Ala Asp Lys His Leu Glu Ala Ile Pro
        35                  40                  45

Val Leu Tyr Tyr Met Ile Phe Val Ile Gly Phe Ala Val Asn Ile Val
    50                  55                  60

Val Val Ser Leu Phe Cys Cys Gln Lys Gly Pro Lys Lys Val Ser Ser
65                  70                  75                  80

Ile Tyr Ile Phe Asn Leu Ala Val Ala Asp Leu Leu Leu Leu Ala Thr
                85                  90                  95

Leu Pro Leu Trp Ala Thr Tyr Tyr Ser Tyr Arg Tyr Asp Trp Leu Phe
            100                 105                 110

Gly Pro Val Met Cys Lys Val Phe Gly Ser Phe Leu Thr Leu Asn Met
        115                 120                 125

Phe Ala Ser Ile Phe Phe Ile Thr Cys Met Ser Val Asp Arg Tyr Gln
    130                 135                 140

Ser Val Ile Tyr Pro Phe Leu Ser Gln Arg Arg Asn Pro Trp Gln Ala
145                 150                 155                 160

Ser Tyr Val Val Pro Leu Val Trp Cys Met Ala Cys Leu Ser Ser Leu
                165                 170                 175

Pro Thr Phe Tyr Phe Arg Asp Val Arg Thr Ile Glu Tyr Leu Gly Val
            180                 185                 190

Asn Ala Cys Ile Met Ala Phe Pro Pro Glu Lys Tyr Ala Gln Trp Ser
        195                 200                 205

Ala Gly Ile Ala Leu Met Lys Asn Ile Leu Gly Phe Ile Ile Pro Leu
    210                 215                 220

Ile Phe Ile Ala Thr Cys Tyr Phe Gly Ile Arg Lys His Leu Leu Lys
225                 230                 235                 240

Thr Asn Ser Tyr Gly Lys Asn Arg Ile Thr Arg Asp Gln Val Leu Lys
                245                 250                 255

Met Ala Ala Ala Val Val Leu Ala Phe Ile Ile Cys Trp Leu Pro Phe
            260                 265                 270

His Val Leu Thr Phe Leu Asp Ala Leu Thr Trp Met Gly Ile Ile Asn
        275                 280                 285

Ser Cys Glu Val Ile Ala Val Ile Asp Leu Ala Leu Pro Phe Ala Ile
    290                 295                 300

Leu Leu Gly Phe Thr Asn Ser Cys Val Asn Pro Phe Leu Tyr Cys Phe
305                 310                 315                 320

Val Gly Asn Arg Phe Gln Gln Lys Leu Arg Ser Val Phe Arg Val Pro
                325                 330                 335

Ile Thr Trp Leu Gln Gly Lys Arg Glu Thr Met Ser Cys Arg Lys Ser
            340                 345                 350
```

```
Ser Ser Leu Arg Glu Met Asp Thr Phe Val Ser
        355                 360

<210> SEQ ID NO 28
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is absent or is L-Asp, MeGly, L-Ser, Gly,
      L- Tyr, Na-nicotinoyl-Tyr, or D- or L-Asn
<220> FEATURE:
<221> NAME/KEY: MISC_FEATURE
<222> LOCATION: (2)..(2)
<223> OTHER INFORMATION: Xaa is Arg or N-benzoylcarbonyl Arg (where Xaa
      at position 1 is absent the Arg or N-benzoylcarbonylArg at
      position 2 may bear an succinyl, succinamyl or propyl group)
<220> FEATURE:
<221> NAME/KEY: MISC_FEATURE
<222> LOCATION: (3)..(3)
<223> OTHER INFORMATION: Xaa is absent or Val
<220> FEATURE:
<221> NAME/KEY: MISC_FEATURE
<222> LOCATION: (4)..(4)
<223> OTHER INFORMATION: Xaa is absent or L-Phe or L-Tyr
<220> FEATURE:
<221> NAME/KEY: MISC_FEATURE
<222> LOCATION: (5)..(5)
<223> OTHER INFORMATION: Xaa is Val, L-Ile, L-Ala or L-Lys
<220> FEATURE:
<221> NAME/KEY: MISC_FEATURE
<222> LOCATION: (6)..(6)
<223> OTHER INFORMATION: Xaa is L-His, L-Ile, L-Tyr or
      p-aminophenylalanine
<220> FEATURE:
<221> NAME/KEY: MISC_FEATURE
<222> LOCATION: (8)..(8)
<223> OTHER INFORMATION: Xaa is L-Ala, L- Tyr, L- or D-Leu, Gly,
      L-Ile or  bAla (beta-alanine)

<400> SEQUENCE: 28

Xaa Xaa Xaa Xaa Xaa Xaa Pro Xaa
1               5
```